(12) United States Patent
Walensky et al.

(10) Patent No.: US 11,945,846 B2
(45) Date of Patent: Apr. 2, 2024

(54) STAPLED INTRACELLULAR-TARGETING ANTIMICROBIAL PEPTIDES TO TREAT INFECTION

(71) Applicant: Dana-Farber Cancer Institute, Inc., Boston, MA (US)

(72) Inventors: Loren D. Walensky, Newton, MA (US); Rida Mourtada, Brookline, MA (US)

(73) Assignee: Dana-Farber Cancer Institute, Inc., Boston, MA (US)

( * ) Notice: Subject to any disclaimer, the term of this patent is extended or adjusted under 35 U.S.C. 154(b) by 266 days.

(21) Appl. No.: 16/813,528

(22) Filed: Mar. 9, 2020

(65) Prior Publication Data
US 2020/0308236 A1    Oct. 1, 2020

Related U.S. Application Data

(63) Continuation of application No. 15/445,502, filed on Feb. 28, 2017, now abandoned.

(60) Provisional application No. 62/301,426, filed on Feb. 29, 2016.

(51) Int. Cl.
| | |
|---|---|
| A61K 38/08 | (2019.01) |
| A61K 38/10 | (2006.01) |
| A61K 38/17 | (2006.01) |
| A61K 45/06 | (2006.01) |
| C07K 7/06 | (2006.01) |
| C07K 7/08 | (2006.01) |
| C07K 14/435 | (2006.01) |
| C07K 14/46 | (2006.01) |
| C07K 14/47 | (2006.01) |

(52) U.S. Cl.
CPC ............ C07K 14/461 (2013.01); A61K 38/08 (2013.01); A61K 38/10 (2013.01); A61K 38/1703 (2013.01); A61K 38/1706 (2013.01); A61K 38/1709 (2013.01); A61K 38/1767 (2013.01); A61K 45/06 (2013.01); C07K 7/06 (2013.01); C07K 7/08 (2013.01); C07K 14/43504 (2013.01); C07K 14/463 (2013.01); C07K 14/47 (2013.01)

(58) Field of Classification Search
None
See application file for complete search history.

(56) References Cited

U.S. PATENT DOCUMENTS

| | | | |
|---|---|---|---|
| 5,446,090 A | 8/1995 | Harris | |
| 5,607,914 A | 3/1997 | Roa et al. | |
| 5,861,478 A | 1/1999 | Jaynes | |
| 5,885,829 A | 3/1999 | Mooney et al. | |
| 5,912,231 A | 6/1999 | Houghten et al. | |
| 6,001,805 A | 12/1999 | Jaynes et al. | |
| 6,348,558 B1 | 2/2002 | Harris et al. | |
| 6,620,954 B1 | 9/2003 | Boaz | |
| 7,723,468 B2 | 5/2010 | Daffre et al. | |
| 8,198,405 B2 | 6/2012 | Walensky et al. | |
| 8,889,632 B2 | 11/2014 | Bernal et al. | |
| 9,079,970 B2 | 7/2015 | Walensky et al. | |
| 9,296,805 B2 | 3/2016 | Walensky et al. | |
| 9,464,115 B2 * | 10/2016 | Walensky ................ | C07K 7/64 |
| 9,527,896 B2 | 12/2016 | Bernal et al. | |
| 10,464,975 B2 | 11/2019 | Walensky et al. | |
| 2001/0025048 A1 | 9/2001 | Crabb et al. | |
| 2003/0096949 A1 | 5/2003 | Hancock et al. | |
| 2003/0104581 A1 | 6/2003 | Hoess et al. | |
| 2005/0250680 A1 | 11/2005 | Walensky et al. | |
| 2006/0287232 A1 | 12/2006 | Clayberger et al. | |
| 2010/0093086 A1 | 4/2010 | Lin et al. | |
| 2010/0069308 A1 | 5/2010 | Chorny et al. | |
| 2010/0168388 A1 | 7/2010 | Bernal et al. | |
| 2010/0286057 A1 | 11/2010 | Walensky et al. | |
| 2011/0159091 A1 | 6/2011 | Stone et al. | |
| 2011/0288007 A1 | 11/2011 | Fox et al. | |
| 2012/0172285 A1 | 7/2012 | Walensky et al. | |
| 2014/0113857 A1 | 4/2014 | Walensky et al. | |
| 2014/0155319 A1 | 6/2014 | Bond et al. | |
| 2014/0296232 A1 | 10/2014 | Hung et al. | |
| 2014/0370042 A1 | 12/2014 | Walensky et al. | |
| 2015/0087512 A1 | 3/2015 | Wang et al. | |
| 2015/0087579 A1 | 3/2015 | Stange et al. | |
| 2015/0290278 A1 | 10/2015 | Deber | |
| 2016/0046671 A1 | 2/2016 | Leshchiner et al. | |
| 2016/0068834 A1 | 3/2016 | Walensky | |
| 2016/0110706 A1 | 4/2016 | Li et al. | |
| 2016/0319436 A1 | 11/2016 | Wagh et al. | |
| 2017/0015716 A1 | 1/2017 | Walensky et al. | |
| 2017/0081379 A1 | 3/2017 | Bernal et al. | |

(Continued)

FOREIGN PATENT DOCUMENTS

| | | |
|---|---|---|
| CA | 2367149 | 9/2011 |
| CN | 103467588 | 12/2013 |

(Continued)

OTHER PUBLICATIONS

U.S. Appl. No. 17/091,541, filed Nov. 6, 2020, Walensky.
Hocquellet et al., "Structure-Activity relationship of human liver-expressed antimicrobial peptide 2," Peptides, 2010, 31:58-66.
U.S. Appl. No. 15/201,235, 2017/0015716, U.S. Pat. No. 10,464,975, filed Jul. 1, 2016, Walensky.
Alberts et al., "Bacterial shapes and cell-surface structures: Figure 25-4," *Molecular Biology of the Cell*—NCBI Bookshelf, 2002, 4th Edition, 1 page.
Alberts et al., "Visualizing Cells," *Molecular Biology of the Cell*, Chapter 9, 5th Edition, 2007, p. 579-615.

(Continued)

*Primary Examiner* — Fred H Reynolds
(74) *Attorney, Agent, or Firm* — Fish & Richardson P.C.

(57) ABSTRACT

Structurally stabilized, e.g., stapled, peptides with the ability to translocate through microbial cell membranes to the interior of microbial cells and exert a biological activity there are provided, as are methods of designing, making and using such peptides.

27 Claims, 8 Drawing Sheets
Specification includes a Sequence Listing.

(56) References Cited

U.S. PATENT DOCUMENTS

| | | | |
|---|---|---|---|
| 2017/0247423 A1 | 8/2017 | Walensky et al. | |
| 2017/0260248 A1 | 9/2017 | Walensky et al. | |
| 2020/0207821 A1* | 7/2020 | Walensky | A61L 27/227 |
| 2020/0231638 A1 | 7/2020 | Walensky et al. | |

FOREIGN PATENT DOCUMENTS

| | | |
|---|---|---|
| DE | 1991/4817 | 10/2000 |
| JP | 2010-528052 | 8/2010 |
| KR | 2010/0065639 | 6/2010 |
| WO | WO 1991/000869 | 1/1991 |
| WO | WO 1999/014259 | 3/1999 |
| WO | WO 1999/034833 | 7/1999 |
| WO | WO 1999/037644 | 7/1999 |
| WO | WO 2000/004915 | 2/2000 |
| WO | WO 2001/00209 | 1/2001 |
| WO | WO 2002/079408 | 10/2002 |
| WO | WO 2003/007989 | 10/2003 |
| WO | WO 2003/083441 | 3/2005 |
| WO | WO 2007/122482 | 11/2007 |
| WO | WO 2008/086042 | 7/2008 |
| WO | WO 2008/095063 | 8/2008 |
| WO | WO 2008/058575 | 10/2008 |
| WO | WO 2008/121767 | 10/2008 |
| WO | WO 2009/108261 | 9/2009 |
| WO | WO 2010/042534 | 4/2010 |
| WO | WO 2010/060112 | 5/2010 |
| WO | WO 2010/068684 | 6/2010 |
| WO | WO 2010/148335 | 12/2010 |
| WO | WO 2013/039857 | 3/2013 |
| WO | WO 2013/102211 | 7/2013 |
| WO | WO 2014/100777 | 6/2014 |
| WO | WO 2014/159969 | 10/2014 |
| WO | WO 2015/070912 | 5/2015 |
| WO | WO 2015/138494 | 9/2015 |
| WO | WO 2015/112980 | 10/2015 |
| WO | WO 2017/004591 | 1/2017 |
| WO | WO 2017/147283 | 8/2017 |
| WO | WO 2017/151617 | 9/2017 |
| WO | WO 2019/018499 | 1/2019 |

OTHER PUBLICATIONS

Altschul et al. (1997) "Gapped BLAST and PSI-BLAST: a new generation of protein database search programs," Nucleic Acids Res. 25:3389-3402.

Amsel et al. "Nonspecific vaginitis. Diagnostic criteria and microbial and epidemiologic associations," Am. J. Med. 74:14-22 (1983).

Arnusch et al., "Enhanced membrane pore formation through high-affinity targeted antimicrobial peptides," PLoS One, 2012, 7(6):e39768, 5 pages.

Bajaj, Kanika et al., "Stereochemical criteria for prediction of the effects of proline mutations on protein stability." PLoS Connput. Biol. (2007) 3(12) e241.

Bang, et al., (2004) "Total chemical synthesis of crambin," J. Am. Chem. Soc. 126:1377-83.

Barker, et al., "The fate of norleucine as a replacement for methionine in protein synthesis," J. Mol. Biol. 133(2):217-231 (Sep. 1979).

Bechinger, "Structure and functions of channel-forming peptides: magainins, cecropins, melittin and alamethicin," Journal of Membrane Biology, 1997, 156:197-211.

Bernal, et al., "A Stapled p53 Helix Overcomes HDMX-Mediated Suppression of p53," Cancer Cell. 18(5):411-422 (Nov. 2010).

Bird et al., (2011) "Chemical synthesis of hydrocarbon-stapled peptides for protein interaction research and therapeutic targeting," Curr Protoc Chem Biol., 3(3):99-117.

Bird et al., (2010) "Hydrocarbon double-stapling remedies the proteolytic instability of a lengthy peptide therapeutic," Proc Natl Acad Sci USA 107(32):14093-8.

Bird et. al., (2008) "Synthesis and biophysical characterization of stabilized alpha-helices of BCL-2 domains," Meth Enzymol., 446:369-386.

Bird, "Biophysical determinants for cellular uptake of hydrocarbon-stapled peptide helices," Nature Chemical Biology, Aug. 2016, 12:845-853.

Bird, et al., "Mucosal delivery of a double-stapled RSV peptide prevents nasopulmonary infection," J Clin Invest. 124(5):2113-2124 (May 2014).

Blackwell et al., "Highly Efficient Synthesis of Covalently Cross-Linked Peptide Helices by Ring-Closing Metathesis," Angewandte Chemie, Dec. 1998, 37(23):3281-3284.

Blackwell et al., (Aug. 2001) "Ring-closing metathesis of olefinic peptides: design, synthesis, and structural characterization of macrocyclic helical peptides," J Org Chem., 66(16): 5291-5302.

Blondelle et al., "Design of model amphipathic peptides having potent antimicrobial activities," Biochemistry, 1992, 31:12688-12694.

Bray, "Large-scale manufacture of peptide therapeutics by chemical synthesis," Nature Reviews Drug Discovery, 2003, 2:587-593.

Brogden, KA, "Antimicrobial peptides: pore formers or metabolic inhibitors in bacteria?" Nat. Rev. Microbiol. 3(3):238-250 (Mar. 2005).

Brunel et al., "Synthesis of constrained helical peptides by thioether ligation: application to analogs of gp41," Chemical Communications, 2005, 2552-2554.

Bustillo, et al., "Modular analysis of hipposin, a histone-derived antimicrobial peptide consisting of membrane translocating and membrane permeabilizing fragments," Biochimica Et Biophysica Acta (BBA)—Biomembranes. 1838(9):2228-2233 (2014).

Chang, et al., "Stapled α-helical peptide drug development: A potent dual inhibitor of MDM2 and MDMX for p53-dependent cancer therapy," PNAS U.S.A., 110(36):E3445-3454 (Sep. 2013).

Chapman, et al., "A highly stable short alpha-helix constrained by a main-chain hydrogen bond surrogate," J. Am. Chem. Soc. 126:12252-12253 (2004).

Chapman, Ross N., and Arora, Parannjit S; "Optimized synthesis of hydrogen-bond surrogate helicies: surprising effects of microwave heating on teh activity of grubbs catalysts." Org. Lett. (2006) 8(25) p. 5825-5828.

Chapuis et al., "Effect of hydrocarbon stapling on the properties of α-helical antimicrobial peptides isolated from the venom of hymenoptera," Amino Acids, 43(5):2047-58 (Nov. 2012).

Chekmenev et al., "Investigating molecular recognition and biological function at interfaces using piscidins, antimicrobial peptides from fish," Biochimica et Biophysica Acta, 2006, 1758(9):1359-72.

Cho et al., "Buforins: histone H2A-derived antimicrobial peptides from toad stomach," Biochimica et Biophysica Acta, 2009, 1788:1564-1569.

Dathe et al., "Hydrophobicity, hydrophobic moment and angle subtended by charged residues modulate antibacterial and haemolytic activity of amphipathic helical peptides," FEBS Letters, 1997, 403:208-212.

Del Rio et al., "APAP, a sequence-pattern recognition approach identifies substance P as a potential apoptotic peptide," FEBS Letters, 2001, 494(3): 213-219.

Devi et al., (1991) "Antibodies to poly[(2—8)-alpha-N-acetylneuraminic acid] and poly[(2—9)-alpha-N-acetylneuraminic acid] are elicited by immunization of mice with Escherichia coli K92 conjugates: potential vaccines for groups B and C meningococci and E. coli K1," Proc. Natl. Acad. Sci. USA 88(16):7175-7179.

Dinh, et al., "Antimicrobial Activity of Doubly-Stapled Alanine/Lysine-Based Peptides," Bioorg & Med Chem Lett. 25(18):4016-9 (Sep. 2015).

Epand et al., "Molecular mechanisms of membrane targeting antibiotics," Biochimica et Biophysica Acta, Oct. 2015, 1858:980-987.

European Extended Search Report in European Patent Application No. 16818936.3, dated Jun. 17, 2019, 17 pages.

ext.impmc.upmc.fr [online], "Guidlines to Hydrophobic Cluster Analysis (HCA)," 2013, retrieved Apr. 15, 2020, retrieved from URL<http://www-ext.impmc.upmc.fr/~callebau/HCA.html>, 4 pages.

Fattom et al. (Jul. 1990) "Serum antibody response in adult volunteers elicited by injection of Streptococcus pneumoniae type 12F polysaccharide alone or conjugated to diphtheria toxoid," Infect. Immun., 58(7):2309-2312.

(56) References Cited

OTHER PUBLICATIONS

Feder et al., "Structure-Activity Relationship Study of Antimicrobial Dermaseptin S4 Showing the Consequences of Peptide Oligomerization on Selective Cytotoxicity," *Journal of Biological Chemistry*, 2000, 275(6):4230-4238.
Fields et al., Chapter 3 in Synthetic Peptides: A User's Guide, ed. Grant, W. H. Freeman & Co., New York, N.Y., 1992, p. 77-183.
Fjell, et al., "Designing antimicrobial peptides: form follows function," *Nat Rev Drug Discov*. 11(1):37-51 (Dec. 2011).
Forsum et al. "Bacterial vaginosis—a microbiological and immunological enigma," *APMIS* 113(2):81-90 (Feb. 2005).
Fuerst et al., "Protein uptake by bacteria: an endocytosis-like process in the planctomycete Gemmata obscuriglobus," *Communicative & Integrative Biology*, 2010, 3(6):572-575.
Gordon, et al., "A Review of Antimicrobial Peptides and Their Therapeutic Potential as Anti-Infective Drugs," *Curr Eye Res*. 30(7):505-515 (Jul. 2005).
Haney et al., "Promoting peptide α-helix formation with dynamic covalent oxime side-chain cross-links," *Chemical Communications*, 2011, 47:10915-10917.
Hao et al., "The intracellular mechanism of action on *Escherichia coli* of BF2-A/C, two analogues of the antimicrobial peptide Buforin 2," *Journal of Microbiology*, 2013, 51(2):200-206.
Hawes et al. "Hydrogen Peroxide-Producing Lactobacilli and Acquisition of Vaginal Infections," *J. Infect. Dis*. 174:1058-1063 (1996).
Hilinski et al., "Stitched α-helical peptides via bis ring-closing metathesis," *Journal of the American Chemical Society*, 2014, 136:12314-12322.
Hilpert et al., "Peptide arrays on cellulose support: SPOT synthesis, a time and cost efficient method for synthesis of large numbers of peptides in a parallel and addressable fashion," *Nature Protocols*, 2007, 2(6):1333-1349.
Ho et al., "The flexibility in the proline ring couples to the protein backbone," *Protein Science*, 2005, 14:1011-1018.
Hoskin, et al., Studies on anticancer activities of antimicrobial peptides, *Biochim. Biophys. Acta*, 1778(2):357-375 (2008).
Huber et al., "Robust production of a peptide library using methodological synchronization," *Protein Expression and Purification*, 2009, 67:139-147.
International Preliminary Report on Patentability for Intl. App. No. PCT/US2016/040849, dated Jan. 2, 2018, (14 pages).
International Preliminary Report on Patentability in International Application No. PCT/US2017/019953, dated Sep. 4, 2018, 10 pages.
International Search Report and Written Opinion for Int. App. No. PCT/US2016/040849, dated Jan. 10, 2017 (21 pages).
International Search Report and Written Opinion for Int. App. No. PCT/US2017/019953, dated Aug. 4, 2017 (21 pages).
Jackson et al., "General Approach to the Synthesis of Short alpha-helical Peptides," *Journal of the American Chemical Society*, Nov. 1991, 113:9391-9392.
Jenner et al., "Hydrocarbon-stapled lipopeptides exhibit selective antimicrobial activity," *Biopolymers*. 108(3) (May 2017), 12 pages.
Jermy, "Evolution: Bacterial endocytosis uncovered," *Nature Reviews Microbiology*, 2010, 8:534, 1 page.
Kang et al., "Antimicrobial peptides: therapeutic potentials," *Expert review of anti-infective therapy*, 2014, 12(12):1477-1486.
Kawamoto et al. (Feb. 2012) "Design of triazole-stapled BCL9 α-helical peptides to target the ß- catenin/B-cell CLL/lymphoma 9 (BCL9) protein-protein interaction," *J Med Chem*. 55(3):1137-46.
Kim et al., "Synthesis of all-hydrocarbon stapled α-helical peptides by ring-closing olefin metathesis," *Nature Protocols*, 2011, 6(6):761-771.
Klevens, et al., Estimating Health Care-Associated Infections and Deaths in U.S. Hospitals, Public Health Reports. 122(2):160-166 (Mar. 2007).
Kovacs et al., "Determination of Intrinsic Hydrophilicity/ Hydrophobicity of Amino Acid Side Chains in Peptides in the Absence of Nearest-Neighbor or Conformational Effects," *Biopolymers*, 2006, 84(3):283-97.

Kumita et al., "Photo-control of helix content in a short peptide," *Proc. Natl. Acad. Sci. U.S.A.*, Apr. 2000, 97:3803-3808.
Lau et al., "Functionalised staple linkages for modulating the cellular activity of stapled peptides," *Chemical Science*, 2014, 5:1804-1809.
Lau et al., "Peptide stapling techniques based on different macrocyclisation chemistries," *Chemical Society Reviews*, Jan. 2015, 44(1):91-102.
Lee et al., "Solution structure and cell selectivity of piscidin 1 and its analogues," *Biochemistry*, Mar. 2007, 46(12):3653-63.
Li et al., "A versatile platform to analyze low-affinity and transient protein-protein interactions in living cells in real time," *Cell Reports*, 2014, 9:1946-1958.
Liu et al., "Comparative antimicrobial activity and mechanism of action of bovine lactoferricin-derived synthetic peptides," *Biometals*, 2011, 24:1069-1078.
Liu et al., "Use of LC/MS peptide mapping for characterization of isoforms in 15N-labeled recombinant human leptin," *Techniques in Protein Chemistry*, 1997, 8:155-63, p. 162 only.
Liu et al., "Intramolecular cyclization of the antimicrobial peptide Polybia-MPI with triazole stapling: influence on stability and bioactivity," *J Pept Sci*. 23(11):824-832 (Nov. 2017).
Lodish et al., "Schematic diagram of typical membrane proteins in a biological membrane," *Molecular Cell Biology*, 2000, 4th Edition, 1 page.
Lonhienne et al., "Endocytosis-like protein uptake in the bacterium Gemmata obscuriglobus," *Proceedings of the National Academy of Sciences*, 2010, 107(29):12883-12888.
Luong et al., "Mono-substitution effects on antimicrobial activity of stapled heptapeptides," *Arch Pharm Res*. 40(6):713-719 (Jun. 2017).
Madden et al., "Synthesis of Cell-Permeable Stapled Peptide Dual Inhibitors of the p53-Mdm2/Mdmx Interactions via Photoinduced Cycloaddition," *Bioorg. Med. Chem. Lett.*, Mar. 2011, 21:1472-1475.
Mansour, et al., "Host defense peptides: front-line immunomodulators," *Trends Immunol*. 35(9):443-450 (Sep. 2014).
Maraj et al., "Evaluation of Hemolysis in Patients with Prosthetic Heart Valves," *Clin. Cardiol.*, 1998, 21:387-392.
Messer, Posterior pituitary hormones, http://163.178.103.176/ casosberne/8hendocrino/caso44- 2/htmlc/casosb2/v2/ vasopressin. htm, available 2000.
Migon et al., "Hydrocarbon Stapled Antimicrobial Peptides," *The Protein Journal*, 37:2-12 (2018).
Munoz et al., "Elucidating die folding problem of helical peptides using empirical parameters," *Nature Structural Biology*, 1994, 1(6): 399-409.
Nicolas, Pierre, "Multifunctional host defense peptides: intracellular-targeting antimicrobial peptides," *FEBS Journal*. 276(22):6483-6496 (Nov. 2009).
Park et al., "Mechanism of action of the antimicrobial peptide buforin II: buforin ii kills microorganisms by penetrating the cell membrane and inhibiting cellular functions," *Biochem. Biophys. Res*. 244:253-257 (1998).
Park, et al., "Structure-activity analysis of buforin II, a histone H2A-derived antimicrobial peptide: The proline hinge is responsible for the cell-penetrating ability of buforin II," *Proceedings of the National Academy of Sciences*. 97(15):8245-8250 (Jul. 2000).
Patch et al., "Helical peptoid mimics of magainin-2 amide," *Journal of the American Chemical Society*, 2003, 125(40):12092-12093.
Patgiri, et al., "Solid-phase synthesis of short α-helices stabilized by the hydrogen bond surrogate approach," *Nat Protoc*. 5(11):1857-1865 (Nov. 2010).
PCT International Preliminary Report on Patentability in International Appln. No. PCT/US2018/042640, dated Jan. 21, 2020, 12 pages.
PCT International Search Report and Written Opinion in International Appln. No. PCT/US2018/042640, dated Jan. 18, 2019, 19 pages.
Pereira, et al., "Maximizing the Therapeutic Window of an Antimicrobial Drug by Imparting Mitochondrial Sequestration in Human Cells," *J. Am. Chem. Soc*. 133(10):3260-3263 (Mar. 2011).

(56) References Cited

OTHER PUBLICATIONS

Pham et al., "Truncated and constrained helical analogs of antimicrobial esculentin-2EM," *Bioorg & Med Chem Lett.*, 23(24):6717-20 (Dec. 2013).
Phelan et al., "A General Method for Constraining Short Peptides to an α-Helical Conformation," *J Am. Chem. Soc.*, Jan. 1997, 119:455-460.
Rose, et al., "Potential Role of Epithelial Cell-Derived Histone H1 Proteins in Innate Antimicrobial Defense in the Human Gastrointestinal Tract," *Infect Immun.* 66(7):3255-63 (Jul. 1998).
Schafmeister et al. (2000) "An All-Hydrocarbon Cross-Linking System for Enhancing the Helicity and Metabolic Stability of Peptides," *J Am Chem Soc.*, 122:5891-5892.
Shah, et al., "The proteome targets of intracellular targeting antimicrobial peptides," *Proteomics*. 16(8):1225-37 (Apr. 2016).
Shepard et al., "Single Turn Peptide Alpha Helices with Exceptional Stability in Water," *Journal of the American Chemical Society*, Feb. 2005, 127:2974-2983.
Spokoyny et al., "A Perfluoroaryl-Cysteine SNAr Chemistry Approach to Unprotected Peptide Stapling Bis-arylation stapling," *J. Am. Chem. Soc.*, 2013, 135(16):5946-5949.
Steinauer et al., "HOPS-dependent endosomal fusion required for efficient cytosolic delivery of therapeutic peptides and small proteins," *Proceedings of the National Academy of Sciences*, 2019, 116(2):512-521.
Stone et al., "Influence of hydrocarbon-stapling on membrane interactions of synthetic antimicrobial peptides," *Bioorg Med Chem.* 26(6):1189-1196 (Mar. 2018).
Strahl et al., "Bacterial membranes: structure, domains, and function," *Annual Review of Microbiology*, 2017, 71:519-538.
Sun et al., "Membrane permeability of hydrocarbon-cross-linked peptides," *Biophysical Journal*, 2013, 104(9):1923-1932.
Szu et al., (Nov. 1987) "Vi capsular polysaccharide-protein conjugates for prevention of typhoid fever. Preparation, characterization, and immunogenicity in laboratory animals," *J. Exp. Med.* 166(5):1510-1524.
Szu et al., (Dec. 1991) "Relation between structure and immunologic properties of the Vi capsular polysaccharide," *Infect. Immun.* 59(12):4555-4561.
Szu et al., (Oct. 1994) "Laboratory and preliminary clinical characterization of Vi capsular polysaccharide-protein conjugate vaccines," *Infect. Immun.* 62(10):4440-4444.
Thaker, et al., "Synthetic Mimics of Antimicrobial Peptides with Immunomodulatory Responses," *J. Am. Chem. Soc.* 134(27):11088-11091 (Jul. 2012).
The teaching material from the CUNY biology program https://web.archive.org/web/20000530152547/http://acadennic.brooklyn.cuny.edu/biology/bio4fv/page/sinnple.htnn, available May 2000.
Tjoeng et al., "Multiple peptide synthesis using a single support (MPS3)," *International journal of peptide and protein research*, 1990, 35(2):141-146.
Verstraelen et al. "Culture-independent analysis of vaginal microflora: the unrecognized association of Atopobium vaginae with bacterial vaginosis," *Am J. Obstet. and Gynecol.* 191(14):1130-1132 (Oct. 2004).
Walensky et al. (Sep. 2004) "Activation of apoptosis in vivo by a hydrocarbon-stapled BH3 helix," *Science*, 305(5689):1466-1470.
Walensky, et al., "Hydrocarbon-Stapled Peptides: Principles, Practice, and Progress," *J. Med. Chem.* 57(15):6275-6288 (2014).
Wiegand, et al., "Agar and broth dilution methods to determine the minimal inhibitory concentration (MIC) of antimicrobial substances," *Nat Protoc*. 3(2):163-175 (2008).
Wilen, S. H., et al., (1977) "Strategies in Optical Resolutions," *Tetrahedron* 33:2725-2736.
Williams et al. (1991) "Asymmetric Synthesis of Monosubstituted and a,a-Disubstituted a-Amino Acids via Diastereoselective Glycine Enolate Alkylations," *J. Am. Chem. Soc.*, 113:9276-9286.
Williams et al., (2003) "Efficient Asymmetric Synthesis of N-tert-Butoxycarbonyl □-Aminoacids Using 4-tert-Butoxycarbonyl-5,6-Diphenylmorpholin-2-One: (R)-(Ntert-butoxycarbonyl)allylglycine [(4-Pentenoic acid, 2-[[(1,1-dimethylethoxy)carbonyl]amino]-, (2R)-)]," *Org. Synth.*, 80:31-37.
Wimley, "Describing the mechanism of antimicrobial peptide action with the interfacial activity model," *ACS Chem. Biol.* 5(10):905-917 (2010).
Xie et al., "Effect of proline position on the antimicrobial mechanism of buforin II," *Peptides*, 2011, 32:677-682.
Yampolsky and Stoltzfus, "The exchangeability of amino acids in proteins," *Genetics*, 170:1459-1472 (2005).
Yang et al., (1986) "Calculation of Protein Conformation from Circular Dichroism," *Methods Enzymol*. 130:208-269.
Yi, et al., "Solution structure of an antimicrobial peptide buforin II," *FEBS Letters*, 398(1):87-90 (Nov. 1996).
Yin, et al., "Alpha helix mimetics in drug delivery, from Drug Discovery Research: New Frontiers in the Post-Genomic Era," Huang ed., (2007) Chapter 11: pp. 280-298.
Zasloff, M., Antimicrobial peptides of multicellular organisms, *Nature*, 415(6870):389-395 (Jan. 2002).
Zboinska et al., "Antibacterial activity of phosphono dipeptides based on 1-amino-1-meihylethanephosphonic acid," *FEMS Microbiology Letters*, 1990, (70):23-28.
U.S. Appl. No. 15/201,235, U.S. Pat. No. 10,464,975, filed Jul. 1, 2016, Walensky.
U.S. Appl. No. 16/551,102, filed Aug. 26, 2019, Walensky.
U.S. Appl. No. 15/445,502, filed Feb. 28, 2017, Walensky.
U.S. Appl. No. 16/631,315, filed Jan. 15, 2020, Walensky.
Acharya, "Extracellular and Intracellular Bacteria and Their Preferred Growth Phase Within The Host," Bacteriology, May 30, 2013, 3 pages.
Atashili et al., "Bacterial Vaginosis and HIV Acquisition: A Meta-Analysis of Published Studies." AIDS, Jul. 2008, 22(12):1493-1501.
Baker et al., "Anticancer Efficacy of Magainin2 and Analogue Peptides," Cancer Research, Jul. 1993, 53(13):3052-3057.
Balaram, "Non-standard amino acids in peptide design and protein engineering," Cur Opin Struct Biol, 1992, 2(6):845-851.
Chin et al., "Design and Evolution of a Miniature Bcl-2 Binding Protein," Angew Chem Int. Ed., 2001, 40(20):3806-3809.
Corsello et al., "Discovering the anti-cancer potential of non-oncology drugs by systematic viability profiling," Nat Cancer, 2020, 1(2):235-248.
Gunnoo et al., "Bioconjugation—using selective chemistry to enhance the properties of proteins and peptides as therapeutics and carriers," Org. Biomol. Chem., 2016, 14(34):8002-8013.
Gupta et al., "Valacyclovir and Acyclovir for Suppression of Shedding of Herpes Simplex Virus in the Genital Tract," J. Infect. Dis., Oct. 2004, 190:1374-1381.
Hayouka et al., "Evidence for phenylalanine zipper-mediated dimerization in the X-ray crystal structure of a magainin 2 analogue," J. Am. Chem. Soc., 2013, 135(42):15738-15741.
Hillier et al., "Association between bacterial vaginosis and preterm delivery of a low-birth-weight infant," The Vaginal Infections and Prematurity Study Group, N. Engl. J. Med., Dec. 1995, 333(26):1737-1742.
Horne et al., "Sequence-based design of alpha/beta-peptide foldamers that mimic BH3 domains," Angew Chem Int Ed Engl., 2008, 47(15):2853-6.
Imura et al., "Magainin 2 in action: distinct modes of membrane permeabilization in living bacterial and mammalian cells," Biophys. J, 2008, 95:5757-5765.
Invenio.nusl.cz, [online], "Design of stable antimicrobial peptides through hydrocarbon stapling," 2011, retrieved on Feb. 4, 2021, retrieved from URL<http://invenio.nusl.cz/record/80987>, 1 page.
Kemp et al., "The Structure and Energetics of Helix Formation by Short Templated Peptides in Aqueous Solution. 2. Characterization of the Helical Structure of Ac-Hel1-Ala6-OH," J. Am. Chem. Soc., 1996, 118(18):4240-4248.
Lee et al., "Helical antimicrobial peptides assemble into protofibril scaffolds that present ordered dsDNA to TLR9," Nature Communications, 2019, 10:1012, 10 pages.

(56) References Cited

OTHER PUBLICATIONS

Lehmann et al., "Antitumor activity of the antimicrobial peptide magainin II against bladder cancer cell lines," Eur Urol., Jul. 2006, 50(1):141-7.

Li et al., "Comparative immunogenicities of Vi polysaccharide-protein conjugates composed of cholera toxin or its B subunit as a carrier bound to high- or lower-molecular-weight Vi," Infect. Immun., Dec. 1989, 57(12):3823-3827.

Li et al., "The landscape of cancer cell line metabolism," Nature Medicine, 2019, 25(5):850-860.

Ling et al., "More than fishing for a cure: The promises and pitfalls of high throughput cancer cell line screens, " Pharmacology & Therapeutics, 2018, 191:178-189.

Madden et al., "Facile synthesis of stapled, structurally reinforced peptide helices via a photoinduced intramolecular 1,3-dipolar cycloaddition reaction," Chem Commun (Camb), 2009, 37:5588-5590.

McFarland et al., "Multiplexed single-cell transcriptional response profiling to define cancer vulnerabilities and therapeutic mechanism of action," Nature Communications, 2020, 11(1):4296, 15 pages.

Mourtada et al., "Design of stapled antimicrobial peptides that are stable, nontoxic and kill antibiotic-resistant bacteria in mice," Nature Biotechnology, 2019, 37(10):1186-1197.

Oberlick et al., "Small-Molecule and CRISPR Screening Converge to Reveal Receptor Tyrosine Kinase Dependencies in Pediatric Rhabdoid Tumors," Cell Reports, 2019, 28(9):2331-2344.

Orner et al., "Toward proteomimetics: terphenyl derivatives as structural and functional mimics of extended regions of an alpha-helix," J. Am. Chem. Soc, 2001, 123(22):5382-3.

Park et al., "A Novel Antimicrobial Peptide from Bufo bufo gargarizans," BBRC, 1996, 218:408-413.

PCT International Search Report and Written Opinion in International Appln. No. PCT/US2020/065078, dated Mar. 2, 2021, 17 pages.

Sancar-Bas et al., "Esculentin-2PLa, a frog skin antimicrobial peptide, causes necrotic cell death in breast cancer cell lines," EACR24 Poster Sessions, European Journal of Cancer, 2016, 61(Suppl. 1):S132-S133.

Schauer et al., "Selective USP7 inhibition elicits cancer cell killing through a p53-dependent mechanism," Scientific Reports, 2020, 10:5324, 15 pages.

Tsvetkov et al., "Mitochondrial metabolism promotes adaptation to proteotoxic stress," Nat Chem Biol., 2019, 15(7):681-689.

Yu et al., "High-throughput identification of genotype-specific cancer vulnerabilities in mixtures of barcoded tumor cell lines," Nat. Biotechnol., 2016, 34(4):419-423.

U.S. Appl. No. 15/201,235, U.S. Pat. No. 10,464,975, 2017/0015716, filed Jul. 1, 2016, Walensky.

U.S. Appl. No. 16/551,102, 2020/0231638, filed Aug. 26, 2019, Walensky.

U.S. Appl. No. 15/445,502, 2017/0247423, filed Feb. 28, 2017, Walensky.

U.S. Appl. No. 16/631,315, 2020/0207821, filed Jan. 15, 2020, Walensky.

* cited by examiner

| | |
|---|---|
| BFStap(i+4)1 | TRSSRAGLQWPVGRVHXLLRX |
| BFStap(i+4)2 | TRSSRAGLQWPVGRVXRLLXK |
| BFStap(i+4)3 | TRSSRAGLQWPVGRXHRLXRK |
| BFStap(i+4)4 | TRSSRAGLQWPVGXVHRXLRK |
| BFStap(i+4)5 | TRSSRAGLQWPVXRVHXLLRK |
| BFStap(i+4)6 | TRSSRAGLQWPXGRVXRLLRK |
| BFStap(i+4)7 | TRSSRAGLXWPVXRVHRLLRK |
| BFStap(i+4)8 | TRSSRAGXQWPXGRVHRLLRK |
| BFStap(i+4)9 | TRSSXAGLXWPVGRVHRLLRK |
| BFStap(i+4)10 | TRSXRAGXQWPVGRVHRLLRK |
| BFStap(i+4)11 | TRXSRAXLQWPVGRVHRLLRK |
| BFStap(i+4)12 | TXSSRXGLQWPVGRVHRLLRK |
| BFStap(i+4)13 | XRSSXAGLQWPVGRVHRLLRK |
| BFStap(i+7)1 | TRSSRAGLQWPVGSVHRLLRX |
| BFStap(i+7)2 | TRSSRAGLQWPVSRVHRLLXK |
| BFStap(i+7)3 | TRSSRAGLQWPSGRVHRLXRK |
| BFStap(i+7)4 | TRSSRAGLSWPVGRVXRLLRK |
| BFStap(i+7)5 | TRSSRAGSQWPVGRXHRLLRK |
| BFStap(i+7)6 | TRSSRASLQWPVGXVHRLLRK |
| BFStap(i+7)7 | TRSSRSGLQWPVXRVHRLLRK |
| BFStap(i+7)8 | TRSSSAGLQWPXGRVHRLLRK |
| BFStap(i+7)9 | TSSSRAGLXWPVGRVHRLLRK |
| BFStap(i+7)10 | SRSSRAGXQWPVGRVHRLLRK |
| BuforinII(F10W) | TRSSRAGLQWPVGRVHRLLRK |
| BuforinII | TRSSRAGLQFPVGRVHRLLRK |

FIG. 1

A
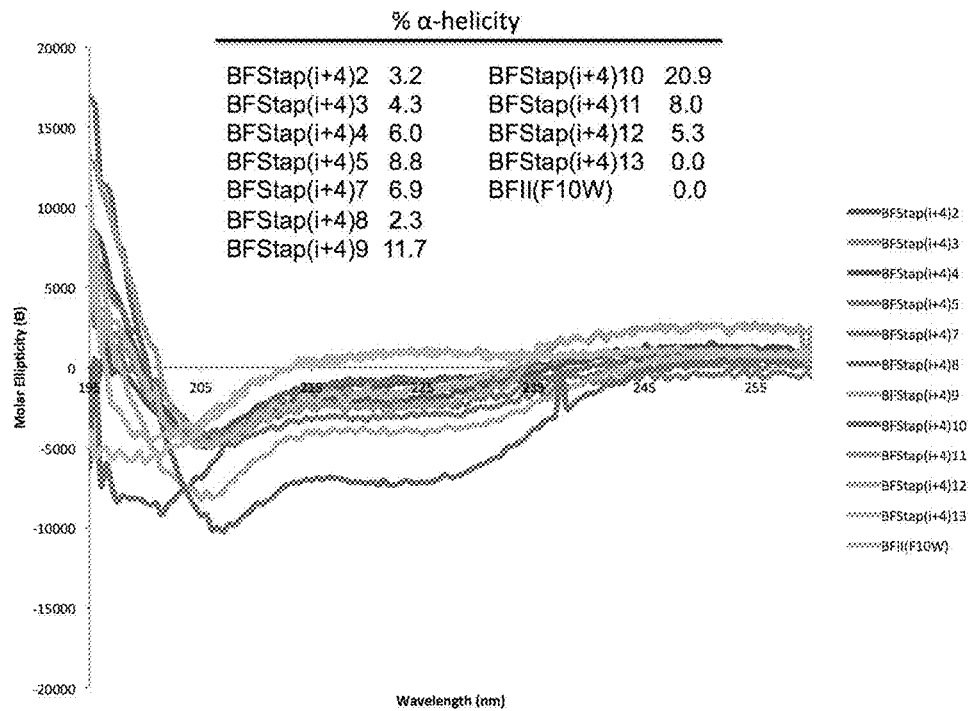
B
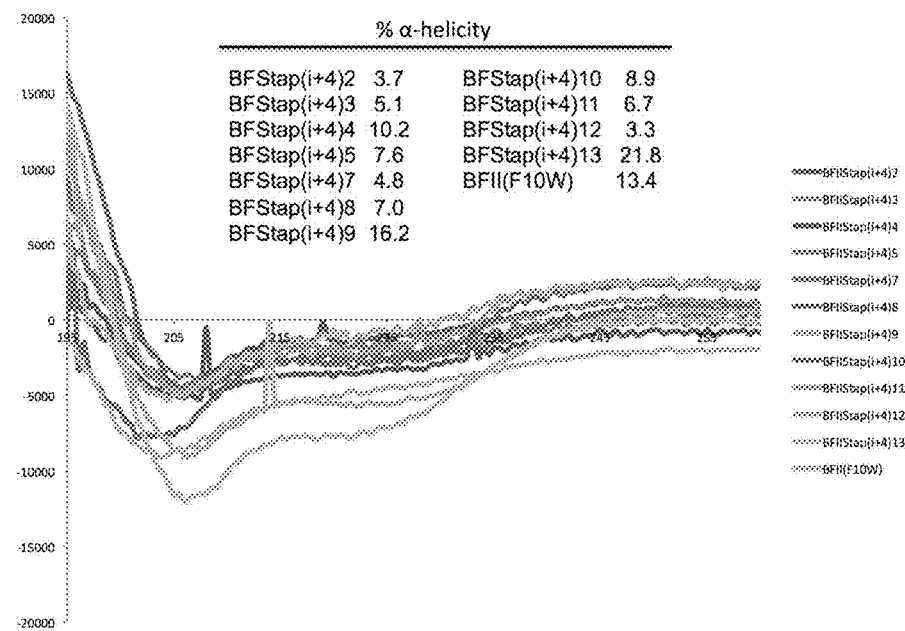
FIG. 2

A
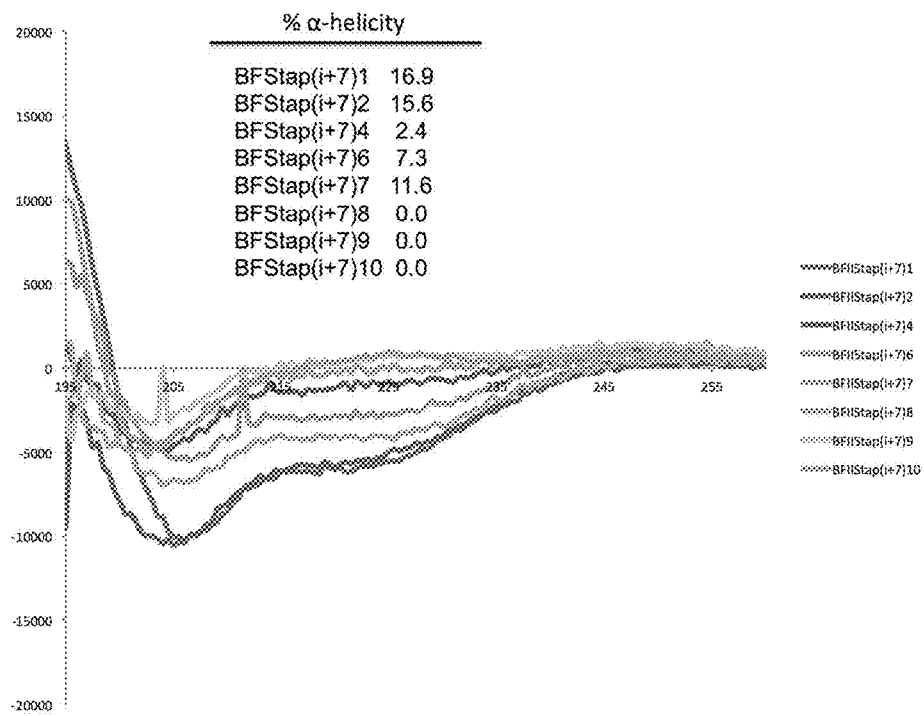
B
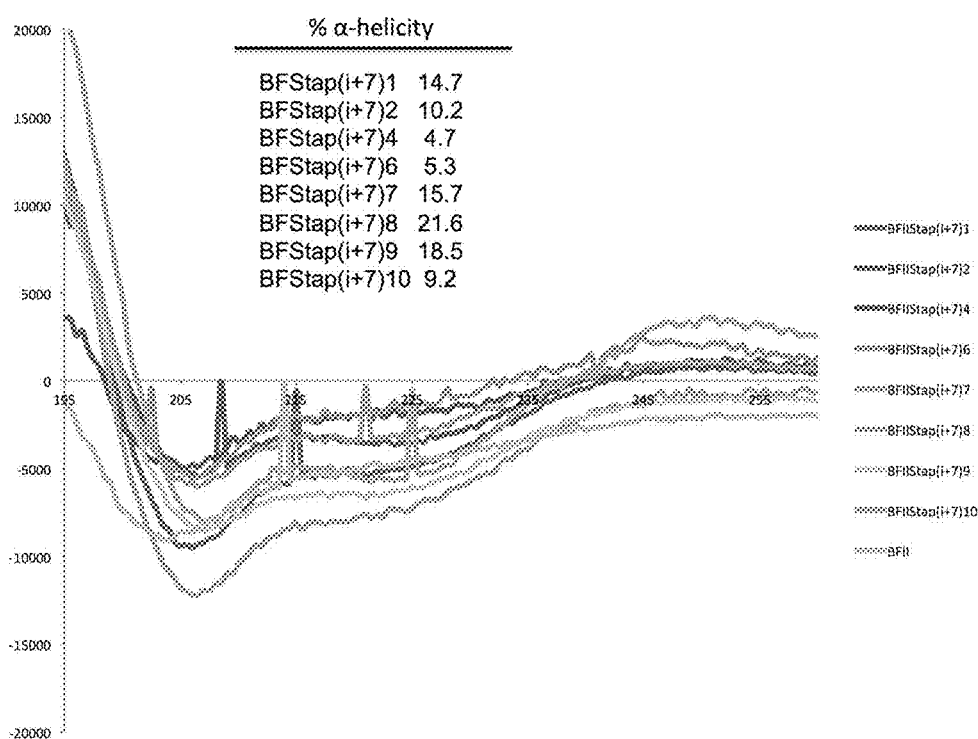
FIG. 3

STAPLED INTRACELLULAR-TARGETING ANTIMICROBIAL PEPTIDES TO TREAT INFECTION

CROSS REFERENCE TO RELATED APPLICATIONS

This application is a continuation application of U.S. patent application Ser. No. 15/445,502, filed Feb. 28, 2017, which claims the benefit of U.S. Provisional Application No. 62/301,426, filed Feb. 29, 2016, each of which is incorporated herein by reference in its entirety.

SEQUENCE LISTING

The instant application contains a Sequence Listing which has been submitted electronically in ASCII format and is hereby incorporated by reference in its entirety. Said ASCII copy, created on Mar. 9, 2020, is named "00530-0329002SequenceListing.txt" and is 35,013 bytes in size.

TECHNICAL FIELD

This disclosure relates to structural stabilization of intracellular-targeting antimicrobial peptides and methods for using such peptides to treat bacterial and other pathogenic infections.

BACKGROUND OF THE INVENTION

The rise of antibiotic superbugs is a major threat to healthcare systems around the globe. In the United States alone, the Centers for Disease Control and Prevention (CDC) estimates that healthcare costs due to antibiotic-resistant infections amount to $20 billion per year [1]. With the antibiotic pipeline drying up over the past decade, there are very few drug candidates to restock our antibiotic arsenal to address resistant infections [2-4]. In addition, due to the regulatory hurdles and low financial incentive for pharmaceutical and biotechnology companies to invest in antibiotic research, the burden of antibiotic discovery has fallen to academic research centers and hospitals [5-6]. These events have led to new government initiatives, such as the U.S. Generating Antibiotic Incentives Act and the Innovative Medicines Initiative New Drugs for Bad Bugs, which would introduce larger financial incentives for companies to develop novel agents, and would fast-track the drug approval process of potential antibiotic candidates [2]. Furthermore, the Obama administration recently allotted $1.2 billion dollars to investment in increased surveillance for antibiotic resistance outbreaks and antibiotic drug discovery.

Though such initiatives are important steps in the right direction, the need for innovation in antibiotic discovery technologies is crucial for restocking the drug pipeline with new candidates. Traditional drug discovery technologies have served us well this far; however, as bacterial resistance has evolved over time, these technologies have become increasingly obsolete. Alternative treatment options, such as bacteriophage therapy and vaccinations, are currently being heavily pursued and could help alleviate the burden of antibiotic resistance and even reduce its prevalence [7-10]. Nonetheless, much development and research needs to be done before such therapeutics could reach the bedside of patients who need novel antibiotics urgently. While other treatment options are being researched and advanced, antibiotics are the most effective and reliable therapeutic modality available for microbial infections. Thus, their continued development is of crucial importance, as is the need for new reservoirs of natural compounds from which candidates can be developed. One potential reservoir is a cohort of compounds called antimicrobial peptides (AMPs).

AMPs are an evolutionarily conserved class of proteins that form an essential line of defense (in particular, as a key component of the humoral immune response) against microbial invasion [2]. These peptides are produced by many disparate organisms and have been found to exhibit a wide spectrum of activity against bacteria, fungi, protozoa, and even viruses.

AMPs can be divided into four main structural groups: stabilized β-sheet peptides with two to four disulfide bridges; loop peptides with a single disulfide bridge; α-helical peptides; and extended structures rich in arginine, glycine, proline, tryptophan, and histidine [2-4]. Typically 12 to 50 amino acids in length, these peptides are usually cationic with amphipathic character. These biophysical properties allow them to interact with bacterial membranes resulting in either disruption of membrane integrity or translocation and disruption of intracellular processes [3-5]. Other properties of AMPs include immune system modulation through various mechanisms such as increasing the production of cytokines, activating immune cells, and expediting wound healing [6,7].

While much focus has been levied onto certain α-helical AMPs due to their membrane lytic properties and the vast amount of structural and mechanistic data available, other families of AMPs have remained much less studied and characterized. These less-characterized AMPs include a group of AMPs known as intracellular-targeting antimicrobial peptides (I-TAMPs). Due to their ability to translocate across membranes, this class of AMPs can target various microbial processes inside the microbial cell, including inhibition of DNA synthesis, protein synthesis, chaperone-assisted protein folding, enzymatic activity, and/or cell wall synthesis [3,8]. I-TAMPs have been discovered in fish, mollusks, insects, amphibians and mammals [3,9]. However, it has been difficult to characterize these AMPs properly, since at high concentrations, most AMPs become lytic and current model membrane systems are too simplistic [8].

Nevertheless, there are certain intracellular-targeting antimicrobial peptides that have been well-studied, and consensus has been reached with regard to their mode of action. One such peptide is buforin II, a histone-derived AMP (H-DAMP), which was isolated from the stomach tissue of the Asian toad, *Bufo bufo garagriozans* [13]. Unlike other amphibian AMPs like magainin II, buforin II does not disrupt the integrity of bacterial membranes. Instead, buforin II translocates into the bacterial cytosol, where it is able to bind to DNA and inhibit transcription [10]. Nevertheless, the generally poor stability and low potency of I-TAMPs, including buforin II, have reduced interest in further development of buforin II and/or other I-TAMPs as active pharmaceutical agents and have led to their being generally relegated to use as research reagents.

SUMMARY

This document describes the installation of all-hydrocarbon staple(s) into I-TAMP sequences, yielding compounds with enhanced antimicrobial activity yet little to no off-target toxicity. Hydrocarbon stapling of peptides recapitulates the α-helical secondary structure of a critical subcomponent of I-TAMPs and thereby enhances their import into bacteria and, consequently, their biological activity inside the bacterial cell [14,15]. In addition to improved α-helical stabilization, hydrocarbon stapling enhances proteolytic resistance, thereby conferring improved pharmacokinetic properties relative to natural peptides, which are often susceptible to rapid degradation in vivo [16]. Moreover, the stapled I-TAMPs of this document can, in some embodiments, have no or minimal lytic or cell growth-inhibiting activity against target microbial cells. This disclosure shows that applying hydrocarbon stapling to discrete sequences within I-TAMPs results in structural stabilization, enhanced antimicrobial activity, and significantly lowered hemolytic activity.

More specifically, the document provides an internally cross-linked (ICL) intra-microbial cell targeting anti-microbial peptide (I-TAMP) having the Formula (I),

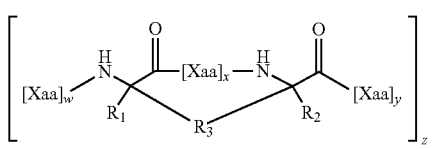

Formula (I)

or a pharmaceutically acceptable salt thereof,
wherein;
each Xaa is independently an amino acid;
each $R_1$ and $R_2$ is independently H, alkyl, alkenyl, alkynyl, arylalkyl, cycloalkylalkyl, heteroarylalkyl, or heterocyclylalkyl, any of which is substituted or unsubstituted;
each $R_3$ is independently alkylene, alkenylene, or alkynylene, any of which is substituted or unsubstituted;
each $R_4$ is independently —$NH_3$ or —OH, wherein each —$NH_3$ is optionally coupled with another chemical entity;
each x is independently 1, 2, 3, 4, 5, 6, 7, 8, 9, or 10;
each w and y is independently 1, 2, 3, 4, 5, 6, 7, 8, 9, 10, 11, 12, 13, 14, 15, 16, 17, 18, 19, or 20; and
z is 1, 2, 3, 4, 5, 6, 7, 8, 9, or 10,
wherein the peptide exhibits an intracellular antimicrobial effect against at least one microbe.

In some embodiments:
each $R_1$ and $R_2$ are independently H or a $C_1$ to $C_{10}$ alkyl, alkenyl, alkynyl, or;
each $R_3$ is alkylene, alkenylene or alkynylene (e.g., a $C_8$ or $C_{11}$ alkenylene) substituted with 1-6 $R_4$;
each $R_4$ is, independently —$NH_3$ or —OH, wherein each —$NH_3$ is optionally coupled with a chemical entity such as benzylic acid derivatives, enzyme inhibitors, a carbohydrate group, a hydroxyl group, a phosphate group, a farnesyl group, an isofarnesyl group, a fatty acid group, or a linker for conjugation or functionalization;
x is 2, 3, or 6, $R_3$ replacing, relative to the corresponding parent non-internally cross-linked AMP, the side chains of at least one pair of amino acids;
w and y are independently an integer from 0-20;
z is an integer from 1-10 (e.g., 1, 2, 3, 4, 5, 6, 7, 8, 9, 10); and
each Xaa is independently an amino acid (e.g., one of the 20 naturally occurring amino acids or any non-naturally occurring amino acid),
provided that: when x is 2, $R_3$ is $C_8$ alkylene, alkenylene, or alkynylene; when x is 3, $R_3$ is $C_8$ alkylene, alkenylene, or alkynylene; and when x is 6, $R_3$ is $C_{11}$ alkylene, alkenylene, or alkynylene and provided that the sum of x, w, and y is at least 10, and such that the ICL I-TAMP contains at least 10 contiguous amino acids of any one of SEQ ID NOs: 1-13 or a variant thereof having 1, 2, 3, 4, or 5 amino acid substitutions, or another polypeptide sequence described herein except that: (a) within the 10 contiguous amino acids the side chains of at least one pair (e.g., one or two pairs) of amino acids separated by 2, 3, or 6 amino acids are replaced, relative to the corresponding parent non-internally cross-linked AMP, by the linking group, $R_3$, which connects the alpha carbons of the pair of amino acids as depicted in Formula I; and (b) the alpha carbon of the first of the pair of amino acids is substituted with $R_1$ as depicted in Formula I and the alpha carbon of the second of the pair of amino acids is substituted with $R_2$ as depicted in Formula I. $R_3$ can be substituted with two $R_4$ and the $R_4$ can be —OH. Alternatively, $R_3$ can be an optionally substituted —$NH_3$ and the other is —OH.

Moreover, the document additionally provides an internally cross-linked (ICL) intra-microbial cell targeting antimicrobial peptide (I-TAMP) containing amino acids, the side chains of at least one pair (e.g., one or two pairs) of amino acids separated by 2, 3, or 6 amino acids being replaced, relative to the corresponding parent non-internally cross-linked AMP, by the linking group, $R_3$, which connects the alpha carbons of the pair of amino acids such that:
each $R_3$ is independently alkylene, alkenylene, or alkynylene (e.g., a $C_6$, $C_7$, or $C_{11}$ alkenylene) optionally substituted with 1-6 $R_4$;
each $R_4$ is independently —$NH_3$ or —OH, wherein each —$NH_3$ is optionally substituted; and each $R_1$ and $R_2$ is independently $C_1$ to $C_{10}$ alkyl, alkenyl, alkynyl, arylalkyl, cycloalkylalkyl, heteroarylalkyl, or heterocyclylalkyl, any of which is substituted or unsubstituted.

In some embodiments, the ICL I-TAMP contains at least 10 contiguous amino acids of any of SEQ ID NOs: 1-13 or a variant thereof having 1, 2, 3, 4, or 5 amino acid substitutions, or another polypeptide sequence described herein except that: (a) within the 10 contiguous amino acids the side chains of at least one pair (e.g., one or two pairs) of amino acids separated by 2, 3, or 6 amino acids are replaced, relative to the corresponding parent non-internally cross-linked AMP, by the linking group, $R_3$, which connects the alpha carbons of the pair of amino acids and the H of the alpha carbon of each pair of amino acids having their side chains replaced by linking group $R_3$ is optionally, independently replaced by a $C_1$ to $C_{10}$ alkyl, alkenyl, or alkynyl. This peptide can contain at least 10 contiguous amino acids of SEQ ID NO: 7.

Either of the above-described ICL I-TAMPs can contain the sequence of any one of SEQ ID NOs: 14-60. They can, for example, contain the sequence of BFStap(i+4)2, BFStap(i+4)3, BFStap(i+4)4, BFStap(i+4)6, BFStap(i+4)7, BFStap(i+4)8, BFStap(i+4)11, BFStap(i+7)1, BFStap(i+7)2, BFStap(i+7)3, BFStap(i+7)4, BFStap(i+7)5, BFStap(i+7)6, BFStap(i+7)7, BFStap(i+7)8, or BFStap(i+7)9. In certain instances, the above-described ICL I-TAMPs can contain the sequence of any one of SEQ ID NOs: 43, 47, or 55.

The document also features a method of treating or preventing a microbial infection, the method including administering an effective amount of any of the ICL I-TAMPs described above to a subject having, or at risk of having, an infection with a microbial organism. The subject can be an animal or plant. The animal can be a mammal, e.g., a human. The microbial organism can be a bacterial organism, e.g., a gram-positive bacterial organism or a Gram-negative bacterial organism. The method can further include administering an effective amount of at least one antibiotic. The antibiotic can act synergistically with the ICL I-TAMP to inhibit or prevent infection with the microbial organism. The ICL I-TAMP and the antibiotic can act synergistically to overcome or prevent resistance to the antibiotic.

Another aspect of the document is a composition containing one or more of the any of the ICL I-TAMPs described above. The composition can further contain a medical or hygienic device. The one or more ICL I-TAMPs can be coated onto or impregnated into the medical or hygienic device. The composition can also contain one or more antibiotics.

Also provided by the document is a method of inhibiting the growth of, or killing, a microbial organism that involves contacting the microbial organism with one or more of any of the above-described ICL I-TAMPS. The microbial organism can be an extracellular microbial organism or an intracellular microbial organism. The contacting can occur in a subject comprising the microbial organism. Alternatively, the method can be an in vitro method. It is understood that the method can be implemented using any of the features described in the document (e.g., those described above for a method of treating or preventing a microbial infection).

Another feature of the document is a method of making any of the above-described ICL I-TAMPs, the method involving: synthesizing the ICL I-TAMP such that the ICL I-TAMP comprises an α-helical region comprising a first surface hydrophobic patch, the replacement with the linking groups maintaining or resulting in, relative to the corresponding parent non-internally crosslinked I-TAMP, discontinuity between the first hydrophobic patch and one or more additional surface hydrophobic patches on internally crosslinked peptide. The method can further include adding to the linking group a hydrolyzing modification, e.g., dihydroxylation.

Yet another feature of the document is a method of designing the any of the above-described ICL I-TAMPs, involving:

creating one or more panels of ICL I-TAMPs, each panel containing a plurality of panel member ICL I-TAMPs in each of which: (a) the side chains of at least one pair of amino acids separated by 2, 3, or 6 amino acids are replaced by the linking group, $R_3$, which connects the alpha carbons of the pair of amino acids; and (b) in each member of each panel, the pair of amino acids is at different positions as compared to the other members of the relevant panel; and testing each member of all panels for (i) the presence of discontinuity between a first surface hydrophobic patch in an α-helical region of the relevant member and one or more additional surface hydrophobic patches on the α-helical region of the member; and (ii) the ability of each member of each panel for its ability to translocate into a microbial cell and lyse or inhibit the growth of a mammalian cell. The method can further involve manufacturing one or members of all the panels that have a relatively high ability to translocate into a microbial cell and/or a relatively low ability to lyse or inhibit the growth of a mammalian cell.

As used herein, the terms "about" and "approximately" are defined as being within plus or minus 10% of a given value or state, preferably within plus or minus 5% of said value or state.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

BRIEF DESCRIPTION OF THE DRAWINGS

FIG. 1 is a chart showing the sequences of buforin II and exemplary stapled analogues. Buforin II sequence aligned with the sequences of stapled derivatives demonstrate the position of the i, i+4 staple, which is represented by the pair: X,X, and the i, i+7 staple, which is represented by the pair: 8,X. Other residues that were mutated are boxed. The sequences listed from top to bottom correspond to SEQ ID NOs.: 37 to 60 and 7. "8" is (R)-2-(7'-octenyl)alanine; and "X" is (S)-2-(4'-pentenyl)alanine.

FIG. 2 shows the circular dichroism (CD) spectra of buforin II and i, i+4 stapled analogues in the absence and presence of trifluoroethanol (TFE). FIG. 2 PANEL A is a graph of a CD spectrum of buforin II (F10W) and i, i+4 stapled analogues in buffer solution. FIG. 2 PANEL B is a graph of a CD spectrum of buforin II (F10W) and i, i+4 stapled analogues in TFE:buffer (1:1) mixture.

FIG. 3 shows the circular dichroism spectra of buforin II and i, i+7 stapled analogues in the absence and presence of trifluoroethanol (TFE). FIG. 3 PANEL A is a graph of a CD spectrum of buforin II (F10W) and i, i+7 stapled analogues in buffer solution. FIG. 3 PANEL B is a graph of a CD spectrum of buforin II (F10W) and i, i+7 stapled analogues in TFE:buffer (1:1) mixture.

FIG. 4 PANEL B illustrates peptides with staples of various lengths. FIG. 4 PANEL C illustrates a staple walk along a peptide sequence.

DETAILED DESCRIPTION

Figure 4:
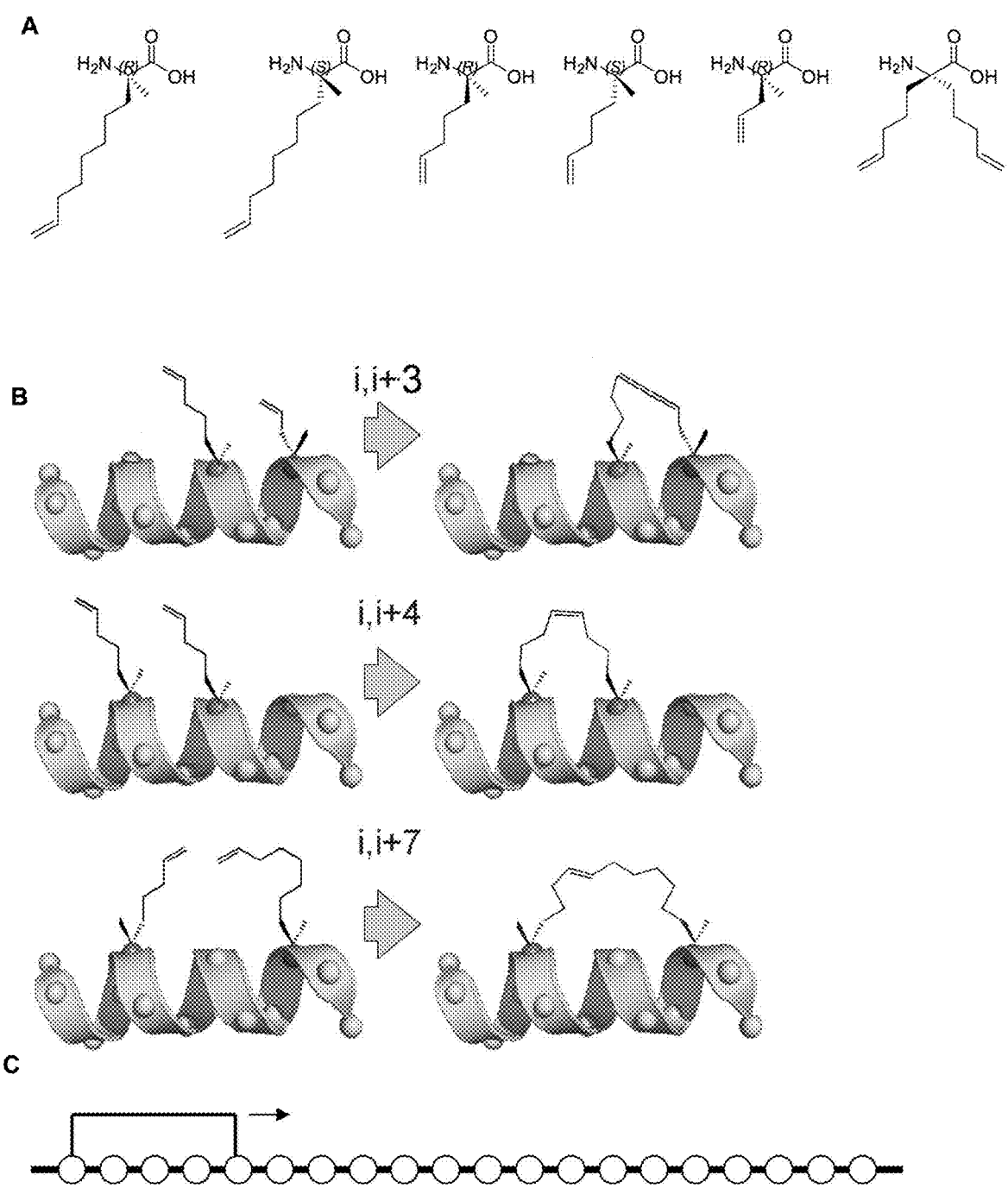
FIG. 4 PANEL A shows the chemical structures of the unnatural amino acids used to generate various kinds of staples.

I-TAMP sequences possess the unique property of microbial cell translocation to achieve their anti-microbial activity inside the microbial cell. This disclosure informs the development of structurally-stabilized I-TAMPs to optimize/maximize their antimicrobial potency and proteolytic stability for therapeutic development. It will be appreciated that such structurally stabilized I-TAMPs should have no or minimal lytic or cell growth-inhibiting activity against target microbial cells. Such drug repurposing is another critically important avenue for transforming FDA-approved agents, such as methotrexate, into selective antimicrobials. Thus, this invention addresses the previous limitations in developing I-TAMPs as antimicrobial agents by chemically-stabilizing I-TAMP structures and also adapting them for bacterial delivery of therapeutic cargos.

As a proof of concept, we applied hydrocarbon stapling to the sequence of buforin II. By installing hydrocarbon staple(s) at specific locations within the buforin II sequence, we achieved dramatic increases in potency, including, e.g., a 200-fold increase in antimicrobial activity compared to the unmodified (parent) buforin II sequence. These enhancements in potency were accompanied by structural stabilization as determined by circular dichroism spectroscopy.

Moreover, these increases in activity were not necessarily accompanied by increases in non-specific hemolytic activity against human red blood cells. For example, in certain examples, hemolytic activity was identified only at concentrations 10 times greater than the minimum inhibitory concentration (MIC) for bacterial treatment, highlighting a significant, wide therapeutic window.

Importantly, the mechanism of action of buforin II involving bacterial membrane transit, enables the development of chimeric compounds that link buforin II to antibiotics, which are otherwise incapable of accessing the interior of Gram-negative bacteria. Moreover, the specific stapling strategy discovered for I-TAMPs reinforces both the bacterial uptake capacity of this AMP and the stability of the peptide for in vivo applications.

The invention further provides novel opportunities to harness the potential of intracellular AMPs to enable new therapeutics for overcoming treatment resistance. Since I-TAMPs like buforin II act on bacterial intracellular targets by translocating across their membranes, stapled I-TAMPs provide a new delivery platform for selective targeting of bacteria, enabling repurposing of previously ineffective antibiotics due to bacterial membrane impenetrance. An exemplary class of cargo is Gram-positive antimicrobials, e.g., beta-lactam drugs, which are otherwise blocked by the outer membrane of Gram-negative bacteria. Additional classes of cargo include, e.g., antibiotics that are otherwise toxic for human use but could be selectively targeted to bacteria, and cancer therapeutics that have bacterial cross-targets, e.g., methotrexate [19].

I-TAMPs from Fish

The principles and methods of the invention apply to all I-TAMPs that function as antimicrobials in fish (including, e.g., in skin and/or intestinal secretions) and stapled analogs thereof. As examples of this application, the following sequences and exemplary stapled analogs are listed below. In these sequences and all the others listed below, "X" indicates the position of staples. Some of the sequences contain an "—NH$_2$ at the C-terminus; this indicates amidation of the C-terminal residue.

```
Pleurocidin (From winter flounder)
                                             (SEQ ID NO: 1)
GWGSFFKKAAHVGKHVGKAALTHYL-NH2

(SEQ ID NO: 14)
GWXSFFXKAAHXGKHXGKAALTHYL-NH2

(SEQ ID NO: 15)
GWGSFFKKXAHVXKHVGKXALTXYL-NH2

Hipposin (From Atlantic halibut)
                                             (SEQ ID NO: 2)
SGRGKTGGKARAKAKTRSSRAGLQFPVGRVHRLLRKGN

YAHRVGAGAPVYL (SEQ ID NO: 16)
SGRXKTGGKAXAKAKTRSSRAGLQFPVGRVHRLLRKGN

YAHRVGAGAPVYL (SEQ ID NO: 17)
SGRGKTGGKXRAKXKTRSSRAGLQFPXGRVXRLLRKGN

YAHRVGAGAPVYL

Himanturin (From the Round Whip Ray,
H. pastinacoides)
                                             (SEQ ID NO: 3)
KAKSRSSRAGLQFPVGRVHRLLRKGNYAERVGAGAPVYL (SEQ ID NO: 18)
KAKSRXSRAXLQFPVGRVHRLLRKGNYAXRVGAGAXVYL (SEQ ID NO: 19)
KAKSRSSRAGLXFPVXRVHRLLRKGNYXERVGAGXPVYL Rainbow Trout FI2A (From Oncorhynchus mykiss)
                                             (SEQ ID NO: 4)
SGRGKTGGKARAKAKTRSSRAGLQFPVGRVHRLLRKGNY

AERVGAGAPVYL (SEQ ID NO: 20)
SGRGKTGGKARAKAKTRSSXAGLQFPXGRVHRLLRXGNY

AERXGAGAPVYL (SEQ ID NO: 21)
SGRGKTGGKXRAKAKTXSSRAGLQFPVGRVHRLXRKGNY

AXRVGAGAPVYL
```

I-TAMPs from Mollusks

The principles and methods of the invention apply to all I-TAMPs that function as antimicrobials in mollusks (including, e.g., in skin and/or intestinal secretions) and the stapled analogs thereof. As examples of this application, the following sequences and exemplary stapled analogs are listed below:

```
Abhisin (From Haliotis discus)
                                             (SEQ ID NO: 5)
MSGRGKGGKTKAKAKSRSSRAGLQFPVGRIHRLLRKGNYA (SEQ ID NO: 22)
MSGRGKGXKTKAKAXSRSSRAGLQFPVGRIHRLLRKGNYA (SEQ ID NO: 23)
MSGRGKGGKTKAKAKSRSSRAGLQFPXGRIHRLXRKGNYA Scallop AMP (From Chlamys farreri)
                                             (SEQ ID NO: 6)
MSGRGKGGKVKGKAKSRSSRAGLQFPVGRIHRLLRKGNYA (SEQ ID NO: 24)
XSGRGKGXKVKGKAKSRSSRAGLQFPVGRIHRLLRKGNYA (SEQ ID NO: 25)
MSGRGKGGKVKGKXKSRSSRXGLQFPVGRIHRLLRKGNYA
```

I-TAMPs from Amphibians

The principles and methods of the invention apply to all I-TAMPs that function as antimicrobials in amphibians (including, e.g., in secretions) and stapled analogs thereof.

As examples of this application, the following sequences and exemplary stapled analogs are listed below:

```
Buforin (Stomach Secretion from Asian Toad
Bufo garagrizans-Example below is Buforin II)
                                    (SEQ ID NO: 7)
TRSSRAGLQFPVGRVHRLLRK (SEQ ID NO: 26)
TRSSRAGLQFPXGRXHRLLRK (SEQ ID NO: 27)
TRSSRAGLQFPVGRXHRLXRK (SEQ ID NO: 28)
TRSSRAGLQFPXGRVHRLXRK
```

I-TAMPs from Mammals

The principles and methods of the invention apply to all I-TAMPs that function as antimicrobials in mammals (including, e.g., in secretions) and stapled analogs thereof. As examples of this application, the following sequences and exemplary stapled analogs are listed below:

```
Human Histone H1 truncated analogues
                                    (SEQ ID NO: 8)
KLNKKAASGE (SEQ ID NO: 9)
KLNKKAASGEAKPKA (SEQ ID NO: 10)
KAKSPKKAKA (SEQ ID NO: 29)
KXNKKXASGEAKPKA (SEQ ID NO: 30)
KAXSPKKAKX Histatin 5 (From Homo sapiens)
                                    (SEQ ID NO: 11)
DSHAKRKKGYKRKFHEKHHSHRGY (SEQ ID NO: 31)
DSHAXRKKGYKRXFHEKHHSHRGY (SEQ ID NO: 32)
DSXAKRXKGYKRKXHEKHEISXRGY
```

I-TAMPs from Insects

The principles and methods of the invention apply to all I-TAMPs that function as antimicrobials in Insects (including, e.g., in skin and/or intestinal secretions) and stapled analogs thereof. As examples of this application, the following sequences and exemplary stapled analogs are listed below:

```
Drosocin (From Drosophila)
                                    (SEQ ID NO: 12)
GKPRPYSPRP(T*)SHPRPIRV T*: Threonine is glycosylated
                                    (SEQ ID NO: 33)
XKPRPYSXRP(T*)SHPRPIRV (SEQ ID NO: 34)
GKPRPYXPRP(T*)SHXRPIRV Apidaecin IB (From honey bees)
                                    (SEQ ID NO: 13)
GNNRPVYIPQPRPPHPRL
```

```
                                    (SEQ ID NO: 35)
GNNRPXYIPQPRXPHPRL (SEQ ID NO: 36)
GNNXPVYXPQPRPPXPRX
```

The present disclosure provides structurally stabilized peptides related to anti-bacterial peptides (AMP) (referred to at times as stabilized α-helices of AMP or stabilized AMP or STAMP) comprising at least two modified amino acids joined by an internal (intramolecular) cross-link (or staple), wherein the at least two amino acids are separated by 2, 3, or 6 amino acids. Stabilized peptides herein include stapled peptides, including peptides having two staples and/or stitched peptides. The structurally stabilized peptide of this disclosure are generally derived from I-TAMPs.

For example, in some embodiments, the compound exhibits at least a 1.25, 1.5, 1.75 or 2-fold increase in α-helicity as determined by circular dichroism compared to a corresponding uncrosslinked peptide. In some embodiments, the compound can exhibit about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100% helicity.

Amino acids are the building blocks of the peptides herein. The term "amino acid" refers to a molecule containing both an amino group and a carboxyl group as well as a side chain. Amino acids suitable for inclusion in the peptides disclosed herein include, without limitation, natural alpha-amino acids such as D- and L-isomers of the 20 common naturally occurring alpha-amino acids found in peptides (e.g., Ala (A), Arg (R), Asn (N), Cys (C), Asp (D), Gln (Q), Glu (E), Gly (G), His (H), Ile (I), Leu (L), Lys (K), Met (M), Phe (F), Pro (P), Ser (S), Thr (T), Trp (W), Tyr (Y), and Val (V), unnatural alpha-amino acids (including, but not limited to α,α-disubstituted and N-alkylated amino acids), natural beta-amino acids (e.g., beta-alanine), and unnatural beta-amino acids. Amino acids used in the construction of peptides of the present invention can be prepared by organic synthesis, or obtained by other routes, such as, for example, degradation of or isolation from a natural source.

There are many known unnatural amino acids, any of which may be included in the peptides of the present invention. Some non-limiting examples of unnatural amino acids are 4-hydroxyproline, desmosine, gamma-aminobutyric acid, beta-cyanoalanine, norvaline, 4-(E)-butenyl-4 (R)-methyl-N-methyl-L-threonine, N-methyl-L-leucine, 1-amino-cyclopropanecarboxylic acid, 1-amino-2-phenyl-cyclopropanecarboxylic acid, 1-amino-cyclobutanecarboxylic acid, 4-amino-cyclopentenecarboxylic acid, 3-amino-cyclohexanecarboxylic acid, 4-piperidylacetic acid, 4-amino-1-methylpyrrole-2-carboxylic acid, 2,4-diaminobutyric acid, 2,3-diaminopropionic acid, 2,4-diaminobutyric acid, 2-aminoheptanedioic acid, 4-(aminomethyl)benzoic acid, 4-aminobenzoic acid, ortho-, meta- and/para-substituted phenylalanines (e.g., substituted with —C(=O)C$_6$H$_5$; —CF$_3$; —CN; -halo; —NO$_2$; CH$_3$), disubstituted phenylalanines, substituted tyrosines (e.g., further substituted with —C=O)C$_6$H$_5$; —CF$_3$; —CN; -halo; —NO$_2$; CH$_3$), and statine. Additionally, amino acids can be derivatized to include amino acid residues that are hydroxylated, phosphorylated, sulfonated, acylated, and glycosylated, to name a few.

A "peptide" or "polypeptide" comprises a polymer of amino acid residues linked together by peptide (amide) bonds. The terms, as used herein, refer to proteins, polypeptides, and peptides of any size, structure, or function.

Typically, a peptide or polypeptide will be at least three amino acids long. A peptide or polypeptide may refer to an individual protein or a collection of proteins. In some instances, peptides can include only natural amino acids, although non-natural amino acids (i.e., compounds that do not occur in nature but that can be incorporated into a polypeptide chain) and/or amino acid analogs as are known in the art may alternatively be employed. Also, one or more of the amino acids in a peptide or polypeptide may be modified, for example, by the addition of a chemical entity such as a carbohydrate group, a hydroxyl group, a phosphate group, a farnesyl group, an isofarnesyl group, a fatty acid group, a linker for conjugation, functionalization, or other modification, etc. A peptide or polypeptide may also be a single molecule or may be a multi-molecular complex, such as a protein. A peptide or polypeptide may be just a fragment of a naturally occurring protein or peptide. A peptide or polypeptide may be naturally occurring, recombinant, or synthetic, or any combination thereof. "Dipeptide" refers to two covalently linked amino acids.

In some instances, a peptide has or can be induced to have alpha helical secondary structure.

In some instances, a peptide is a modified peptide that includes 1, 2, 3, 4, or 5 amino acid substitutions (e.g., 1, 2, 3, 4, or 5 amino acids are replaced with A or 1, 2, 3, 4, or 5 amino acids are conservatively substituted).

In some instances, stabilized peptides can be produced from I-TAMPs having at least 80% (e.g., 80%, 85%, 90%, 95%, 98%, 99%, 99.5%, or 100%) identity to one of SEQ ID NOs: 1-13 or I-TAMPs that include one of SEQ ID NOs: 1-13 with one or more (e.g., 1, 2, 3, 4, 5, 6, 7, 8, 9, 10, 11, 12, 13, 14, 15, 16, 17, 18, preferably 1-2, 1-3, 1-4, or 1-5) conservative amino acid substitutions. In some instances, stabilized peptides can have at least 80% (e.g., 80%, 85%, 90%, 95%, 98%, 99%, 99.5%, or 100%) identity to one of SEQ ID NOs: 14-36 or can include one of SEQ ID NOs: 1-13 with one or more (e.g., 1, 2, 3, 4, 5, 6, 7, 8, 9, 10, 11, 12, 13, 14, 15, 16, 17, 18, for example, 1-2, 1-3, 1-4, or 1-5) conservative amino acid substitutions. In some cases, the stabilized peptide has the sequence of one of SEQ ID NOs: 1-13 with one or two staples (e.g., one staple between two amino acids separated by 2 or 3 (or 6) amino acids or two staples each between two amino acids that are separated by 2 or 3 (or 6) amino acids). In addition, 1, 2, 3, 4, or 5 of the amino acids (whose side chains are not replaced with a staple) in this stabilized peptide can be replaced by a conservative substitution or can be replaced by A. In some cases, the stabilized peptide has the sequence of one of SEQ ID NOs: 37-60. In another case, the stabilized peptide has the sequence of one of SEQ ID NOs: 43, 47, or 55.

In some instances, a "conservative amino acid substitution" can include substitutions in which one amino acid residue is replaced with another amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

Methods for determining percent identity between amino acid sequences are known in the art. For example, the sequences are aligned for optimal comparison purposes (e.g., gaps can be introduced in one or both of a first and a second amino acid or nucleic acid sequence for optimal alignment and non-homologous sequences can be disregarded for comparison purposes). The length of a reference sequence aligned for comparison purposes can be at least 30%, at least 40%, at least 50%, at least 60%, or at least 70%, 80%, 90%, or 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The determination of percent identity between two amino acid sequences can be accomplished using, for example, the BLAST 2.0 program. Sequence comparison is performed using an ungapped alignment and using the default parameters (Blossom 62 matrix, gap existence cost of 11, per residue gapped cost of 1, and a lambda ratio of 0.85). The mathematical algorithm used in BLAST programs is described in Altschul et al. (Nucleic Acids Res. 25:3389-3402, 1997).

As disclosed above, peptides herein include at least two modified amino acids that together form an internal (intramolecular) cross-link (or staple), wherein the at least two modified amino acids are separated by: (A) two amino acids (i.e., i, i+3), (B) three amino acid (i.e., i, i+4), or (C) six amino acids (i.e., i, i+7).

In the case of a cross-link between i and i+3 the cross-link can be, for example, a $C_7$ alkylene or alkenylene. In the case of a cross-link between i and i+4 the cross-link can be, for example, a $C_8$ alkylene or alkenylene. In the case of a cross-link between i and i+7 the cross-link can be, for example, a $C_{11}$, $C_{12}$, or $C_{13}$ alkylene or alkenylene. When the cross-link is an alkenylene, there can one or more double bonds.

In the case of a cross-link between i and i+3 the cross-link can be, for example, a $C_6$, $C_7$, or $C_8$ alkylene or alkenylene (e.g., a $C_6$ alkenylene having one double bond). In the case of a cross-link between i and i+4 the cross-link can be, for example, a $C_8$ alkylene or alkenylene. In the case of a cross-link between i and i+7 the cross-link can be, for example, a $C_{11}$, $C_{12}$, or $C_{13}$ alkylene or alkenylene (e.g., a $C_{11}$ alkenylene having one double bond). When the cross-link is alkenylene, there can be one or more double bonds. The cross-link can be optionally substituted with 1-5 substituents selected from —OH and —NH$_3$.

"Peptide stapling" is a term coined from a synthetic methodology wherein two olefin-containing side-chains (e.g., cross-linkable side chains) present in a polypeptide chain are covalently joined (e.g., "stapled together") using a ring-closing metathesis (RCM) reaction to form a cross-linked ring (Blackwell et al., J. Org. Chem., 66: 5291-5302, 2001; Angew et al., Chem. Int. Ed. 37:3281, 1994). As used herein, the term "peptide stapling" includes the joining of two (e.g., at least one pair of) double bond-containing side-chains, triple bond-containing side-chains, or double bond-containing and triple bond-containing side chain, which may be present in a polypeptide chain, using any number of reaction conditions and/or catalysts to facilitate such a reaction, to provide a singly "stapled" polypeptide. The term "multiply stapled" polypeptides refers to those polypeptides containing more than one individual staple, and may contain two, three, or more independent staples of various spacings and compositions. Additionally, the term "peptide stitching," as used herein, refers to multiple and tandem "stapling" events in a single polypeptide chain to provide a "stitched" (e.g., tandem or multiply stapled)

polypeptide, in which two staples, for example, are linked to a common residue. Peptide stitching is disclosed, e.g., in WO 2008121767 and in WO 2010/068684, which are both hereby incorporated by reference in their entireties. In some instances, staples, as used herein, can retain the unsaturated bond or can be reduced (e.g., as mentioned below in the stitching paragraph description).

While many peptide staples have all-hydrocarbon cross-links, other type of cross-links or staples can be used. For example, triazole-containing (e.g., 1, 4 triazole or 1, 5 triazole) crosslinks can be used (see, e.g., Kawamoto et al. 2012 Journal of Medicinal Chemistry 55:1137; WO 2010/060112).

Stapling of a peptide using all-hydrocarbon cross-link has been shown to help maintain its native conformation and/or secondary structure, particularly under physiologically relevant conditions (see, e.g., Schafmiester et al., J. Am. Chem. Soc., 122:5891-5892, 2000; Walensky et al., Science, 305: 1466-1470, 2004).

Stapling the polypeptide herein by an all-hydrocarbon crosslink predisposed to have an alpha-helical secondary structure can improve stability and various pharmacokinetic properties.

Stabilized peptides herein include at least two internally cross-linked or stapled amino acids, wherein the at least two amino acids are separated, for example, by two (i.e., i, i+3), three (i.e., i, i+4), or six (i.e., i, i+7) amino acids. While at least two amino acids are required to support an internal cross-link (e.g., a staple), additional pairs of internally cross-linked amino acids can be included in a peptide, e.g., to support additional internal cross-links (e.g., staples). For example, peptides can include 1, 2, 3, 4, 5, or more staples.

Figure 5:
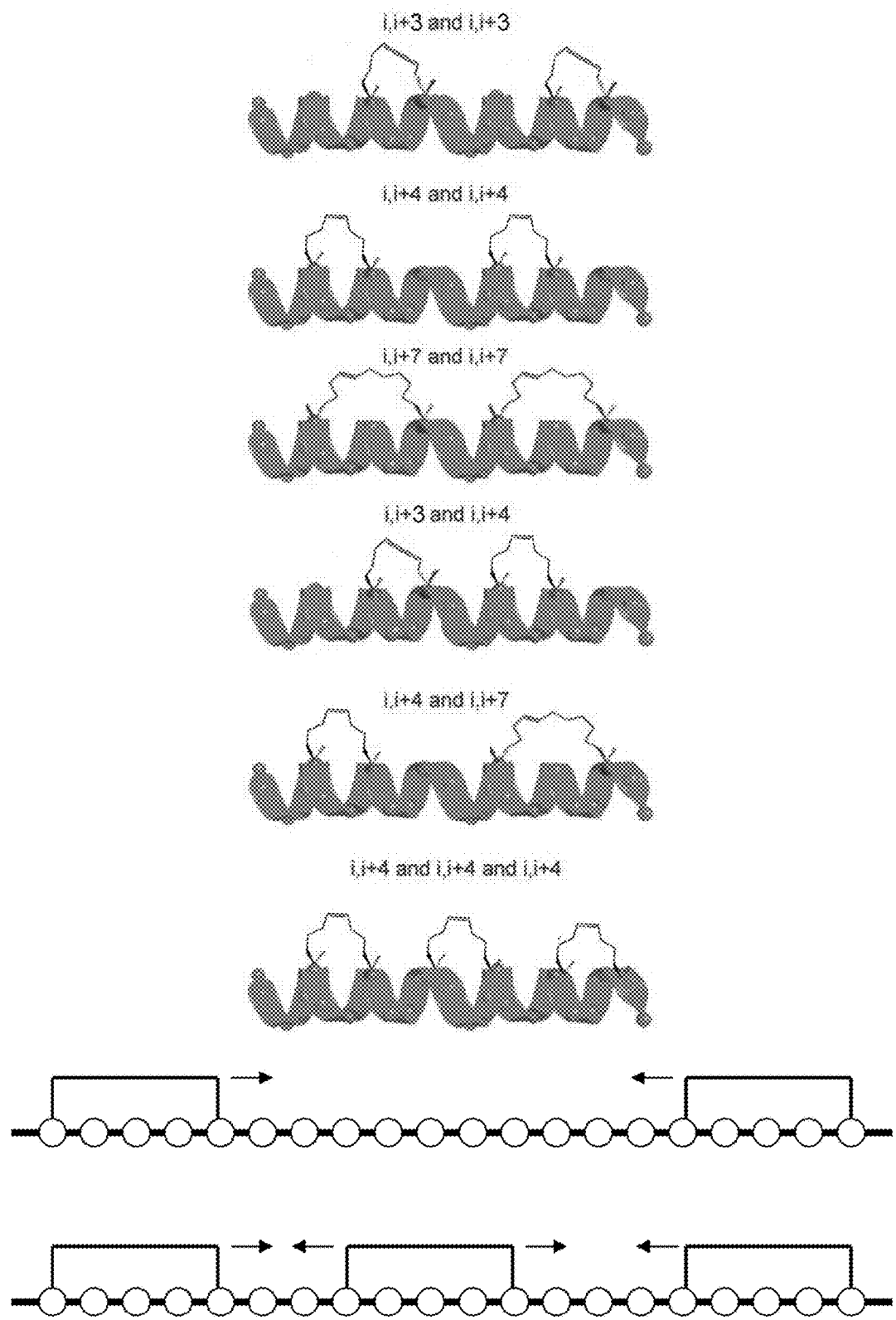
FIG. 5 is a schematic showing representations of various kinds of double and triple stapling strategies along with exemplary staple walks.

FIG. 4 PANEL A shows example chemical structures of unnatural amino acids that can be used to generate various crosslinked compounds. FIG. 4 PANEL B illustrates peptides with hydrocarbon crosslinks between i and i+3, i and i+4, and i and i+7 residues. FIG. 4 PANEL C illustrates a staple walk along a peptide sequence. FIG. 5 illustrates various peptide sequences with double and triple stapling strategies, and exemplary staple walks.

Alternatively or in addition, peptides can include three internally cross-linked or stitched amino acids, e.g., yielding two staples arising from a common origin. A peptide stitch includes at least three internally cross-linked amino acids, wherein the middle of the three amino acids (referred to here as the core or central amino acid) forms an internal cross-link (between alpha carbons) with each of the two flanking modified amino acids. The alpha carbon of the core amino acid has side chains that are internal cross-links to the alpha carbons of other amino acids in the peptide, which can be saturated or not saturated. Amino acids cross-linked to the core amino acid can be separated from the core amino acid in either direction by 2, 3, or 6 amino acids (e.g., i, i−3, i, i−4, i, i−7, i, i+3, i, i+4, i, i+7, where "i" is the core amino acid). The number of amino acids on either side of the core (e.g., between the core amino acid and an amino acid cross-linked to the core) can be the same or different.

Figure 6:
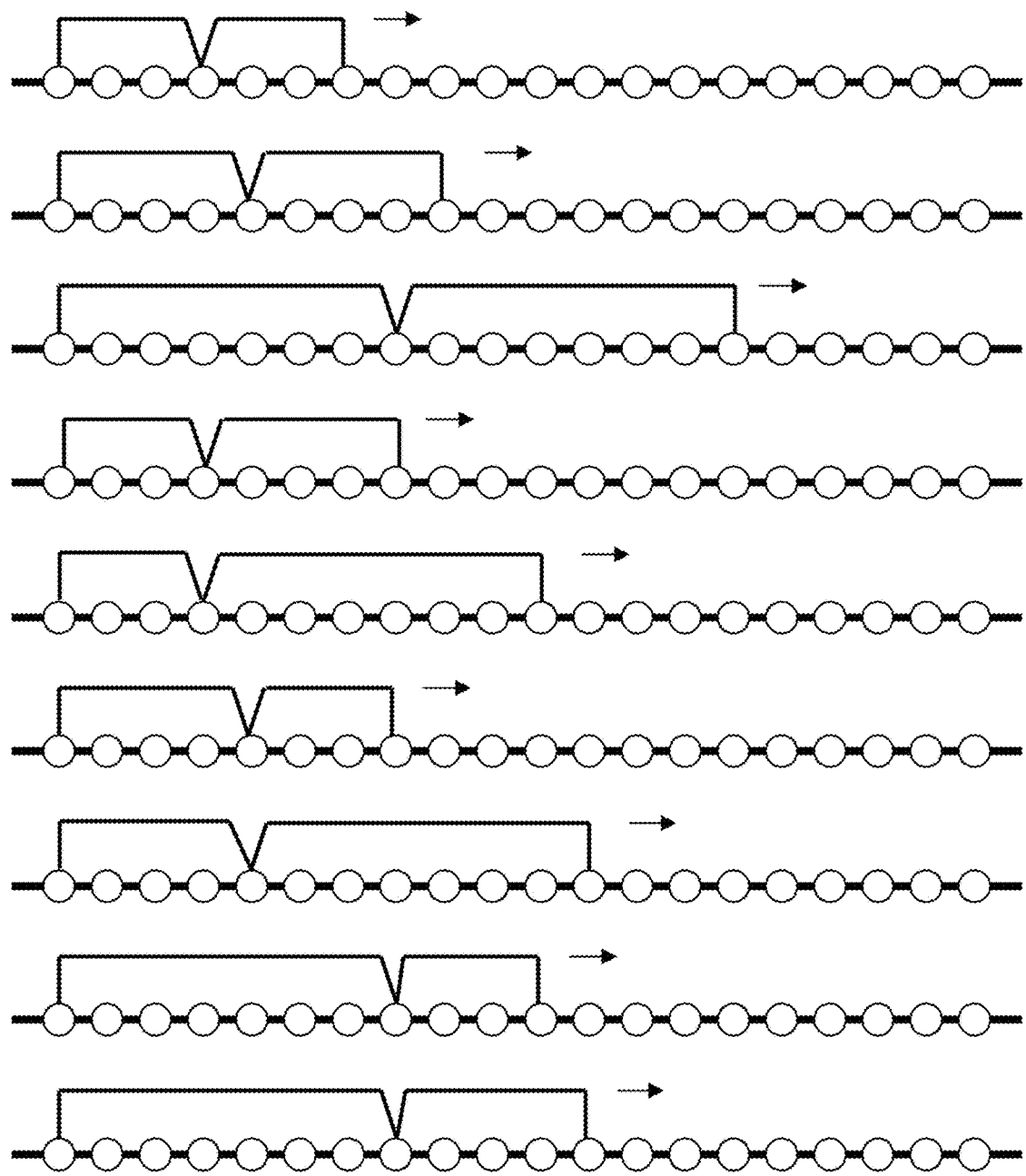
FIG. 6 is a schematic showing exemplary staple walks using various lengths of branched double staple moieties.

In some embodiments, peptides herein can include a combination of at least one (e.g., 1, 2, 3, 4, or 5) staple and at least one (e.g., 1, 2, 3, 4, or 5) stitch. FIG. 6 illustrates example staple walks using various lengths of branched stitched moieties.

Selection of amino acids for modification (e.g., to support an internal cross-link) can also be facilitated by staple scanning. The term "staple scan" refers to the synthesis of a library of stapled peptides whereby the location of the i and i+3; i and i+4; and i and i+7 single and multiple staple, or stitches, are positioned sequentially down the length of the peptide sequence, sampling all possible positions, to identify desired, effective, suitable, or optimal properties and activities for the stapled or stitched constructs. Examples of staple scanning methods are illustrated in the figures. Suitable tethers are described herein and in, e.g., US2005/0250680, PCT/US2008/058575, WO 2009/108261, and WO 2010/148335.

Amino acid side chains suitable for use in the peptides disclosed herein are known in the art. For example, suitable amino acid side chains include methyl (as the alpha-amino acid side chain for alanine is methyl), 4-hydroxyphenylmethyl (as the alpha-amino acid side chain for tyrosine is 4-hydroxyphenylmethyl) and thiomethyl (as the alpha-amino acid side chain for cysteine is thiomethyl), etc. A "terminally unsaturated amino acid side chain" refers to an amino acid side chain bearing a terminal unsaturated moiety, such as a substituted or unsubstituted, double bond (e.g., olefinic) or a triple bond (e.g., acetylenic), that participates in crosslinking reaction with other terminal unsaturated moieties in the polypeptide chain. In certain embodiments, a "terminally unsaturated amino acid side chain" is a terminal olefinic amino acid side chain. In certain embodiments, a "terminally unsaturated amino acid side chain" is a terminal acetylenic amino acid side chain. In certain embodiments, the terminal moiety of a "terminally unsaturated amino acid side chain" is not further substituted.

As noted above, an internal tether or cross-link can extend across the length of one helical turn (i.e., about 3.4 amino acids (i.e., i, i+3, or i, i+4) or two helical turns (i.e., about 7 amino acids (i.e., i, i+7). Accordingly, amino acids positioned at i and i+3; i and i+4; or i and i+7 are ideal candidates for chemical modification and cross-linking. Thus, for example, where a peptide has the sequence . . . $Xaa_1$, $Xaa_2$, $Xaa_3$, $Xaa_4$, $Xaa_5$, $Xaa_6$, $Xaa_7$, $Xaa_8$, $Xaa_9$ . . . (wherein, " . . . " indicates the optional presence of additional amino acids), cross-links between $Xaa_1$ and $Xaa_4$, or between $Xaa_1$ and $Xaa_5$, or between $Xaa_1$ and $Xaa_8$ are useful as are cross-links between $Xaa_2$ and $Xaa_5$, or between $Xaa_2$ and $Xaa_6$, or between $Xaa_2$ and $Xaa_9$, etc.

Figure 7:
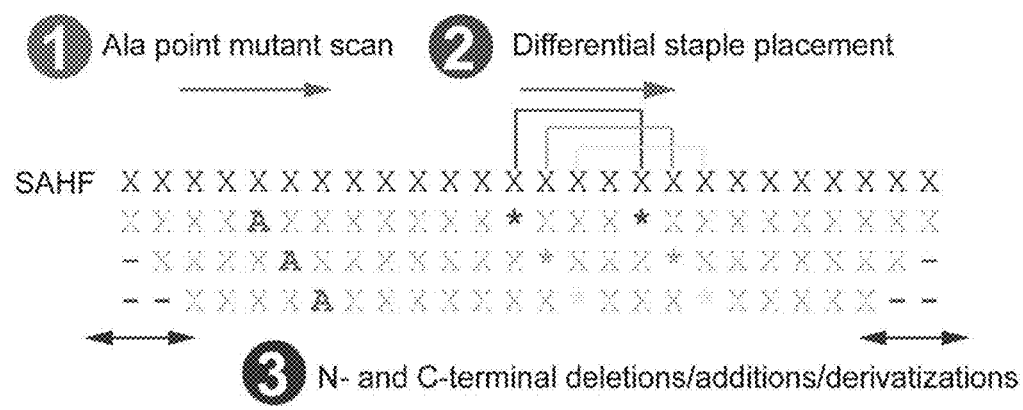
FIG. 7 is a schematic showing exemplary chemical alterations that are employed to generate stapled antimicrobial peptide derivatives.

Polypeptides can include more than one crosslink within the polypeptide sequence to either further stabilize the sequence or facilitate the stabilization of longer polypeptide stretches. If the polypeptides are too long to be readily synthesized in one part, independently synthesized, cross-linked peptides can be conjoined by a technique called native chemical ligation (see, e.g., Bang, et al., J. Am. Chem. Soc. 126:1377). Alternately, large peptides are routinely synthesized using a convergent approach whereby fully protected fragments are specifically and sequentially reacted to form the full length desired product, after final deprotection, such as in the industrial synthesis of Fuzeon. FIG. 7 is a schematic showing example chemical alterations that are employed to generate stapled antimicrobial peptide derivatives.

Compounds

The invention features a modified polypeptide of Formula (I),

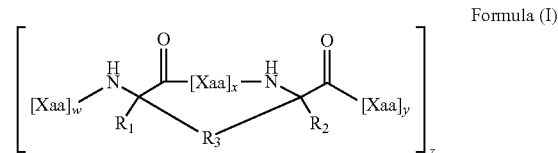

Formula (I)

or a pharmaceutically acceptable salt thereof, wherein;

each Xaa is independently an amino acid;

each $R_1$ and $R_2$ are independently H or a $C_1$ to $C_{10}$ alkyl, alkenyl, alkynyl, arylalkyl, cycloalkylalkyl, heteroarylalkyl, or heterocyclylalkyl;

each $R_3$ is independently alkylene, alkenylene or alkynylene (e.g., a $C_6$, $C_7$, or $C_{11}$ alkenylene) substituted with 1-6 $R_4$;

each $R_4$ is independently —$NH_3$ or —OH, wherein each —$NH_3$ is optionally substituted; wherein each $R_3$ replaces, relative to the corresponding parent (i.e., unmodified) non-internally cross-linked AMP, the side chains of at least one pair (e.g., one or two pairs) of amino acids separated by 2, 3, or 6 amino acids (i.e., x=2, 3, or 6).

As used above, and elsewhere in the present document, a "corresponding parent (i.e., unmodified) non-internally cross-linked AMP" can be a wild-type AMP, or any of the variants of a wild-type AMP disclosed in the present document, except that such a variant would not include an internal cross-link as described herein.

In the case of Formula I, the following embodiments are among those disclosed.

In cases where x=2 (i.e., i+3 linkage), $R_3$ can be, for example, a $C_7$ alkylene or alkenylene. Where it is an alkenylene there can one or more double bonds. In cases where x=6 (i.e., i+4 linkage), $R_3$ can be, for example, a $C_{11}$, $C_{12}$, or $C_{13}$ alkylene or alkenylene. Where it is an alkenylene, there can one or more double bonds. In cases where x=3 (i.e., i+4 linkage), $R_3$ can be, for example, a $C_8$ alkylene or alkenylene. Where it is an alkenylene, there can one or more double bonds.

In certain instances, the two alpha, alpha disubstituted stereocenters (alpha carbons) are both in the R configuration or S configuration (e.g., i, i+4 cross-link), or one stereocenter is R and the other is S (e.g., i, i+7 cross-link). Thus, where Formula I is depicted as

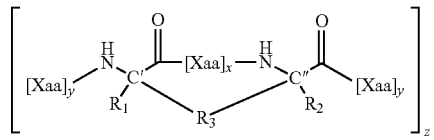

the C' and C" disubstituted stereocenters can both be in the R configuration or they can both be in the S configuration, for example when x is 3. When x is 6, the C' disubstituted stereocenter is in the R configuration and the C" disubstituted stereocenter is in the S configuration or the C' disubstituted stereocenter is in the S configuration and the C" disubstituted stereocenter is in the R configuration. An $R_3$ double bond may be in the E or Z stereochemical configuration. Similar configurations are possible for the carbons in Formula II corresponding to C' and C" in the formula depicted immediately above.

In some instances, the polypeptide includes an amino acid sequence which, in addition to the amino acids side chains that are replaced by a cross-link, have 1, 2, 3, 4, 5, 6, 7, 8, 9, 10, 11, or 12 amino acid changes (e.g., conservative amino acid changes) in any of SEQ ID NOs: 1-13.

In some embodiments, a compound has the Formula (II):

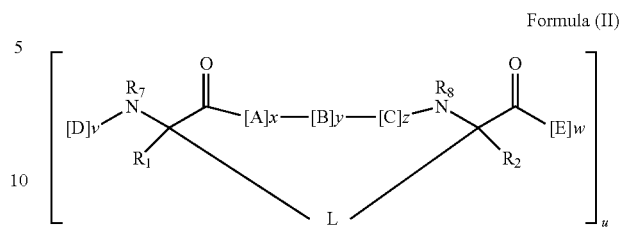

Formula (II)

wherein:
each A, C, D, and E is independently a natural or non-natural amino acid;
each B is independently a natural or non-natural amino acid, amino acid analog,

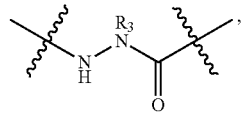

[—NH-$L_4$-CO—], [—NH-$L_4$-$SO_2$—], or [—NH-$L_4$-];
each $R_1$ is independently —H, alkyl, alkenyl, alkynyl, arylalkyl, cycloalkyl, cycloalkylalkyl, heteroalkyl, or heterocycloalkyl, any of which is unsubstituted or substituted, or together with $R_1$ and the atom to which both $R_1$ and L are bound forms a ring;
each $R_2$ is independently —H, alkyl, alkenyl, alkynyl, arylalkyl, cycloalkyl, cycloalkylalkyl, heteroalkyl, or heterocycloalkyl, any of which is unsubstituted or substituted, or together with $R_2$ and the atom to which both $R_2$ and L are bound forms a ring;
each $R_3$ is independently hydrogen, alkyl, alkenyl, alkynyl, arylalkyl, heteroalkyl, cycloalkyl, heterocycloalkyl, cycloalkylalkyl, aryl, or heteroaryl, any of which is unsubstituted or substituted;
each L is independently a macrocycle-forming linker;
each $L_4$ is independently alkylene, alkenylene, alkynylene, heteroalkylene, cycloalkylene, heterocycloalkylene, arylene, heteroarylene, or [—$R_4$—K—$R_4$-$]_n$, any of which is unsubstituted or substituted;
each $R_4$ is independently alkylene, alkenylene, alkynylene, heteroalkylene, cycloalkylene, heterocycloalkylene, arylene, or heteroarylene, any of which is unsubstituted or substituted;
each K is independently O, S, SO, $SO_2$, CO, $CO_2$, $CONR_3$, $OSO_2NR_3$, $NR_{3q}$, $CONR_{3q}$, $OCONR_{3q}$, or $OSO_2NR_{3q}$, wherein each $R_{3q}$ is independently a point of attachment to $R_1$ or $R_2$;
each n is independently 1, 2, 3, 4, or 5;
each $R_7$ is independently —H, alkyl, alkenyl, alkynyl, arylalkyl, cycloalkyl, heteroalkyl, cycloalkylalkyl, heterocycloalkyl, aryl, or heteroaryl, any of which is unsubstituted or substituted, or part of a cyclic structure with a D residue;
each $R_8$ is independently —H, alkyl, alkenyl, alkynyl, arylalkyl, cycloalkyl, heteroalkyl, cycloalkylalkyl, heterocycloalkyl, aryl, or heteroaryl, any of which is unsubstituted or substituted, or part of a cyclic structure with an E residue;
each v and w is independently an integer from 0-1000, from 1-1000, or 3-1000;
each x, y and z is independently 0, 1, 2, 3, 4, 5, 6, 7, 8, 9, or 10; and
u is 1, 2, 3, 4, 5, 6, 7, 8, 9, or 10.

In some embodiments, each v and w is independently 0, 1, 2, 3, 4, 5, 6, 7, 8, 9, 10, 11, 12, 13, 14, 15, 16, 17, 18, 19, or 20. In some embodiments, each w is independently an integer from 3-1000, for example 3-500, 3-200, 3-100, 3-50, 3-30, 3-20, or 3-10. In some embodiments, w is an integer from 3-10, for example 3-6, 3-8, 6-8, or 6-10. In some embodiments, w is 3. In other embodiments, w is 6. In some embodiments, each v is independently an integer from 1-1000, for example 1-500, 1-200, 1-100, 1-50, 1-30, 1-20, or 1-10. In some embodiments, v is 2. In one example, at least one of $R_1$ and $R_2$ is alkyl that is unsubstituted or substituted with halo-. In another example, both $R_1$ and $R_2$ are independently alkyl that is unsubstituted or substituted with halo-. In some embodiments, at least one of $R_1$ and $R_2$ is methyl. In other embodiments, $R_1$ and $R_2$ are methyl.

In some embodiments, x+y+z is at least 2 or at least 3. In other embodiments, x+y+z is 1, 2, 3, 4, 5, 6, 7, 8, 9 or 10. In some embodiments, the sum of x+y+z is 3 or 6. In some embodiments, the sum of x+y+z is 3. In other embodiments, the sum of x+y+z is 6. Each occurrence of A, B, C, D, or E in a macrocycle or macrocycle precursor is independently selected. For example, a sequence represented by the formula $[A]_x$, when x is 3, encompasses embodiments where the amino acids are not identical, e.g. Gln-Asp-Ala, as well as embodiments where the amino acids are identical, e.g. Gln-Gln-Gln. This applies for any value of x, y, or z in the indicated ranges. Similarly, when u is greater than 1, each compound can encompass compounds that are the same or different. For example, a compound can comprise compounds comprising different linker lengths or chemical compositions.

In some embodiments, the compound comprises a secondary structure that is an α-helix where $R_8$ is —H, allowing for intrahelical hydrogen bonding. In some embodiments, at least one of A, B, C, D, or E is an α,α-disubstituted amino acid. In one example, B is an α,α-disubstituted amino acid. For instance, at least one of A, B, C, D, or E is 2-aminoisobutyric acid. In other embodiments, at least one of A, B, C, D, or E is

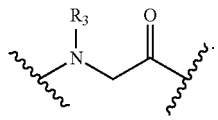

In other embodiments, the length of the macrocycle-forming linker L as measured from a first Cα to a second Cα is selected to stabilize a desired secondary peptide structure, such as an α-helix formed by residues of the compound including, but not necessarily limited to, those between the first Cα to a second Cα.

In some embodiments, a compound of Formula (II) has the Formula (IIa):

Formula (IIa)

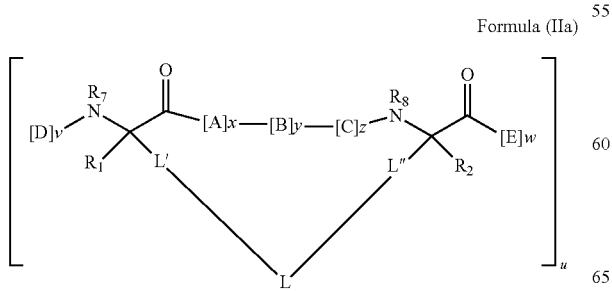

wherein:
each A, C, D, and E is independently a natural or non-natural amino acid;
each B is independently a natural or non-natural amino acid, amino acid analog,

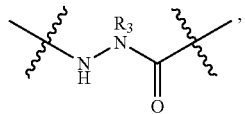

[—NH-$L_4$-CO—], [—NH-$L_4$-$SO_2$—], or [—NH-$L_4$-];
each L is independently a macrocycle-forming linker;
each L' is independently alkylene, alkenylene, alkynylene, heteroalkylene, cycloalkylene, heterocycloalkylene, arylene, or heteroarylene, any of which is unsubstituted or substituted, or a bond, or together with $R_1$ and the atom to which both $R_1$ and L' are bound forms a ring;
each L" is independently alkylene, alkenylene, alkynylene, heteroalkylene, cycloalkylene, heterocycloalkylene, arylene, or heteroarylene, any of which is unsubstituted or substituted, or a bond, or together with $R_2$ and the atom to which both $R_2$ and L" are bound forms a ring;
each $R_1$ is independently —H, alkyl, alkenyl, alkynyl, arylalkyl, cycloalkyl, cycloalkylalkyl, heteroalkyl, or heterocycloalkyl, any of which is unsubstituted or substituted, or together with L' and the atom to which both $R_1$ and L' are bound forms a ring;
each $R_2$ is independently —H, alkyl, alkenyl, alkynyl, arylalkyl, cycloalkyl, cycloalkylalkyl, heteroalkyl, or heterocycloalkyl, any of which is unsubstituted or substituted, or together with L" and the atom to which both $R_2$ and L" are bound forms a ring;
$R_3$ is hydrogen, alkyl, alkenyl, alkynyl, arylalkyl, heteroalkyl, cycloalkyl, heterocycloalkyl, cycloalkylalkyl, aryl, or heteroaryl, any of which is unsubstituted or substituted;
each $L_4$ is independently alkylene, alkenylene, alkynylene, heteroalkylene, cycloalkylene, heterocycloalkylene, arylene, heteroarylene, or [—$R_4$—K—$R_4$-]$_n$, any of which is unsubstituted or substituted;
each $R_4$ is alkylene, alkenylene, alkynylene, heteroalkylene, cycloalkylene, heterocycloalkylene, arylene, or heteroarylene, any of which is unsubstituted or substituted;
each K is independently O, S, SO, $SO_2$, CO, $CO_2$, $CONR_3$, $OSO_2NR_3$, $NR_{3q}$, $CONR_{3q}$, $OCONR_{3q}$, or $OSO_2NR_{3q}$, wherein each $R_{3q}$ is independently a point of attachment to $R_1$ or $R_2$;
each n is independently 1, 2, 3, 4, or 5;
each $R_7$ is independently —H, alkyl, alkenyl, alkynyl, arylalkyl, cycloalkyl, heteroalkyl, cycloalkylalkyl, heterocycloalkyl, aryl, or heteroaryl, any of which is unsubstituted or substituted, or part of a cyclic structure with a D residue;
each $R_8$ is independently —H, alkyl, alkenyl, alkynyl, arylalkyl, cycloalkyl, heteroalkyl, cycloalkylalkyl, heterocycloalkyl, aryl, or heteroaryl, any of which is unsubstituted or substituted, or part of a cyclic structure with an E residue;
each v and w is independently an integer from 0-1000, from 1-1000, or 3-1000;
each x, y and z is independently 0, 1, 2, 3, 4, 5, 6, 7, 8, 9, or 10; and
u is 1, 2, 3, 4, 5, 6, 7, 8, 9, or 10.

In some embodiments, L is a macrocycle-forming linker of the formula -L$_1$-L$_2$-. In some embodiments, L$_1$ and L$_2$ are independently alkylene, alkenylene, alkynylene, heteroalkylene, cycloalkylene, heterocycloalkylene, arylene, heteroarylene, or [—R$_4$—K—R$_4$-]$_n$, any of which is unsubstituted or substituted.

In one example, at least one of R$_1$ and R$_2$ is alkyl that is unsubstituted or substituted with halo-. In another example, both R$_1$ and R$_2$ are independently alkyl that is unsubstituted or substituted with halo-. In some embodiments, at least one of R$_1$ and R$_2$ is methyl. In other embodiments, R$_1$ and R$_2$ are methyl.

In some embodiments, x+y+z is at least 2 or at least 3. In other embodiments, x+y+z is 1, 2, 3, 4, 5, 6, 7, 8, 9 or 10. Each occurrence of A, B, C, D, or E in a macrocycle or macrocycle precursor is independently selected. For example, a sequence represented by the formula [A]$_x$, when x is 3, encompasses embodiments where the amino acids are not identical, e.g. Gln-Asp-Ala as well as embodiments where the amino acids are identical, e.g. Gln-Gln-Gln. This applies for any value of x, y, or z in the indicated ranges. Similarly, when u is greater than 1, each compound may encompass moieties which are the same or different. For example, a compound may comprise moieties comprising different linker lengths or chemical compositions.

In some embodiments, the compound comprises a secondary structure that is a helix where R$_8$ is —H, allowing intrahelical hydrogen bonding. In some embodiments, at least one of A, B, C, D, or E is an α,α-disubstituted amino acid. In one example, B is an α,α-disubstituted amino acid. For instance, at least one of A, B, C, D, or E is 2-aminoisobutyric acid. In other embodiments, at least one of A, B, C, D or E is

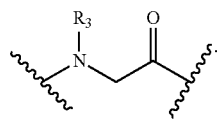

In other embodiments, the length of the macrocycle-forming linker L as measured from a first Cα to a second Cα is selected to stabilize a desired secondary peptide structure, such as a helix formed by residues of the compound including, but not necessarily limited to, those between the first Cα to a second Cα.

In some embodiments, the compound of Formula (II) has the Formula (IIb):

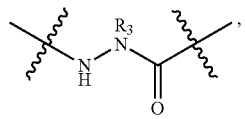

[—NH-L$_4$-CO—], [—NH-L$_4$-SO$_2$—], or [—NH-L$_4$-];

L is a macrocycle-forming linker of the formula -L$_1$-L$_2$-;

each R$_1$ is independently —H, alkyl, alkenyl, alkynyl, arylalkyl, cycloalkyl, cycloalkylalkyl, heteroalkyl, or heterocycloalkyl, any of which is unsubstituted or substituted, or together with L and the atom to which both R$_1$ and L are bound forms a ring;

each R$_2$ is independently —H, alkyl, alkenyl, alkynyl, arylalkyl, cycloalkyl, cycloalkylalkyl, heteroalkyl, or heterocycloalkyl, any of which is unsubstituted or substituted, or together with L and the atom to which both R$_2$ and L are bound forms a ring;

R$_3$ is hydrogen, alkyl, alkenyl, alkynyl, arylalkyl, heteroalkyl, cycloalkyl, heterocycloalkyl, cycloalkylalkyl, aryl, or heteroaryl, any of which is unsubstituted or substituted;

L' is a macrocycle-forming linker of the formula -L$_1$'-L$_2$'-;

each R$_1$' is independently —H, alkyl, alkenyl, alkynyl, arylalkyl, cycloalkyl, cycloalkylalkyl, heteroalkyl, or heterocycloalkyl, any of which is unsubstituted or substituted, or together with L' and the atom to which both R$_1$' and L' are bound forms a ring;

each R$_2$' is independently —H, alkyl, alkenyl, alkynyl, arylalkyl, cycloalkyl, cycloalkylalkyl, heteroalkyl, or heterocycloalkyl, any of which is unsubstituted or substituted, or together with L' and the atom to which both R$_2$' and L' are bound forms a ring;

L$_1$', L$_2$', and L$_4$ are independently alkylene, alkenylene, alkynylene, heteroalkylene, cycloalkylene, heterocycloalkylene, arylene, heteroarylene, or [—R$_4$—K—R$_4$-]$_n$, any of which is unsubstituted or substituted;

each R$_4$ is alkylene, alkenylene, alkynylene, heteroalkylene, cycloalkylene, heterocycloalkylene, arylene, or heteroarylene, any of which is unsubstituted or substituted;

each K is independently O, S, SO, SO$_2$, CO, CO$_2$, CONR$_3$, OSO$_2$NR$_3$, NR$_{3q}$, CONR$_{3q}$, OCONR$_{3q}$, or OSO$_2$NR$_{3q}$, wherein each R$_{3q}$ is independently a point of attachment to R$_1$, R$_2$, R$_1$', or R$_2$';

each n is independently 1, 2, 3, 4, or 5;

(Formula IIb)

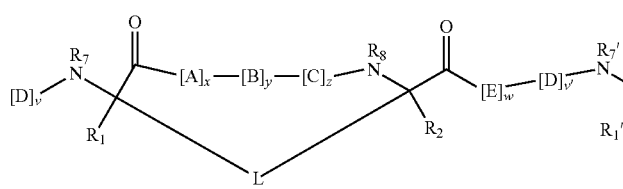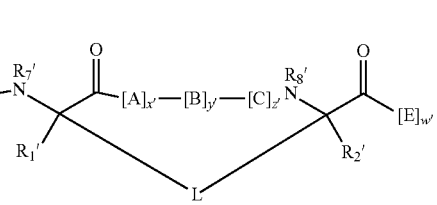

wherein:
each A, C, D, and E is independently an amino acid, wherein A, B, C, D, and E, taken together with the crosslinked amino acids connected by the macrocycle-forming linkers L and L', form the amino acid sequence of a target peptide;

each B is independently an amino acid, each R$_7$ is independently —H, alkyl, alkenyl, alkynyl, arylalkyl, cycloalkyl, heteroalkyl, cycloalkylalkyl, heterocycloalkyl, aryl, or heteroaryl, any of which is unsubstituted or substituted, or part of a cyclic structure with a D residue;

each R$_8$ is independently —H, alkyl, alkenyl, alkynyl, arylalkyl, cycloalkyl, heteroalkyl, cycloalkylalkyl, heterocycloalkyl, aryl, or heteroaryl, any of which is unsubstituted or substituted, or part of a cyclic structure with an E residue;

each $R_7'$ is independently —H, alkyl, alkenyl, alkynyl, arylalkyl, cycloalkyl, heteroalkyl, cycloalkylalkyl, heterocycloalkyl, aryl, or heteroaryl, any of which is unsubstituted or substituted, or part of a cyclic structure with a D residue;

each $R_8'$ is independently —H, alkyl, alkenyl, alkynyl, arylalkyl, cycloalkyl, heteroalkyl, cycloalkylalkyl, heterocycloalkyl, aryl, or heteroaryl, any of which is unsubstituted or substituted, or part of a cyclic structure with an E residue;

each x, y and z is independently 0, 1, 2, 3, 4, 5, 6, 7, 8, 9, or 10;

each x', y' and z' is independently 0, 1, 2, 3, 4, 5, 6, 7, 8, 9, or 10;

each v and w is independently an integer from 0-1000, from 1-1000, or 3-1000;

each v' and w' is independently an integer from 0-1000, from 1-1000, or 3-1000; and each n is 1, 2, 3, 4, or 5.

In some embodiments, the sum of x'+y'+z' is 1, 2, 3, 4, 5, 6, 7, 8, 9, or 10, for example 3 or 6, at least 2, or at least 3.

In some embodiments, the compounds have the Formula (IIc):

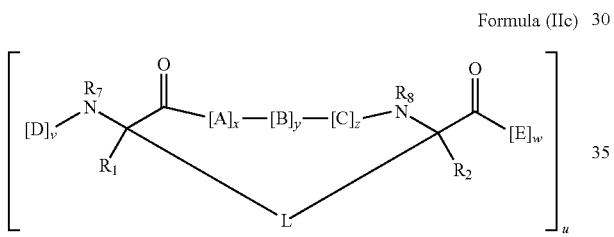

Formula (IIc)

wherein:
each A, C, D, and E is independently a natural or non-natural amino acid;

each B is independently a natural or non-natural amino acid, amino acid analog,

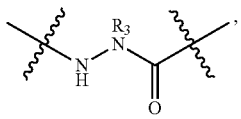

[—NH-$L_4$-CO—], [—NH-$L_4$-$SO_2$—], or [—NH-$L_4$-];

each $R_1$ is independently —H, alkyl, alkenyl, alkynyl, arylalkyl, cycloalkyl, cycloalkylalkyl, heteroalkyl, or heterocycloalkyl, any of which is unsubstituted or substituted, or together with $R_1$ and the atom to which both $R_1$ and L are bound forms a ring;

each $R_2$ is independently —H, alkyl, alkenyl, alkynyl, arylalkyl, cycloalkyl, cycloalkylalkyl, heteroalkyl, or heterocycloalkyl, any of which is unsubstituted or substituted, or together with $R_2$ and the atom to which both $R_2$ and L are bound forms a ring;

each $R_3$ is independently hydrogen, alkyl, alkenyl, alkynyl, arylalkyl, heteroalkyl, cycloalkyl, heterocycloalkyl, cycloalkylalkyl, aryl, or heteroaryl, any of which is unsubstituted or substituted;

each L is independently macrocycle-forming linker of the formula

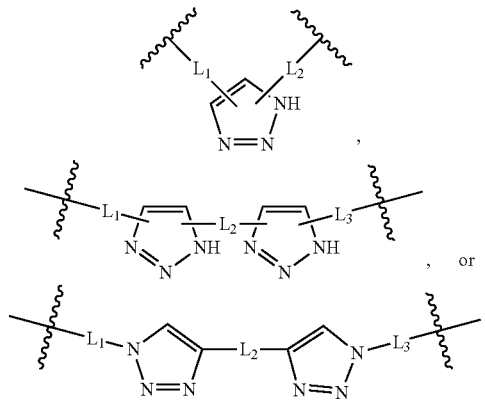

each $L_1$, $L_2$ and $L_3$ is independently alkylene, alkenylene, alkynylene, heteroalkylene, cycloalkylene, heterocycloalkylene, arylene, heteroarylene, or [—$R_4$—K—$R_4$-]$_n$, any of which is unsubstituted or substituted;

each $R_4$ is alkylene, alkenylene, alkynylene, heteroalkylene, cycloalkylene, heterocycloalkylene, arylene, or heteroarylene, any of which is unsubstituted or substituted;

each K is independently O, S, SO, $SO_2$, CO, $CO_2$, $CONR_3$, $OSO_2NR_3$, $NR_{3q}$, $CONR_{3q}$, $OCONR_{3q}$, or $OSO_2NR_{3q}$, wherein each $R_{3q}$ is independently a point of attachment to $R_1$ or $R_2$;

each $R_7$ is independently —H, alkyl, alkenyl, alkynyl, arylalkyl, cycloalkyl, heteroalkyl, cycloalkylalkyl, heterocycloalkyl, aryl, or heteroaryl, any of which is unsubstituted or substituted, or part of a cyclic structure with a D residue;

each $R_8$ is independently —H, alkyl, alkenyl, alkynyl, arylalkyl, cycloalkyl, heteroalkyl, cycloalkylalkyl, heterocycloalkyl, aryl, or heteroaryl, any of which is unsubstituted or substituted, or part of a cyclic structure with an E residue;

each v and w is independently an integer from 0-1000, from 1-1000, or 3-1000;

each x, y and z is independently 0, 1, 2, 3, 4, 5, 6, 7, 8, 9, or 10;

u is 1, 2, 3, 4, 5, 6, 7, 8, 9, or 10; and each n is 1, 2, 3, 4, or 5.

In one example, at least one of $R_1$ and $R_2$ is alkyl that is unsubstituted or substituted with halo-. In another example, both $R_1$ and $R_2$ are independently alkyl that is unsubstituted or substituted with halo-. In some embodiments, at least one of $R_1$ and $R_2$ is methyl. In other embodiments, $R_1$ and $R_2$ are methyl.

In some embodiments, x+y+z is at least 2 or at least 3. In other embodiments, x+y+z is 1, 2, 3, 4, 5, 6, 7, 8, 9 or 10. Each occurrence of A, B, C, D, or E in a macrocycle or macrocycle precursor is independently selected. For example, a sequence represented by the formula [A]$_x$, when x is 3, encompasses embodiments where the amino acids are not identical, e.g. Gln-Asp-Ala as well as embodiments where the amino acids are identical, e.g. Gln-Gln-Gln. This applies for any value of x, y, or z in the indicated ranges.

In some embodiments, each of the first two amino acid represented by E comprises an uncharged side chain or a negatively charged side chain. In some embodiments, each of the first three amino acid represented by E comprises an uncharged side chain or a negatively charged side chain. In some embodiments, each of the first four amino acid represented by E comprises an uncharged side chain or a negatively charged side chain. In some embodiments, one or more or each of the amino acid that is i+1, i+2, i+3, i+4, i+5, and/or i+6 with respect to E comprises an uncharged side chain or a negatively charged side chain.

In some embodiments, the first C-terminal amino acid and/or the second C-terminal amino acid represented by E comprise a hydrophobic side chain. For example, the first C-terminal amino acid and/or the second C-terminal amino acid represented by E comprises a hydrophobic side chain, for example a small hydrophobic side chain. In some embodiments, the first C-terminal amino acid, the second C-terminal amino acid, and/or the third C-terminal amino acid represented by E comprise a hydrophobic side chain. For example, the first C-terminal amino acid, the second C-terminal amino acid, and/or the third C-terminal amino acid represented by E comprises a hydrophobic side chain, for example a small hydrophobic side chain. In some embodiments, one or more or each of the amino acid that is i+1, i+2, i+3, i+4, i+5, and/or i+6 with respect to E comprises an uncharged side chain or a negatively charged side chain.

In some embodiments, each w is independently an integer from 1 to 1000. For example, the first amino acid represented by E comprises a small hydrophobic side chain. In some embodiments, w is between 2 and 1000. For example, the second amino acid represented by E comprises a small hydrophobic side chain. In some embodiments, w is between 3 and 1000. For example, the third amino acid represented by E comprises a small hydrophobic side chain. For example, the third amino acid represented by E comprises a small hydrophobic side chain. In some embodiments, w is between 4 and 1000. In some embodiments, w is between 5 and 1000. In some embodiments, w is between 6 and 1000. In some embodiments, w is between 7 and 1000. In some embodiments, w is between 8 and 1000.

In some embodiments, the compound comprises a secondary structure that is a helix where $R_8$ is —H, allowing intrahelical hydrogen bonding. In some embodiments, at least one of A, B, C, D, or E is an α,α-disubstituted amino acid. In one example, B is an α,α-disubstituted amino acid. For instance, at least one of A, B, C, D, or E is 2-aminoisobutyric acid. In other embodiments, at least one of A, B, C, D, or E is

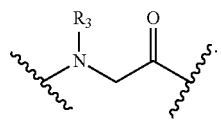

In other embodiments, the length of the macrocycle-forming linker L as measured from a first Cα to a second Cα is selected to stabilize a desired secondary peptide structure, such as a helix formed by residues of the compound including, but not necessarily limited to, those between the first Cα to a second Cα.

In some embodiments, L is a macrocycle-forming linker of the formula

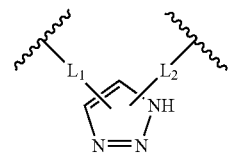

In some embodiments, L is a macrocycle-forming linker of the formula

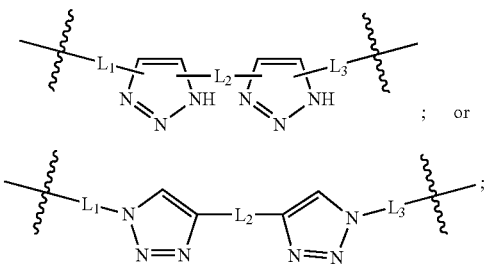

or a tautomer thereof.

Exemplary embodiments of the macrocycle-forming linker L are shown below.

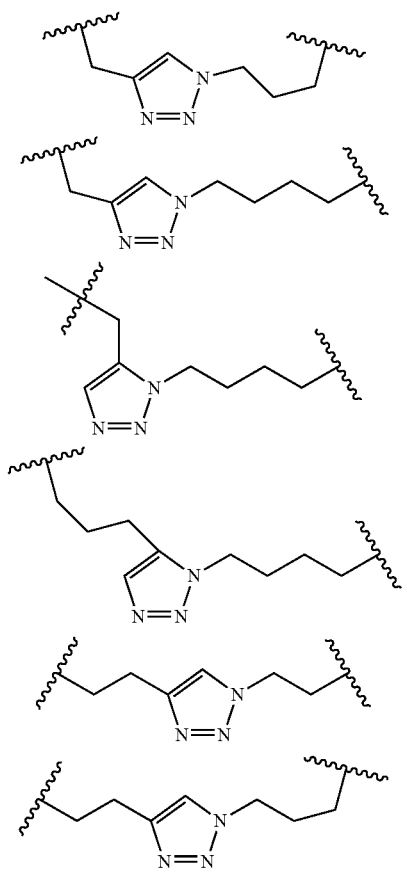

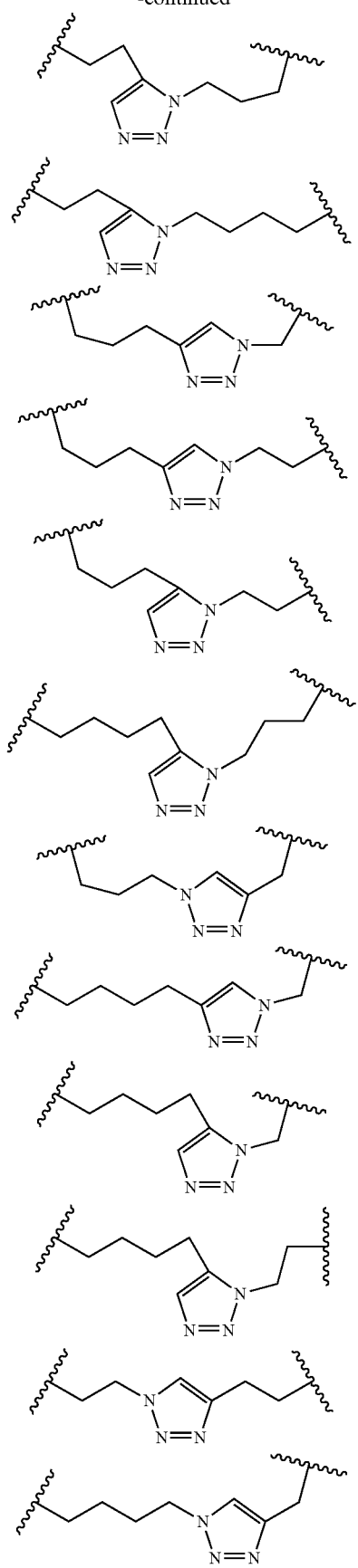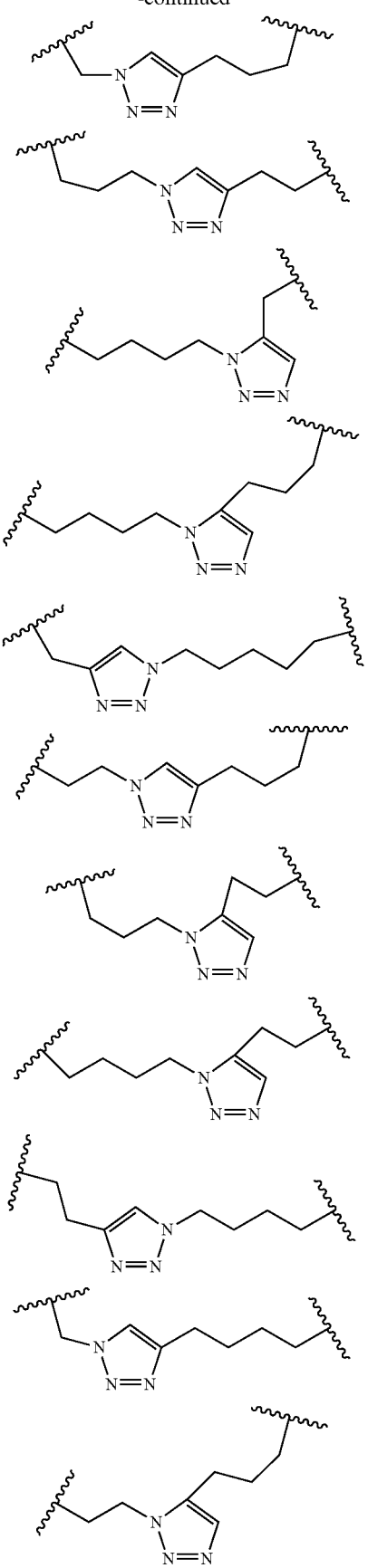

27
-continued
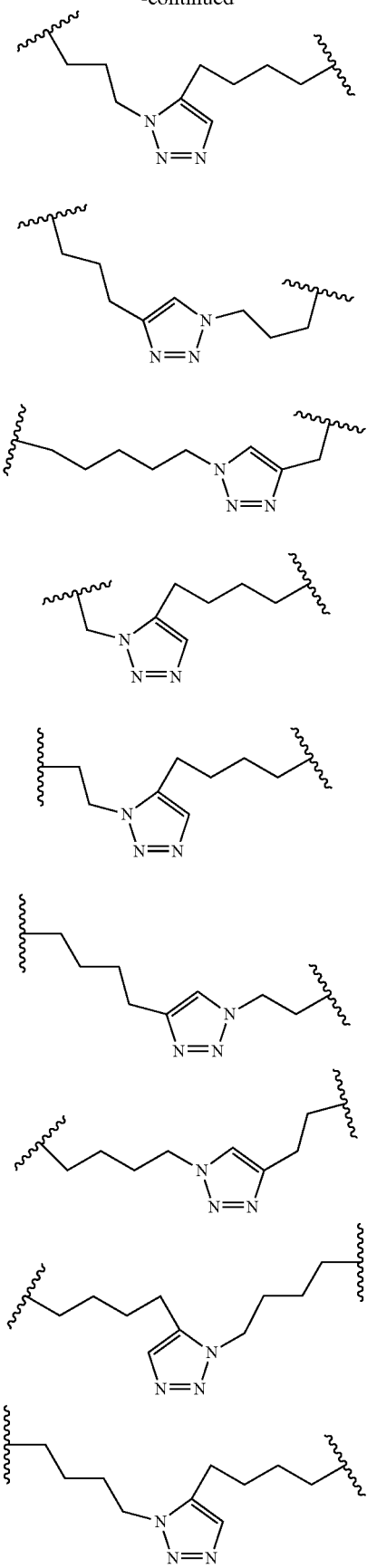
28
-continued
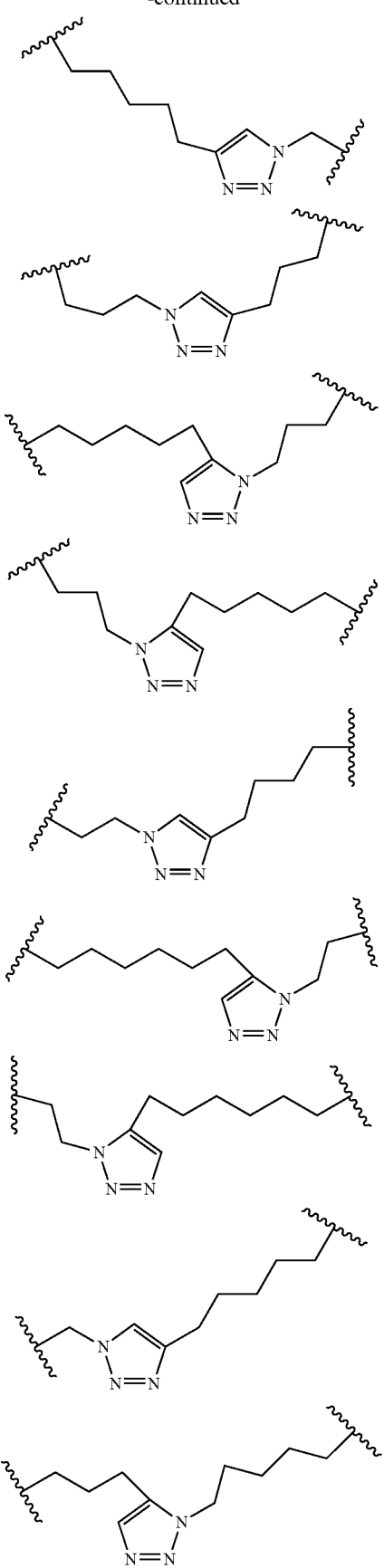

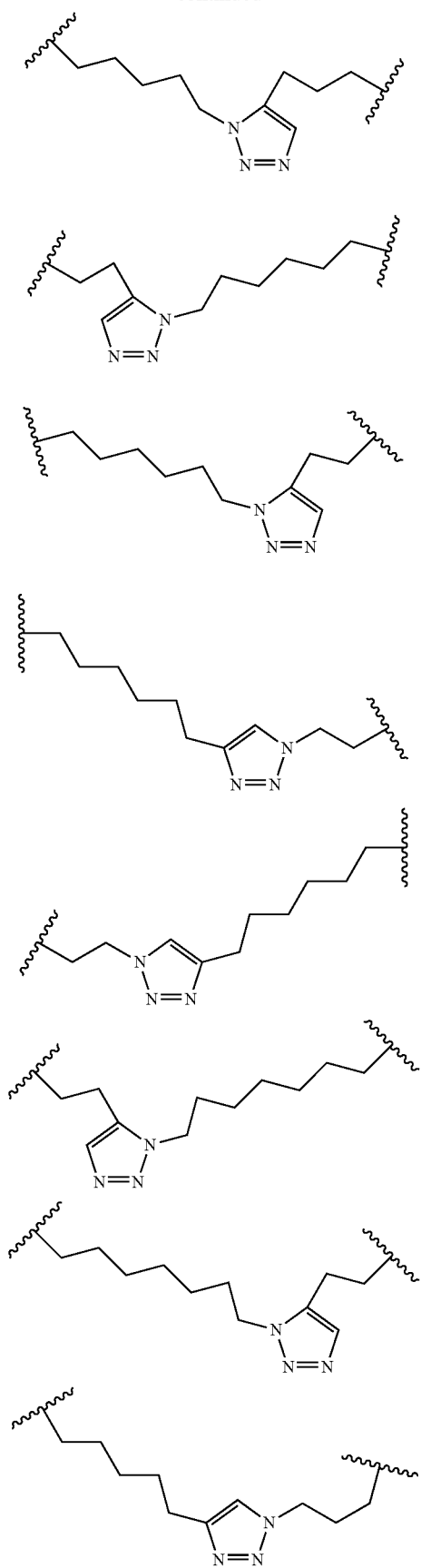
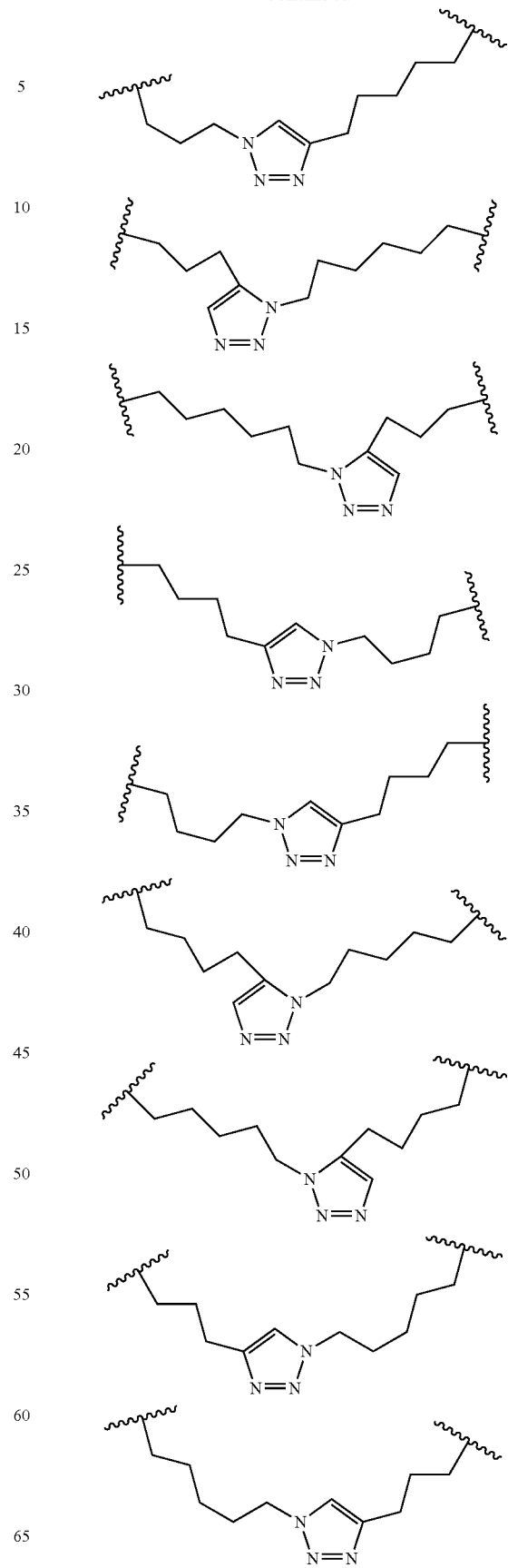

31
-continued
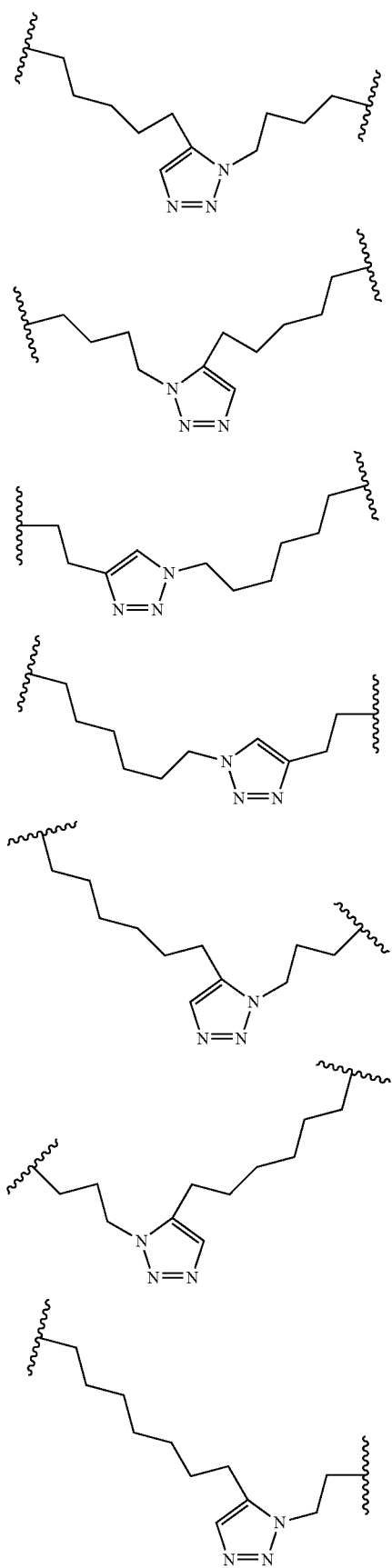
32
-continued
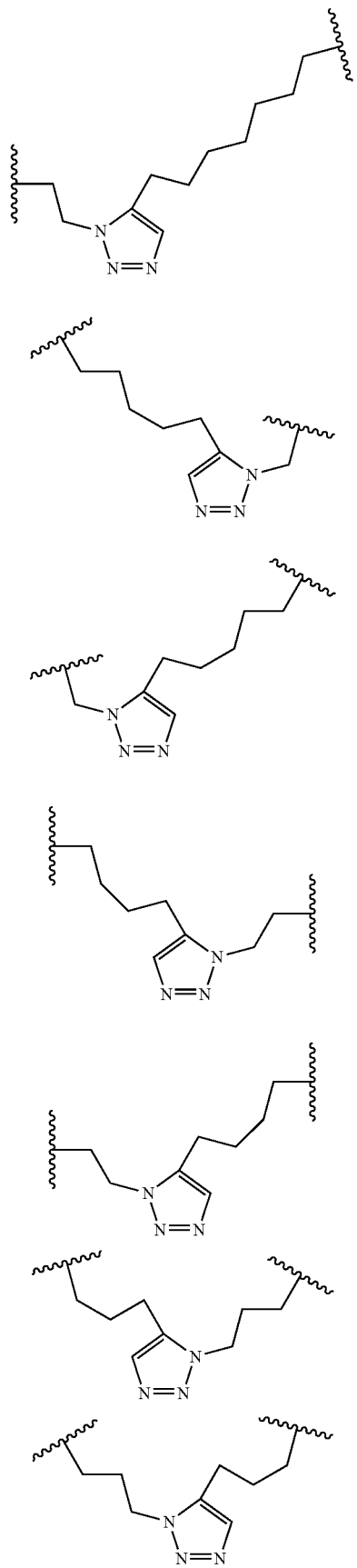

-continued

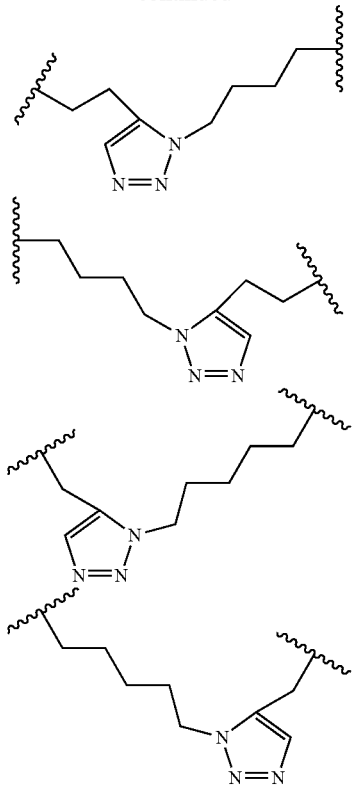

Amino acids that are used in the formation of triazole crosslinkers are represented according to the legend indicated below. Stereochemistry at the α-position of each amino acid is S unless otherwise indicated. For azide amino acids, the number of carbon atoms indicated refers to the number of methylene units between the α-carbon and the terminal azide. For alkyne amino acids, the number of carbon atoms indicated is the number of methylene units between the α-position and the triazole moiety plus the two carbon atoms within the triazole group derived from the alkyne.

| | |
|---|---|
| $5a5 | α-Me alkyne 1,5 triazole (5 carbon) |
| $5n3 | α-Me azide 1,5 triazole (3 carbon) |
| $4rn6 | α-Me R-azide 1,4 triazole (6 carbon) |
| $4a5 | α-Me alkyne 1,4 triazole (5 carbon) |

Where the macrocycle-forming linker spans approximately 1 turn of an α-helix, the linkage contains approximately 4 atoms to 12 atoms, approximately 6 atoms to 10 atoms, or approximately 8 atoms. Where the macrocycle-forming linker spans approximately 2 turns of the α-helix, the linkage contains approximately 7 atoms to 15 atoms, approximately 9 atoms to 13 atoms, or approximately 11 atoms. Where the macrocycle-forming linker spans approximately 3 turns of the α-helix, the linkage contains approximately 13 atoms to 21 atoms, approximately 15 atoms to 19 atoms, or approximately 17 atoms. Where the macrocycle-forming linker spans approximately 4 turns of the α-helix, the linkage contains approximately 19 atoms to 27 atoms, approximately 21 atoms to 25 atoms, or approximately 23 atoms. Where the macrocycle-forming linker spans approximately 5 turns of the α-helix, the linkage contains approximately 25 atoms to 33 atoms, approximately 27 atoms to 31 atoms, or approximately 29 atoms. Where the macrocycle-forming linker spans approximately 1 turn of the α-helix, the resulting macrocycle forms a ring containing approximately 17 members to 25 members, approximately 19 members to 23 members, or approximately 21 members. Where the macrocycle-forming linker spans approximately 2 turns of the α-helix, the resulting macrocycle forms a ring containing approximately 29 members to 37 members, approximately 31 members to 35 members, or approximately 33 members. Where the macrocycle-forming linker spans approximately 3 turns of the α-helix, the resulting macrocycle forms a ring containing approximately 44 members to 52 members, approximately 46 members to 50 members, or approximately 48 members. Where the macrocycle-forming linker spans approximately 4 turns of the α-helix, the resulting macrocycle forms a ring containing approximately 59 members to 67 members, approximately 61 members to 65 members, or approximately 63 members. Where the macrocycle-forming linker spans approximately 5 turns of the α-helix, the resulting macrocycle forms a ring containing approximately 74 members to 82 members, approximately 76 members to 80 members, or approximately 78 members.

In any embodiment herein, each v, w, v', and w' can be, independently, 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50. In any embodiment herein, each v, w, v', and w' can be, independently, 0-1000, 0-500, 0-400, 0-300, 0-200, 0-100, 0-50, 0-40, 0-30, 0-25, 0-20, 0-15, 0-10, 0-8, 0-6, 0-5, 1-1000, 1-500, 1-400, 1-300, 1-200, 1-100, 1-50, 1-40, 1-30, 1-25, 1-20, 1-15, 1-10, 1-8, 1-6, 1-5, 3-1000, 3-500, 3-400, 3-300, 3-200, 3-100, 3-50, 3-40, 3-30, 3-25, 3-20, 3-15, 3-10, 3-8, 3-6, or 3-5.

In one embodiment, the compound of Formula (II) is:

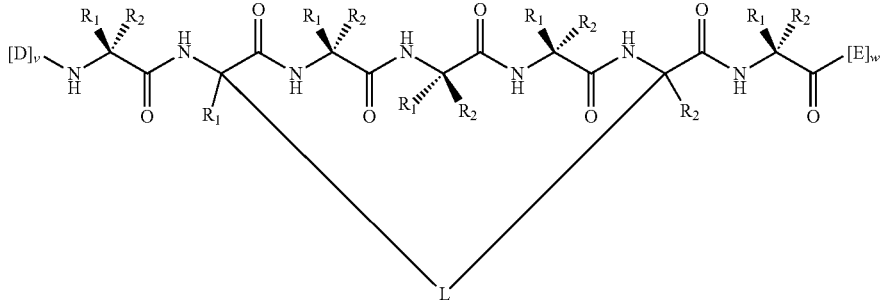

wherein each $R_1$ and $R_2$ is independently —H, alkyl, alkenyl, alkynyl, arylalkyl, cycloalkyl, cycloalkylalkyl, heteroalkyl, or heterocycloalkyl, any of which is unsubstituted or substituted.

In related embodiments, the compound comprises a structure of Formula (II) which is:

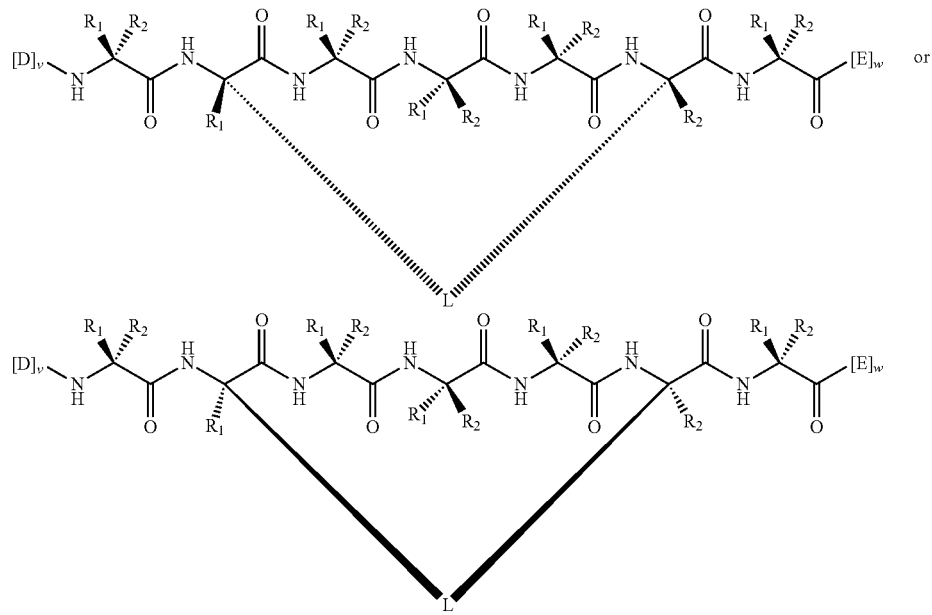

or

In some embodiments, the compound of Formula (II) is:

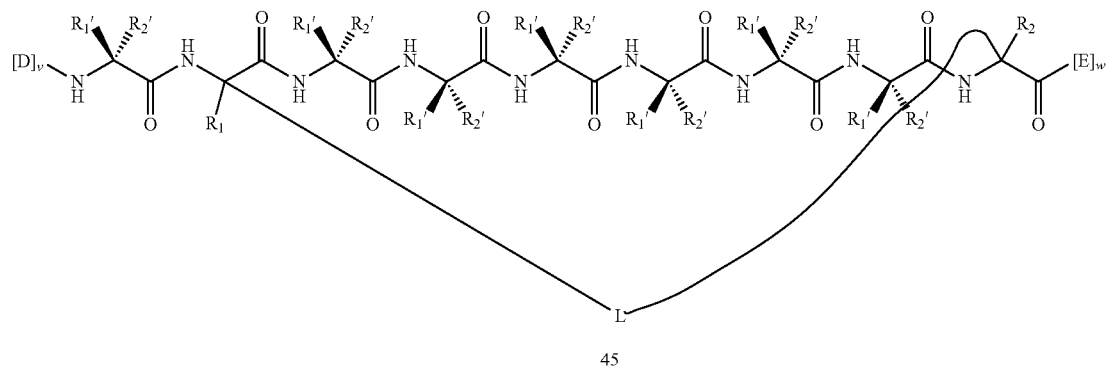

wherein each $R_1$ and $R_2$ is independently —H, alkyl, alkenyl, alkynyl, arylalkyl, cycloalkyl, cycloalkylalkyl, heteroalkyl, or heterocycloalkyl, unsubstituted or substituted with halo-.

In related embodiments, the compound of Formula (II) is:

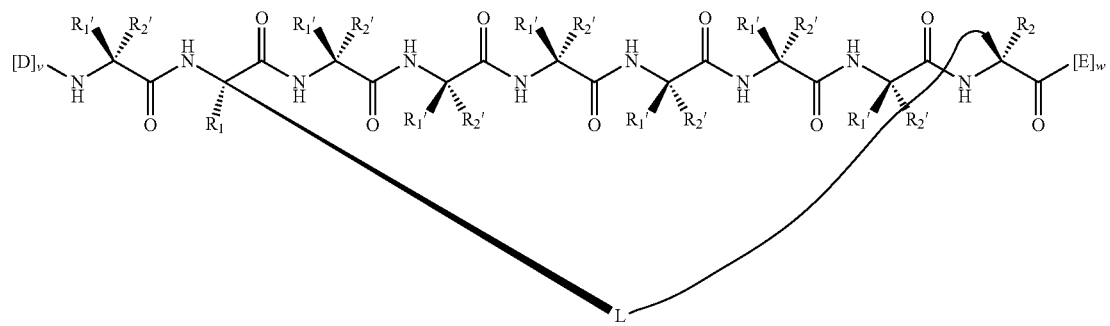

wherein each $R_1'$ and $R_2'$ is independently an amino acid side chain.

In other embodiments, the compound of Formula (II) is a compound of any of the formulas shown below:

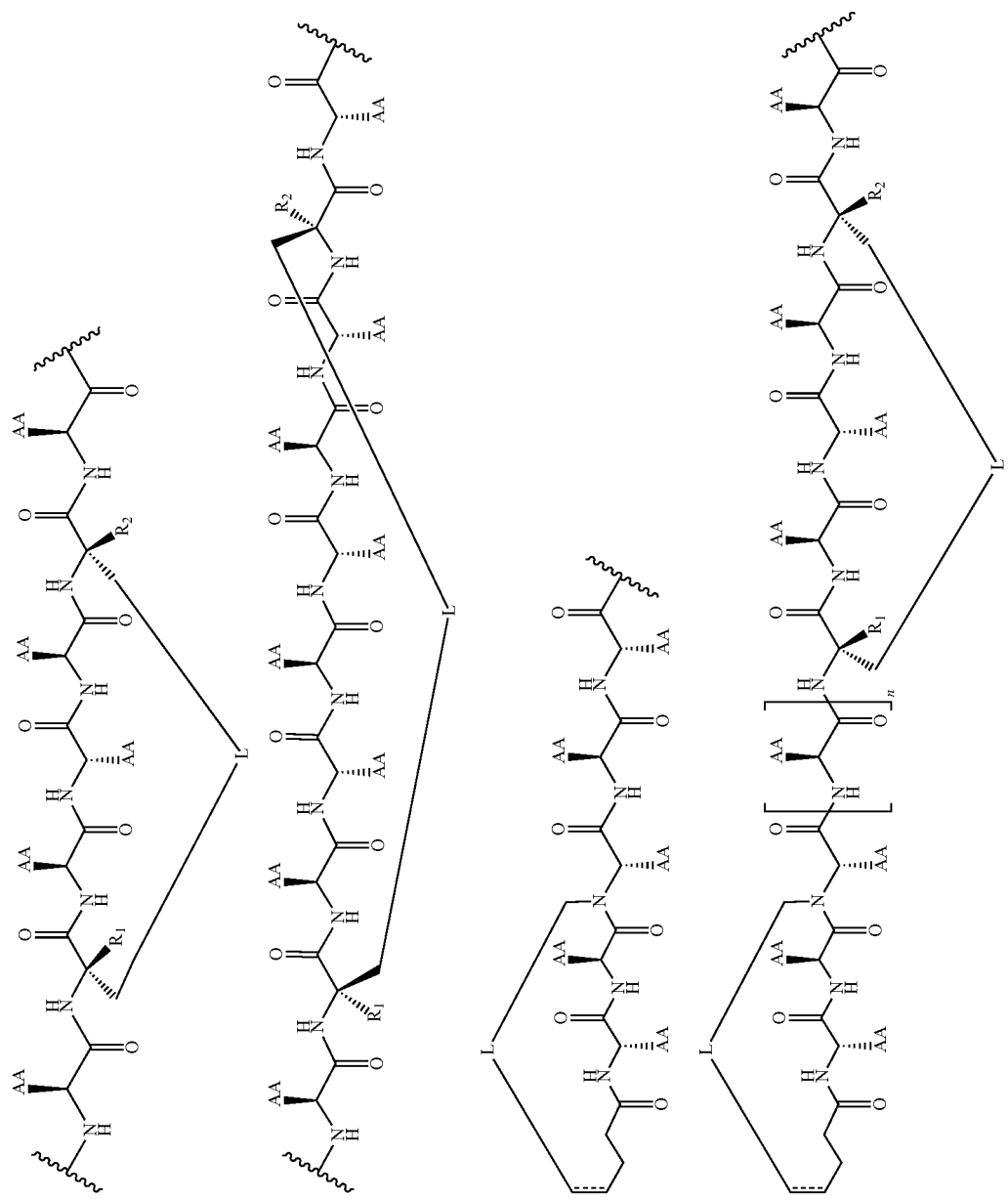

-continued
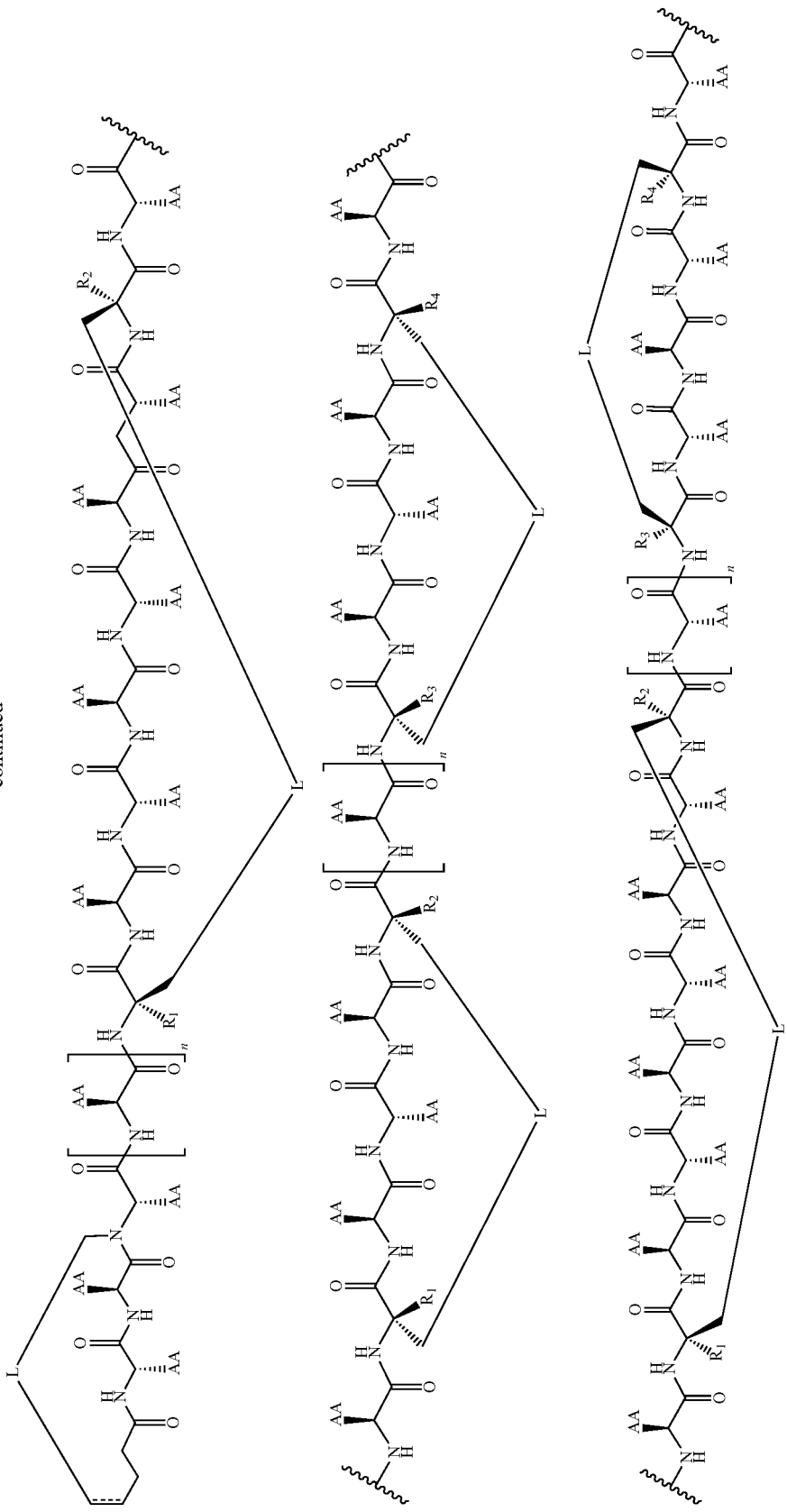

-continued
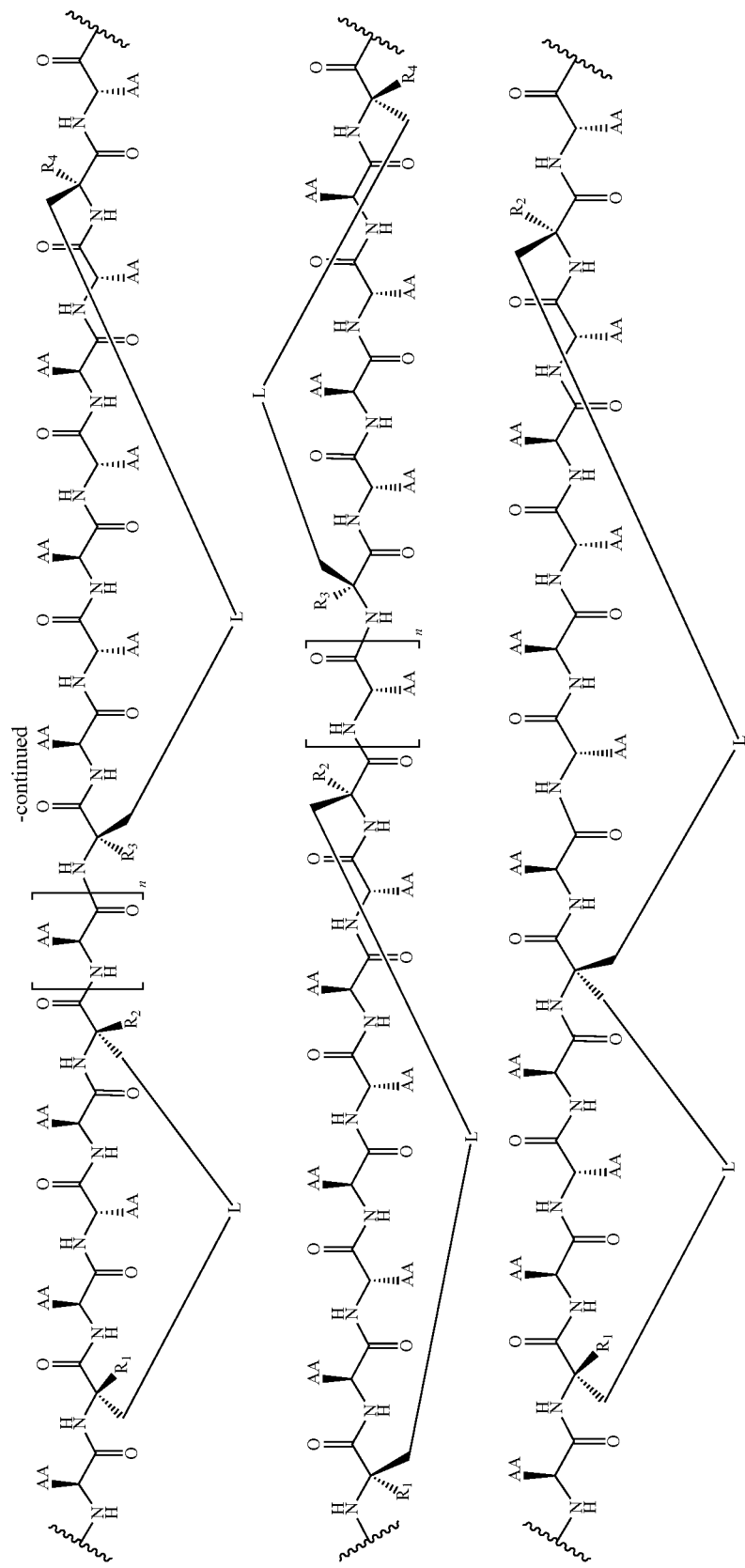

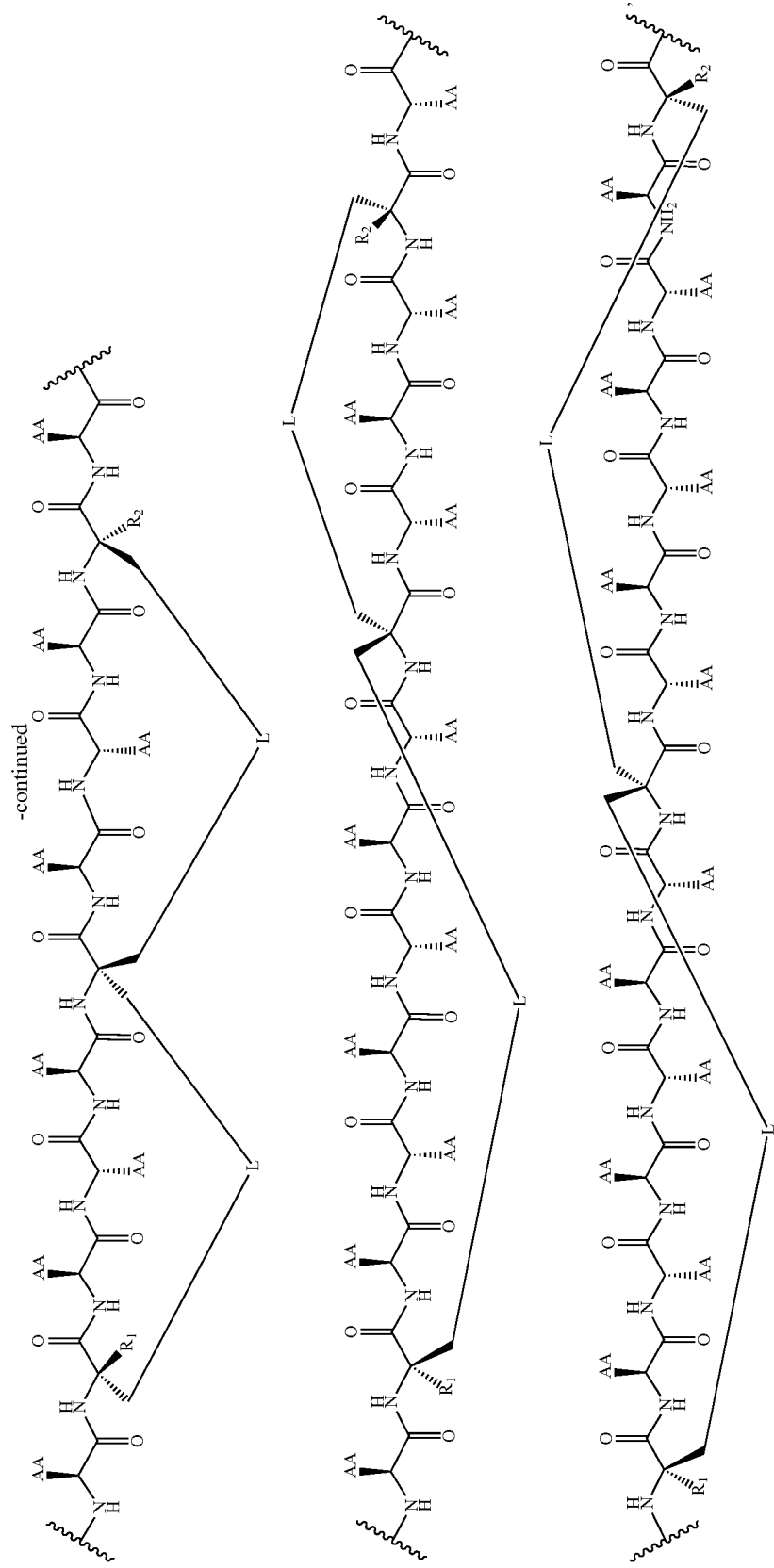

wherein "AA" represents any natural or non-natural amino acid side chain, "⟋" is [D]$_v$ or [E]$_w$ as defined above, and n is an integer from 0 to 20, 50, 100, 200, 300, 400 or 500. In some embodiments, the substituent "n" shown in the preceding paragraph is 0. In other embodiments, the substituent "n" shown in the preceding paragraph is less than 50, 40, 30, 20, 10, or 5.

Exemplary embodiments of the macrocycle-forming linker L are shown below.

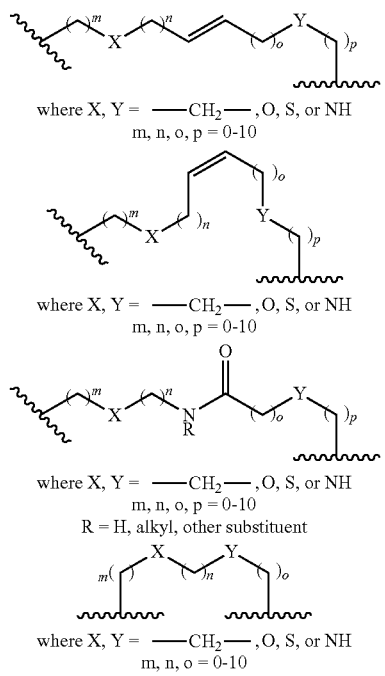

In other embodiments, [D] and/or [E] in the compound of Formula (II) are further modified in order to facilitate cellular uptake. In some embodiments, lipidating or PEGylating a compound facilitates cellular uptake, increases bioavailability, increases blood circulation, alters pharmacokinetics, decreases immunogenicity, and/or decreases the needed frequency of administration.

In other embodiments, at least one of [D] and [E] in the compound of Formula (II) represents a moiety comprising an additional macrocycle-forming linker such that the compound comprises at least two macrocycle-forming linkers. In a specific embodiment, a compound comprises two macrocycle-forming linkers. In one embodiment, u is 2.

In some embodiments, L is a macrocycle-forming linker of the formula -L$_1$-L$_2$-. In some embodiments, L$_1$ and L$_2$ are independently alkylene, alkenylene, alkynylene, heteroalkylene, cycloalkylene, heterocycloalkylene, arylene, heteroarylene, or [—R$_4$—K—R$_4$-]$_n$, any of which is unsubstituted or substituted; each R$_4$ is alkylene, alkenylene, alkynylene, heteroalkylene, cycloalkylene, heterocycloalkylene, arylene, or heteroarylene, any of which is unsubstituted or substituted; each K is independently O, S, SO, SO$_2$, CO, CO$_2$, CONR$_3$, OSO$_2$NR$_3$, NR$_{3q}$, CONR$_{3q}$, OCONR$_{3q}$, or OSO$_2$NR$_{3q}$, wherein each R$_{3q}$ is independently a point of attachment to R$_1$ or R$_2$; and each n is independently 1, 2, 3, 4, or 5.

In an embodiment of any of the Formulas described herein, L$_1$ and L$_2$, either alone or in combination, form a triazole or a thioether.

In an embodiment of any of the Formulas described herein, L$_1$ and L$_2$, either alone or in combination, do not form a triazole or a thioether.

In other embodiments, the length of the macrocycle-forming linker L as measured from a first α-carbon to a second α-carbon is selected to stabilize a desired secondary peptide structure, such as a helix formed by residues of the compound including, but not necessarily limited to, those between the first α-carbon to a second α-carbon.

In one example, at least one of R$_1$ and R$_2$ is alkyl, unsubstituted or substituted with halo-. In another example, both R$_1$ and R$_2$ are independently alkyl, unsubstituted or substituted with halo-. In some embodiments, at least one of R$_1$ and R$_2$ is methyl. In other embodiments, R$_1$ and R$_2$ are methyl.

In some embodiments, x+y+z is at least 2 or at least 3. In other embodiments, x+y+z is 1, 2, 3, 4, 5, 6, 7, 8, 9 or 10. Each occurrence of A, B, C, D, or E in a macrocycle or macrocycle precursor is independently selected. For example, a sequence represented by the formula [A]$_x$, when x is 3, encompasses embodiments where the amino acids are not identical, e.g. Gln-Asp-Ala, as well as embodiments where the amino acids are identical, e.g. Gln-Gln-Gln. This applies for any value of x, y, or z in the indicated ranges. Similarly, when u is greater than 1, each compound may encompass compounds which are the same or different. For example, a compound may comprise compounds comprising different linker lengths or chemical compositions.

In some embodiments, the compound comprises a secondary structure that is a helix where R$_8$ is —H, allowing intrahelical hydrogen bonding. In some embodiments, at least one of A, B, C, D, or E is an α,α-disubstituted amino acid. In one example, B is an α,α-disubstituted amino acid. For instance, at least one of A, B, C, D, or E is 2-aminoisobutyric acid. In other embodiments, at least one of A, B, C, D or E is

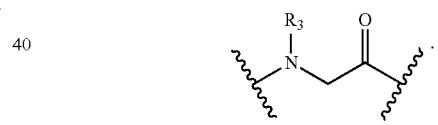

In some embodiments, w is from 1 to 1000. For example, the first amino acid represented by E comprises a small hydrophobic side chain. In some embodiments, w is from 2 to 1000. For example, the second amino acid represented by E comprises a small hydrophobic side chain. In some embodiments, w is from 3 to 1000. For example, the third amino acid represented by E can comprise a small hydrophobic side chain. For example, the third amino acid represented by E can comprise a small hydrophobic side chain. In some embodiments, w is from 4 and 1000. In some embodiments, w is from 5 and 1000. In some embodiments, w is from 6 and 1000. In some embodiments, w is from 7 and 1000. In some embodiments, w is from 8 and 1000. In some embodiments, w is an integer from 3-10, for example 3-6, 3-8, 6-8, or 6-10. In some embodiments, w is 3. In other embodiments, w is 6. In some embodiments, v is an integer from 1-10, for example 2-5. In some embodiments, v is 2. In some embodiments, v is 3.

In some embodiments, each of the first two amino acid represented by E comprises an uncharged side chain or a negatively charged side chain. In some embodiments, each of the first three amino acid represented by E comprises an uncharged side chain or a negatively charged side chain. In some embodiments, each of the first four amino acid represented by E comprises an uncharged side chain or a negatively charged side chain.

In some embodiments, the first C-terminal amino acid and/or the second C-terminal amino acid represented by E comprise a hydrophobic side chain. For example, the first C-terminal amino acid and/or the second C-terminal amino acid represented by E comprises a hydrophobic side chain, for example a small hydrophobic side chain. In some embodiments, the first C-terminal amino acid, the second C-terminal amino acid, and/or the third C-terminal amino acid represented by E comprise a hydrophobic side chain. For example, the first C-terminal amino acid, the second C-terminal amino acid, and/or the third C-terminal amino acid represented by E comprises a hydrophobic side chain, for example a small hydrophobic side chain.

In some embodiments, one or more or each of the amino acid that is i+1, i+2, i+3, i+4, i+5, and/or i+6 with respect to a first E comprises an uncharged side chain or a negatively charged side chain. In some embodiments, each E is independently an amino acid selected from the group consisting of Ala (alanine), D-Ala (D-alanine), Aib (α-aminoisobutyric acid), Sar (N-methyl glycine), and Ser (serine).

In other embodiments, [D] and/or [E] in the compound of Formula I, Ia, Ib, or Ic are further modified in order to facilitate cellular uptake. In some embodiments, lipidating or PEGylating a compound facilitates cellular uptake, increases bioavailability, increases blood circulation, alters pharmacokinetics, decreases immunogenicity and/or decreases the needed frequency of administration.

In other embodiments, at least one of [D] and [E] in the compound of Formula I, Ia, Ib, or Ic represents a moiety comprising an additional macrocycle-forming linker such that the compound comprises at least two macrocycle-forming linkers. In a specific embodiment, a compound comprises two macrocycle-forming linkers. In an embodiment, u is 2.

In other embodiments, the invention provides compounds of Formula (III):

Formula (III)

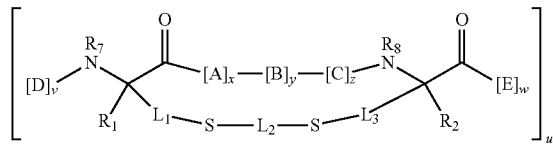

wherein:
each A, C, D, and E is independently a natural or non-natural amino acid;
each B is independently a natural or non-natural amino acid, amino acid analog,

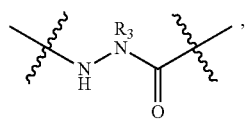

[—NH-L$_4$-CO—], [—NH-L$_4$-SO$_2$—], or [—NH-L$_4$-];
each R$_1$ is independently —H, alkyl, alkenyl, alkynyl, arylalkyl, cycloalkyl, cycloalkylalkyl, heteroalkyl, or heterocycloalkyl, any of which is unsubstituted or substituted, or together with R$_1$ and the atom to which R$_1$ and L are bound forms a ring;
each R$_2$ is independently —H, alkyl, alkenyl, alkynyl, arylalkyl, cycloalkyl, cycloalkylalkyl, heteroalkyl, or heterocycloalkyl, any of which is unsubstituted or substituted, or together with R$_2$ and the atom to which R$_2$ and L are bound forms a ring;
each R$_3$ is independently hydrogen, alkyl, alkenyl, alkynyl, arylalkyl, heteroalkyl, cycloalkyl, heterocycloalkyl, cycloalkylalkyl, aryl, or heteroaryl, any of which is unsubstituted or substituted;
each L$_1$, L$_2$, L$_3$ and L$_4$ is independently alkylene, alkenylene, alkynylene, heteroalkylene, cycloalkylene, heterocycloalkylene, arylene, heteroarylene or [—R$_4$—K—R$_4$-]$_n$, any of which is unsubstituted or substituted;
each K is independently O, S, SO, SO$_2$, CO, CO$_2$, CONR$_3$, OSO$_2$NR$_3$, NR$_{3q}$, CONR$_{3q}$, OCONR$_{3q}$, or OSO$_2$NR$_{3q}$, wherein each R$_{3q}$ is independently a point of attachment to R$_1$ or R$_2$;
each R$_4$ is independently alkylene, alkenylene, alkynylene, heteroalkylene, cycloalkylene, heterocycloalkylene, arylene, or heteroarylene, any of which is unsubstituted or substituted;
each R$_7$ is independently —H, alkyl, alkenyl, alkynyl, arylalkyl, cycloalkyl, heteroalkyl, cycloalkylalkyl, heterocycloalkyl, aryl, or heteroaryl, any of which is unsubstituted or substituted, or part of a cyclic structure with a D residue;
each R$_8$ is independently —H, alkyl, alkenyl, alkynyl, arylalkyl, cycloalkyl, heteroalkyl, cycloalkylalkyl, heterocycloalkyl, aryl, or heteroaryl, any of which is unsubstituted or substituted, or part of a cyclic structure with an E residue;
each v and w is independently an integer from 0-1000, from 1-1000, or 3-1000;
each x, y and z is independently 0, 1, 2, 3, 4, 5, 6, 7, 8, 9, or 10;
u is 1, 2, 3, 4, 5, 6, 7, 8, 9, or 10; and
each n is independently 1, 2, 3, 4, or 5.

In some embodiments, the length of the macrocycle-forming linker [-L$_1$-S-L$_2$-S-L$_3$-] as measured from a first α-carbon to a second α-carbon is selected to stabilize a desired secondary peptide structure, such as a helix (including, but not limited to a 3$_{10}$ helix or an α-helix) formed by residues of the compound including, but not necessarily limited to, those between the first α-carbon to a second α-carbon. In some embodiments, the thiol moieties are the side chains of the amino acid residues L-cysteine, D-cysteine, α-methyl-L cysteine, α-methyl-D-cysteine, L-homocysteine, D-homocysteine, α-methyl-L-homocysteine, or α-methyl-D-homocysteine. A bis-alkylating reagent is of the general formula X-L$_2$-Y, wherein L$_2$ is a linker moiety and X and Y are leaving groups that are displaced by —SH moieties to form bonds with L$_2$. In some embodiments, X and Y are halogens, such as I, Br, or Cl.

In other embodiments, the invention provides compounds of Formula (IV) or (IVa):

Formula (IV)

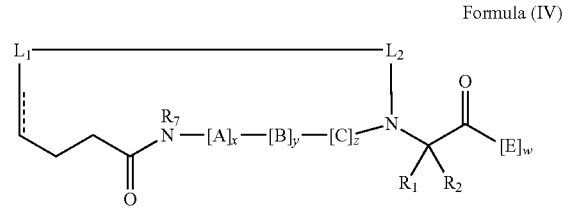

-continued

Formula (IVa)

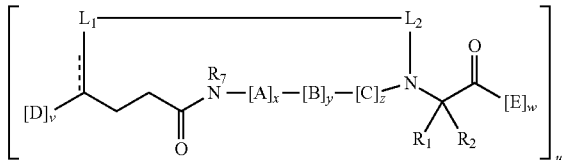

wherein:
each A, C, D, and E is independently a natural or non-natural amino acid;
each B is independently a natural or non-natural amino acid, amino acid analog,

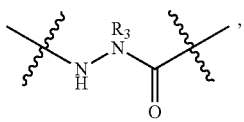

[—NH-L$_4$-CO—], [—NH-L$_4$-SO$_2$—], or [—NH-L$_4$-];

each R$_1$ is independently —H, alkyl, alkenyl, alkynyl, arylalkyl, cycloalkyl, cycloalkylalkyl, heteroalkyl, or heterocycloalkyl, any of which is unsubstituted or substituted, or part of a cyclic structure with an E residue;

each R$_2$ is independently —H, alkyl, alkenyl, alkynyl, arylalkyl, cycloalkyl, cycloalkylalkyl, heteroalkyl, or heterocycloalkyl, any of which is unsubstituted or substituted, or part of a cyclic structure with an E residue;

each R$_3$ is independently hydrogen, alkyl, alkenyl, alkynyl, arylalkyl, heteroalkyl, cycloalkyl, heterocycloalkyl, cycloalkylalkyl, aryl, or heteroaryl, any of which is unsubstituted or substituted;

each L is independently a macrocycle-forming linker of the formula -L$_1$-L$_2$-;

each L$_1$, L$_2$, and L$_4$ is independently alkylene, alkenylene, alkynylene, heteroalkylene, cycloalkylene, heterocycloalkylene, arylene, heteroarylene, or [—R$_4$—K—R$_4$-]$_n$, any of which is unsubstituted or substituted;

each R$_4$ is independently alkylene, alkenylene, alkynylene, heteroalkylene, cycloalkylene, heterocycloalkylene, arylene, or heteroarylene, any of which is unsubstituted or substituted;

each K is independently O, S, SO, SO$_2$, CO, CO$_2$, CONR$_3$, OSO$_2$NR$_3$, NR$_{3q}$, CONR$_{3q}$, OCONR$_{3q}$, or OSO$_2$NR$_{3q}$, wherein each R$_{3q}$ is independently a point of attachment to R$_1$ or R$_2$;

each R$_7$ is independently —H, alkyl, alkenyl, alkynyl, arylalkyl, cycloalkyl, heteroalkyl, cycloalkylalkyl, heterocycloalkyl, aryl, or heteroaryl, any of which is unsubstituted or substituted;

each v and w is independently integers from 0-1000, from 1-1000, or 3-1000;

each x, y and z is independently 0, 1, 2, 3, 4, 5, 6, 7, 8, 9, or 10;

u is 1, 2, 3, 4, 5, 6, 7, 8, 9, or 10; and each n is independently 1, 2, 3, 4, 5.

In one example, L$_1$ and L$_2$, either alone or in combination, do not form a triazole or a thioether.

In one example, at least one of R$_1$ and R$_2$ is alkyl that is unsubstituted or substituted with halo-. In another example, both R$_1$ and R$_2$ are independently alkyl that is unsubstituted or substituted with halo-. In some embodiments, at least one of R$_1$ and R$_2$ is methyl. In other embodiments, R$_1$ and R$_2$ are methyl.

In some embodiments, x+y+z is at least 1. In other embodiments, x+y+z is at least 2. In other embodiments, x+y+z is 1, 2, 3, 4, 5, 6, 7, 8, 9 or 10. Each occurrence of A, B, C, D, or E in a macrocycle or macrocycle precursor is independently selected. For example, a sequence represented by the formula [A]$_x$, when x is 3, encompasses embodiments where the amino acids are not identical, e.g. Gln-Asp-Ala, as well as embodiments where the amino acids are identical, e.g. Gln-Gln-Gln. This applies for any value of x, y, or z in the indicated ranges.

In some embodiments, the compound comprises a secondary structure which is an α-helix and R$_8$ is —H, allowing intrahelical hydrogen bonding. In some embodiments, at least one of A, B, C, D or E is an α,α-disubstituted amino acid. In one example, B is an α,α-disubstituted amino embodiments, at least one of A, B, C, D or E is

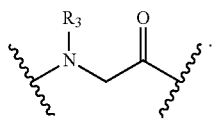

In other embodiments, the length of the macrocycle-forming linker L as measured from a first Cα to a second Cα is selected to stabilize a desired secondary peptide structure, such as an α-helix formed by residues of the compound including, but not necessarily limited to, those between the first Cα to a second Cα.

In some embodiments, the compound has the Formula (V) or Formula (Va):

Formula (V)

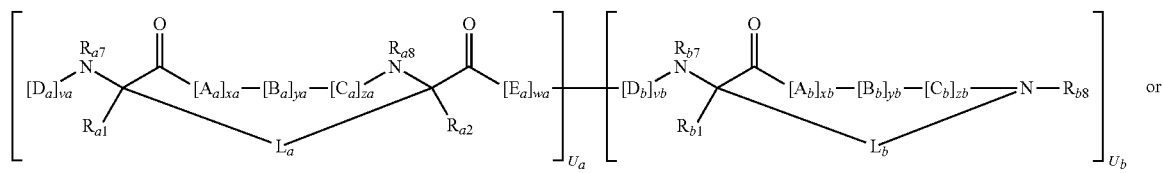

or

Formula (Va)

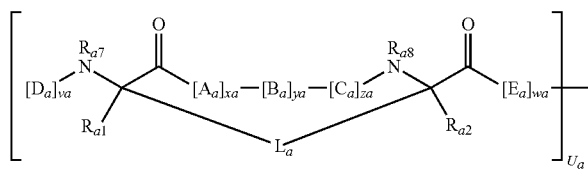

wherein:
each $A_a$, $C_a$, $D_a$, $E_a$, $A_b$, $C_b$, and $D_b$ is independently a natural or non-natural amino acid;
each $B_a$ and $B_b$ is independently a natural or non-natural amino acid,

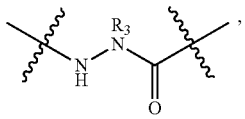

[—NH-$L_4$-CO—], [—NH-$L_4$-$SO_2$—], or [—NH-$L_4$-];
each $R_{a1}$ is independently, alkyl, alkenyl, alkynyl, arylalkyl, cycloalkyl, cycloalkylalkyl, heteroalkyl, or heterocycloalkyl, any of which is unsubstituted or substituted; or H; or $R_{a1}$ forms a macrocycle-forming linker L' connected to the alpha position of one of the $D_a$ or $E_a$ amino acids; or together with $L_a$ forms a ring that is unsubstituted or substituted;
each $R_{a2}$ is independently, alkyl, alkenyl, alkynyl, arylalkyl, cycloalkyl, cycloalkylalkyl, heteroalkyl, or heterocycloalkyl, any of which is unsubstituted or substituted; or H; or $R_{a2}$ forms a macrocycle-forming linker L' connected to the alpha position of one of the $D_a$ or $E_a$ amino acids; or together with $L_a$ forms a ring that is unsubstituted or substituted;
each $R_{b1}$ is independently, alkyl, alkenyl, alkynyl, arylalkyl, cycloalkyl, cycloalkylalkyl, heteroalkyl, or heterocycloalkyl, any of which is unsubstituted or substituted; or H; or $R_{b1}$ forms a macrocycle-forming linker L' connected to the alpha position of one of the $D_b$ amino acids; or together with $L_b$ forms a ring that is unsubstituted or substituted;
each $R_3$ is independently, alkyl, alkenyl, alkynyl, arylalkyl, heteroalkyl, cycloalkyl, heterocycloalkyl, cycloalkylalkyl, cycloaryl, or heterocycloaryl, any of which is unsubstituted or substituted, or H;
each $L_a$ is independently a macrocycle-forming linker, and optionally forms a ring with $R_{a1}$ or $R_{a2}$ that is unsubstituted or substituted;
each $L_b$ is independently a macrocycle-forming linker, and optionally forms a ring with $R_b$ that is unsubstituted or substituted;
each L' is independently a macrocycle-forming linker;
each $L_4$ is independently alkylene, alkenylene, alkynylene, heteroalkylene, cycloalkylene, heterocycloalkylene, cycloarylene, heterocycloarylene, or [—$R_4$—K—$R_4$-]$_n$, any of which is unsubstituted or substituted;
each $R_4$ is independently alkylene, alkenylene, alkynylene, heteroalkylene, cycloalkylene, heterocycloalkylene, arylene, or heteroarylene, any of which is unsubstituted or substituted;
each K is independently O, S, SO, $SO_2$, CO, $CO_2$, $OCO_2$, $NR_3$, $CONR_3$, $OCONR_3$, $OSO_2NR_3$, $NR_{3q}$, $CONR_{3q}$, $OCONR_{3q}$, or $OSO_2NR_{3q}$, wherein each $R_{3q}$ is independently a point of attachment to $R_{a1}$, $R_{a2}$, or $R_{b1}$;
each $R_{a7}$ is independently alkyl, alkenyl, alkynyl, arylalkyl, cycloalkyl, heteroalkyl, cycloalkylalkyl, heterocycloalkyl, cycloaryl, or heterocycloaryl, any of which is unsubstituted or substituted; or H; or part of a cyclic structure with a $D_a$ amino acid;
each $R_{b7}$ is independently alkyl, alkenyl, alkynyl, arylalkyl, cycloalkyl, heteroalkyl, cycloalkylalkyl, heterocycloalkyl, cycloaryl, or heterocycloaryl, any of which is unsubstituted or substituted; or H; or part of a cyclic structure with a $D_b$ amino acid;
each $R_{a8}$ is independently alkyl, alkenyl, alkynyl, arylalkyl, cycloalkyl, heteroalkyl, cycloalkylalkyl, heterocycloalkyl, cycloaryl, or heterocycloaryl, any of which is unsubstituted or substituted; or H; or part of a cyclic structure with an $E_a$ amino acid;
each $R_{b8}$ is independently alkyl, alkenyl, alkynyl, arylalkyl, cycloalkyl, heteroalkyl, cycloalkylalkyl, heterocycloalkyl, cycloaryl, or heterocycloaryl, any of which is unsubstituted or substituted; or H; or an amino acid sequence of 1-1000 amino acid residues;
each va and vb is independently an integer from 0-1000;
each wa and wb is independently an integer from 0-1000;
each ua and ub is independently 0, 1, 2, 3, 4, 5, 6, 7, 8, 9, or 10, wherein ua+ub is at least 1;
each xa and xb is independently 0, 1, 2, 3, 4, 5, 6, 7, 8, 9, or 10;
each ya and yb is independently 0, 1, 2, 3, 4, 5, 6, 7, 8, 9, or 10;
each za and zb is independently 0, 1, 2, 3, 4, 5, 6, 7, 8, 9, or 10; and
each n is independently 1, 2, 3, 4, or 5,
or a pharmaceutically-acceptable salt thereof.

In some embodiments, the compound of the invention has the formula defined above, wherein:
each $L_a$ is independently a macrocycle-forming linker of the formula -$L_1$-$L_2$-, and optionally forms a ring with $R_{a1}$ or $R_{a2}$ that is unsubstituted or substituted;
each $L_b$ is independently a macrocycle-forming linker of the formula -$L_1$-$L_2$-, and optionally forms a ring with $R_{b1}$ that is unsubstituted or substituted;
each L' is independently a macrocycle-forming linker of the formula -$L_1$-$L_2$-;
each $L_1$ and $L_2$ is independently alkylene, alkenylene, alkynylene, heteroalkylene, cycloalkylene, heterocycloalkylene, cycloarylene, heterocycloarylene, or [—$R_4$—K—$R_4$-]$_n$, any of which is unsubstituted or substituted;
each $R_4$ is independently alkylene, alkenylene, alkynylene, heteroalkylene, cycloalkylene, heterocycloalkylene, arylene, or heteroarylene, any of which is unsubstituted or substituted;
each K is independently O, S, SO, $SO_2$, CO, $CO_2$, $OCO_2$, $NR_3$, $CONR_3$, $OCONR_3$, $OSO_2NR_3$, $NR_{3q}$, $CONR_{3q}$, OCONR$_{3q}$, or OSO$_2$NR$_{3q}$, wherein each R$_{3q}$ is independently a point of attachment to R$_{a1}$, R$_{a2}$, or R$_{b1}$;
or a pharmaceutically-acceptable salt thereof.

In some embodiments, the compound has the formula defined above wherein each L$_a$ and L$_b$ is independently a triazole-containing macrocycle-forming linker. In some embodiments, the compound has the formula defined above, wherein:

each L$_a$ and L$_b$ is independently a macrocycle-forming linker of the formula:

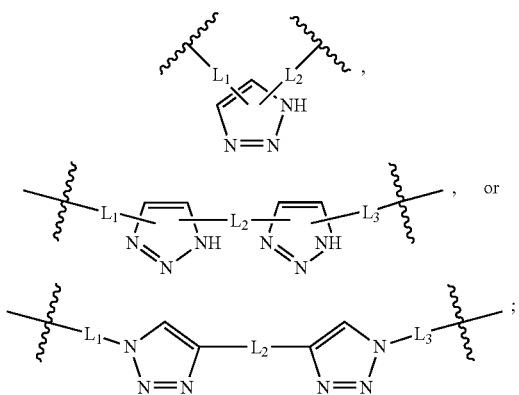

each L$_1$, L$_2$, and L$_3$ is independently alkylene, alkenylene, alkynylene, heteroalkylene, cycloalkylene, heterocycloalkylene, cycloarylene, heterocycloarylene, or [—R$_4$—K—R$_4$-]$_n$, any of which is unsubstituted or substituted;

each R$_4$ is independently alkylene, alkenylene, alkynylene, heteroalkylene, cycloalkylene, heterocycloalkylene, arylene, or heteroarylene, any of which is unsubstituted or substituted;

each K is independently O, S, SO, SO$_2$, CO, CO$_2$, OCO$_2$, NR$_3$, CONR$_3$, OCONR$_3$, OSO$_2$NR$_3$, NR$_{3q}$, CONR$_{3q}$, OCONR$_{3q}$, or OSO$_2$NR$_{3q}$, wherein each R$_{3q}$ is independently a point of attachment to R$_{a1}$, R$_{a2}$, or R$_{b1}$; and each n is independently 1, 2, 3, 4, or 5,
or a pharmaceutically-acceptable salt thereof.

In some embodiments, the compound has the formula defined above, wherein:

each L$_a$ and L$_b$ is independently a macrocycle-forming linker of the formula -L$_1$-SR$_9$R$_{10}$-L$_2$-SR$_{11}$R$_{12}$-L$_3$-, wherein each L$_1$, L$_2$, and L$_3$ is independently alkylene, alkenylene, alkynylene, heteroalkylene, cycloalkylene, heterocycloalkylene, cycloarylene, heterocycloarylene, or [—R$_4$—K—R$_4$-]$_n$, any of which is unsubstituted or substituted; and each R$_9$, R$_{10}$, R$_{11}$, and R$_{12}$ is independently absent or O;

each R$_4$ is independently alkylene, alkenylene, alkynylene, heteroalkylene, cycloalkylene, heterocycloalkylene, arylene, or heteroarylene, any of which is unsubstituted or substituted;

each K is independently O, S, SO, SO$_2$, CO, CO$_2$, OCO$_2$, NR$_3$, CONR$_3$, OCONR$_3$, OSO$_2$NR$_3$, NR$_{3q}$, CONR$_{3q}$, OCONR$_{3q}$, or OSO$_2$NR$_{3q}$, wherein each R$_{3q}$ is independently a point of attachment to R$_{a1}$, R$_{a2}$, or R$_{b1}$; and each n is independently 1, 2, 3, 4, or 5,
or a pharmaceutically-acceptable salt thereof.

In some embodiments, the compound has the formula defined above wherein one or both L$_a$ and L$_b$ is independently a bis-thioether-containing macrocycle-forming linker. In some embodiments, each L$_a$ and L$_b$ is independently a macrocycle-forming linker of the formula -L$_1$-S-L$_2$-S-L$_3$-.

In some embodiments, the compound has the formula defined above wherein one or both L$_a$ and L$_b$ is independently a bis-sulfone-containing macrocycle-forming linker. In some embodiments, each L$_a$ and L$_b$ is independently a macrocycle-forming linker of the formula -L$_1$-SO$_2$-L$_2$-SO$_2$-L$_3$-.

In some embodiments, the compound has the formula defined above wherein one or both L$_a$ and L$_b$ is independently a bis-sulfoxide-containing macrocycle-forming linker. In some embodiments, each L$_a$ and L$_b$ is independently a macrocycle-forming linker of the formula -L$_1$-S(O)-L$_2$-S(O)-L$_3$-.

In some embodiments, a compound of the invention comprises one or more secondary structures. In some embodiments, the compound comprises a secondary structure that is an α-helix. In some embodiments, the compound comprises a secondary structure that is a β-hairpin turn.

In some embodiments, u$_a$ is 0. In some embodiments, u$_a$ is 0, and L$_b$ is a triazole-containing macrocycle-forming linker that crosslinks an α-helical secondary structure. In some embodiments, u$_a$ is 0, and L$_b$ is a hydrocarbon-containing macrocycle-forming linker that crosslinks an α-helical secondary structure.

In some embodiments, u$_b$ is 0. In some embodiments, u$_b$ is 0, and L$_a$ is a triazole-containing macrocycle-forming linker that crosslinks an α-helical secondary structure. In some embodiments, u$_b$ is 0, and L$_a$ is a hydrocarbon-containing macrocycle-forming linker that crosslinks an α-helical secondary structure.

In some embodiments, the compound comprises only α-helical secondary structures.

In other embodiments, the compound comprises a combination of secondary structures, wherein the secondary structures are α-helical and β-hairpin structures. In some embodiments, L$_a$ and L$_b$ are a combination of hydrocarbon-, triazole, or sulfur-containing macrocycle-forming linkers. In some embodiments, the compound comprises L$_a$ and L$_b$, wherein L$_a$ is a hydrocarbon-containing macrocycle-forming linker that crosslinks a β-hairpin structure, and L$_b$ is a triazole-containing macrocycle-forming linker that crosslinks an α-helical structure. In some embodiments, the compound comprises L$_a$ and L$_b$, wherein L$_a$ is a hydrocarbon-containing macrocycle-forming linker that crosslinks an α-helical structure, and L$_b$ is a triazole-containing macrocycle-forming linker that crosslinks a β-hairpin structure. In some embodiments, the compound comprises L$_a$ and L$_b$, wherein L$_a$ is a triazole-containing macrocycle-forming linker that crosslinks an α-helical structure, and L$_b$ is a hydrocarbon-containing macrocycle-forming linker that crosslinks a β-hairpin structure. In some embodiments, the compound comprises L$_a$ and L$_b$, wherein L$_a$ is a triazole-containing macrocycle-forming linker that crosslinks a β-hairpin structure, and L$_b$ is a hydrocarbon-containing macrocycle-forming linker that crosslinks an α-helical structure.

In some embodiments, u$_a$+u$_b$ is at least 1. In some embodiments, u$_a$+u$_b$=2.

In some embodiments, u$_a$ is 1, and u$_b$ is 1. In some embodiments, u$_a$ is 1, u$_b$ is 1, L$_a$ is a triazole-containing macrocycle-forming linker that crosslinks an α-helical secondary structure, and L$_b$ is a triazole-containing macrocycle-forming linker that crosslinks an α-helical secondary structure. In some embodiments, u$_a$ is 1, u$_b$ is 1, L$_a$ is a triazole-containing macrocycle-forming linker that crosslinks an α-helical secondary structure, and $L_b$ is a triazole-containing macrocycle-forming linker that crosslinks a β-hairpin secondary structure. In some embodiments, $u_a$ is 1, $u_b$ is 1, $L_a$ is a triazole-containing macrocycle-forming linker that crosslinks a β-hairpin secondary structure, and $L_b$ is a triazole-containing macrocycle-forming linker that crosslinks an α-helical secondary structure.

In some embodiments, $u_a$ is 1, $u_b$ is 1, $L_a$ is a triazole-containing macrocycle-forming linker that crosslinks an α-helical secondary structure, and $L_b$ is a hydrocarbon-containing macrocycle-forming linker that crosslinks an α-helical structure. In some embodiments, $u_a$ is 1, $u_b$ is 1, $L_a$ is a triazole-containing macrocycle-forming linker that crosslinks an α-helical secondary structure, and $L_b$ is a hydrocarbon-containing macrocycle-forming linker that crosslinks a β-hairpin structure. In some embodiments, $u_a$ is 1, $u_b$ is 1, $L_a$ is a triazole-containing macrocycle-forming linker that crosslinks a β-hairpin secondary structure, and $L_b$ is a hydrocarbon-containing macrocycle-forming linker that crosslinks an α-helical structure.

In some embodiments, $u_a$ is 1, $u_b$ is 1, $L_a$ is a hydrocarbon-containing macrocycle-forming linker that crosslinks an α-helical secondary structure, and $L_b$ is a triazole-containing macrocycle-forming linker that crosslinks an α-helical secondary structure. In some embodiments, $u_a$ is 1, $u_b$ is 1, $L_a$ is a hydrocarbon-containing macrocycle-forming linker that crosslinks an α-helical secondary structure, and $L_b$ is a triazole-containing macrocycle-forming linker that crosslinks a β-hairpin secondary structure. In some embodiments, $u_a$ is 1, $u_b$ is 1, $L_a$ is a hydrocarbon-containing macrocycle-forming linker that crosslinks a β-hairpin secondary structure, and $L_b$ is a triazole-containing macrocycle-forming linker that crosslinks an α-helical secondary structure.

In some embodiments, $u_a$ is 1, $u_b$ is 1, $L_a$ is a triazole-containing macrocycle-forming linker that crosslinks an α-helical secondary structure, and $L_b$ is a sulfur-containing macrocycle-forming linker.

In some embodiments, $u_a$ is 1, $u_b$ is 1, $L_a$ is a sulfur-containing macrocycle-forming linker, and $L_b$ is a triazole-containing macrocycle-forming linker with an α-helical secondary structure.

In some embodiments, $u_a$ is 1, $u_b$ is 1, $L_a$ is a hydrocarbon-containing macrocycle-forming linker with an α-helical secondary structure, and $L_b$ is a sulfur-containing macrocycle-forming linker.

In some embodiments, $u_a$ is 1, $u_b$ is 1, $L_a$ is a sulfur-containing macrocycle-forming linker, and $L_b$ is a hydrocarbon-containing macrocycle-forming linker with an α-helical secondary structure.

In some embodiments, $u_a$ is 1, $u_b$ is 1, $L_a$ is a sulfur-containing macrocycle-forming linker, and $L_b$ is a sulfur-containing macrocycle-forming linker.

In some embodiments, $u_a$ is 1, $u_b$ is 1, $L_a$ is a hydrocarbon-containing macrocycle-forming linker that crosslinks an α-helical structure, and $L_b$ is a hydrocarbon-containing macrocycle-forming linker that crosslinks an α-helical structure. In some embodiments, $u_a$ is 1, $u_b$ is 1, $L_a$ is a hydrocarbon-containing macrocycle-forming linker that crosslinks an α-helical structure, and $L_b$ is a hydrocarbon-containing macrocycle-forming linker that crosslinks a β-hairpin structure. In some embodiments, $u_a$ is 1, $u_b$ is 1, $L_a$ is a hydrocarbon-containing macrocycle-forming linker that crosslinks a β-hairpin structure, and $L_b$ is a hydrocarbon-containing macrocycle-forming linker that crosslinks an α-helical structure.

In some embodiments, $R_{b1}$ is H.

In some embodiments, each v and w is 0, 1, 2, 3, 4, 5, 6, 7, 8, 9, 10, 11, 12, 13, 14, 15, 16, 17, 18, 19, or 20. In some embodiments, w is an integer from 3-1000, for example 3-500, 3-200, 3-100, 3-50, 3-30, 3-20, or 3-10. In some embodiments, the sum of x+y+z is 3 or 6. In some embodiments, the sum of x+y+z is 3. In other embodiments, the sum of x+y+z is 6.

Unless otherwise stated, any compounds (including compounds, macrocycle precursors, and other compositions) are also meant to encompass compounds which differ only in the presence of one or more isotopically enriched atoms. For example, compounds having the described structures except for the replacement of a hydrogen by a deuterium or tritium, or the replacement of a carbon by $^{13}$C- or $^{14}$C-enriched carbon are within the scope of this disclosure.

In some embodiments, the compounds disclosed herein can contain unnatural proportions of atomic isotopes at one or more of atoms that constitute such compounds. For example, the compounds can be radiolabeled with radioactive isotopes, such as for example tritium ($^3$H), iodine-125 ($^{125}$I) or carbon-14 ($^{14}$C). In other embodiments, one or more carbon atoms are replaced with a silicon atom. All isotopic variations of the compounds disclosed herein, whether radioactive or not, are contemplated herein.

A compound described herein can be at least 1% pure, at least 2% pure, at least 3% pure, at least 4% pure, at least 5% pure, at least 6% pure, at least 7% pure, at least 8% pure, at least 9% pure, at least 10% pure, at least 11% pure, at least 12% pure, at least 13% pure, at least 14% pure, at least 15% pure, at least 16% pure, at least 17% pure, at least 18% pure, at least 19% pure, at least 20% pure, at least 21% pure, at least 22% pure, at least 23% pure, at least 24% pure, at least 25% pure, at least 26% pure, at least 27% pure, at least 28% pure, at least 29% pure, at least 30% pure, at least 31% pure, at least 32% pure, at least 33% pure, at least 34% pure, at least 35% pure, at least 36% pure, at least 37% pure, at least 38% pure, at least 39% pure, at least 40% pure, at least 41% pure, at least 42% pure, at least 43% pure, at least 44% pure, at least 45% pure, at least 46% pure, at least 47% pure, at least 48% pure, at least 49% pure, at least 50% pure, at least 51% pure, at least 52% pure, at least 53% pure, at least 54% pure, at least 55% pure, at least 56% pure, at least 57% pure, at least 58% pure, at least 59% pure, at least 60% pure, at least 61% pure, at least 62% pure, at least 63% pure, at least 64% pure, at least 65% pure, at least 66% pure, at least 67% pure, at least 68% pure, at least 69% pure, at least 70% pure, at least 71% pure, at least 72% pure, at least 73% pure, at least 74% pure, at least 75% pure, at least 76% pure, at least 77% pure, at least 78% pure, at least 79% pure, at least 80% pure, at least 81% pure, at least 82% pure, at least 83% pure, at least 84% pure, at least 85% pure, at least 86% pure, at least 87% pure, at least 88% pure, at least 89% pure, at least 90% pure, at least 91% pure, at least 92% pure, at least 93% pure, at least 94% pure, at least 95% pure, at least 96% pure, at least 97% pure, at least 98% pure, at least 99% pure, at least 99.1% pure, at least 99.2% pure, at least 99.3% pure, at least 99.4% pure, at least 99.5% pure, at least 99.6% pure, at least 99.7% pure, at least 99.8% pure, or at least 99.9% pure on a chemical, optical, isomeric, enantiomeric, or diastereomeric basis. Purity can be assessed, for example, by HPLC, MS, LC/MS, melting point, or NMR.

Two or more peptides can share a degree of homology. A pair of peptides can have, for example, up to about 20% pairwise homology, up to about 25% pairwise homology, up to about 30% pairwise homology, up to about 35% pairwise homology, up to about 40% pairwise homology, up to about 45% pairwise homology, up to about 50% pairwise homology, up to about 55% pairwise homology, up to about 60% pairwise homology, up to about 65% pairwise homology, up to about 70% pairwise homology, up to about 75% pairwise homology, up to about 80% pairwise homology, up to about 85% pairwise homology, up to about 90% pairwise homology, up to about 95% pairwise homology, up to about 96% pairwise homology, up to about 97% pairwise homology, up to about 98% pairwise homology, up to about 99% pairwise homology, up to about 99.5% pairwise homology, or up to about 99.9% pairwise homology. A pair of peptides can have, for example, at least about 20% pairwise homology, at least about 25% pairwise homology, at least about 30% pairwise homology, at least about 35% pairwise homology, at least about 40% pairwise homology, at least about 45% pairwise homology, at least about 50% pairwise homology, at least about 55% pairwise homology, at least about 60% pairwise homology, at least about 65% pairwise homology, at least about 70% pairwise homology, at least about 75% pairwise homology, at least about 80% pairwise homology, at least about 85% pairwise homology, at least about 90% pairwise homology, at least about 95% pairwise homology, at least about 96% pairwise homology, at least about 97% pairwise homology, at least about 98% pairwise homology, at least about 99% pairwise homology, at least about 99.5% pairwise homology, at least about 99.9% pairwise homology.

Various methods and software programs can be used to determine the homology between two or more peptides, such as NCBI BLAST, Clustal W, MAFFT, Clustal Omega, AlignMe, Praline, or another suitable method or algorithm.

In some embodiments, the compound comprises at least one helical motif, such as a $3_{10}$ or an α-helix motif. For example, A, B and/or C in the compound of Formula I, II, or III include one or more helices. As a general matter, helices include from 3 to 4 amino acid residues per turn. In some embodiments, the helix of the compound includes 1 to 5 turns and, therefore, 3 to 20 amino acid residues. In specific embodiments, the helix includes 1 turn, 2 turns, 3 turns, 4 turns, or 5 turns. In some embodiments, the macrocycle-forming linker stabilizes a helix motif included within the compound. Thus, in some embodiments, the length of the macrocycle-forming linker L from a first α-carbon to a second α-carbon is selected to increase the stability of a helix. In some embodiments, the macrocycle-forming linker spans from 1 turn to 5 turns of the helix. In some embodiments, the macrocycle-forming linker spans approximately 1 turn, 2 turns, 3 turns, 4 turns, or 5 turns of the helix. In some embodiments, the length of the macrocycle-forming linker is approximately 5 Å to 9 Å per turn of the helix, or approximately 6 Å to 8 Å per turn of the helix. Where the macrocycle-forming linker spans approximately 1 turn of a helix, the length is equal to approximately 5 carbon-carbon bonds to 13 carbon-carbon bonds, approximately 7 carbon-carbon bonds to 11 carbon-carbon bonds, or approximately 9 carbon-carbon bonds. Where the macrocycle-forming linker spans approximately 2 turns of a helix, the length is equal to approximately 8 carbon-carbon bonds to 16 carbon-carbon bonds, approximately 10 carbon-carbon bonds to 14 carbon-carbon bonds, or approximately 12 carbon-carbon bonds. Where the macrocycle-forming linker spans approximately 3 turns of a helix, the length is equal to approximately 14 carbon-carbon bonds to 22 carbon-carbon bonds, approximately 16 carbon-carbon bonds to 20 carbon-carbon bonds, or approximately 18 carbon-carbon bonds. Where the macrocycle-forming linker spans approximately 4 turns of a helix, the length is equal to approximately 20 carbon-carbon bonds to 28 carbon-carbon bonds, approximately 22 carbon-carbon bonds to 26 carbon-carbon bonds, or approximately 24 carbon-carbon bonds. Where the macrocycle-forming linker spans approximately 5 turns of a helix, the length is equal to approximately 26 carbon-carbon bonds to 34 carbon-carbon bonds, approximately 28 carbon-carbon bonds to 32 carbon-carbon bonds, or approximately 30 carbon-carbon bonds. Where the macrocycle-forming linker spans approximately 1 turn of a helix, the linkage contains approximately 4 atoms to 12 atoms, approximately 6 atoms to 10 atoms, or approximately 8 atoms. Where the macrocycle-forming linker spans approximately 2 turns of the helix, the linkage contains approximately 7 atoms to 15 atoms, approximately 9 atoms to 13 atoms, or approximately 11 atoms. Where the macrocycle-forming linker spans approximately 3 turns of the helix, the linkage contains approximately 13 atoms to 21 atoms, approximately 15 atoms to 19 atoms, or approximately 17 atoms. Where the macrocycle-forming linker spans approximately 4 turns of the helix, the linkage contains approximately 19 atoms to 27 atoms, approximately 21 atoms to 25 atoms, or approximately 23 atoms. Where the macrocycle-forming linker spans approximately 5 turns of the helix, the linkage contains approximately 25 atoms to 33 atoms, approximately 27 atoms to 31 atoms, or approximately 29 atoms. Where the macrocycle-forming linker spans approximately 1 turn of the helix, the resulting macrocycle forms a ring containing approximately 17 members to 25 members, approximately 19 members to 23 members, or approximately 21 members. Where the macrocycle-forming linker spans approximately 2 turns of the helix, the resulting macrocycle forms a ring containing approximately 29 members to 37 members, approximately 31 members to 35 members, or approximately 33 members. Where the macrocycle-forming linker spans approximately 3 turns of the helix, the resulting macrocycle forms a ring containing approximately 44 members to 52 members, approximately 46 members to 50 members, or approximately 48 members. Where the macrocycle-forming linker spans approximately 4 turns of the helix, the resulting macrocycle forms a ring containing approximately 59 members to 67 members, approximately 61 members to 65 members, or approximately 63 members. Where the macrocycle-forming linker spans approximately 5 turns of the helix, the resulting macrocycle forms a ring containing approximately 74 members to 82 members, approximately 76 members to 80 members, or approximately 78 members.

In some embodiments, the stabilized peptides can have 5, 6, 7, 8, 9, 10, 11, 12, 13, 14, 15, 16, 17, 18, 19, 20, 21, 22, 23, 24, 25, 26, 27, 28, 29, or 30 amino acids. Peptides can contain one or more asymmetric centers and thus occur as racemates and racemic mixtures, single enantiomers, individual diastereomers and diastereomeric mixtures and geometric isomers (e.g. Z or cis and E or trans) of any olefins present. For example, peptides disclosed herein can exist in particular geometric or stereoisomeric forms, including, for example, cis- and trans-isomers, R- and S-enantiomers, diastereomers, (D)-isomers, (L)-isomers, the racemic mixtures thereof, and other mixtures thereof. Enantiomers can be free (e.g., substantially free) of their corresponding enantiomer, and/or may also be optically enriched. "Optically enriched," as used herein, means that the compound is made up of a significantly greater proportion of one enantiomer. In certain embodiments substantially free means that a composition contains at least about 90% by weight of a preferred enantiomer. In other embodiments the compound is made up of at least about 95%, 98%, or 99% by weight of a preferred enantiomer. Preferred enantiomers may be isolated from racemic mixtures using techniques known in the art, including, but not limited to, for example, chiral high pressure liquid chromatography (HPLC) and the formation and crystallization of chiral salts or prepared by asymmetric syntheses (see, e.g., Jacques, et al, Enantiomers, Racemates and Resolutions (Wiley Interscience, New York, 1981); Wilen, S. H., et al., Tetrahedron 33:2725 (1977); Eliel, EX. Stereochemistry of Carbon Compounds (McGraw-Hill, N Y, 1962); Wilen, S. H. Tables of Resolving Agents and Optical Resolutions p. 268 (EX. Eliel, Ed., Univ. of Notre Dame Press, Notre Dame, IN 1972). All such isomeric forms of these compounds are expressly included in the present invention.

Peptides can also be represented in multiple tautomeric forms, in such instances, the invention expressly includes all tautomeric forms of the compounds described herein (e.g., isomers in equilibrium (e.g., keto-enol), wherein alkylation at multiple sites can yield regioisomers), regioisomers, and oxidation products of the compounds disclosed herein (the invention expressly includes all such reaction products). All such isomeric forms of such compounds are included as are all crystal forms.

The term "halo" refers to any radical of fluorine, chlorine, bromine or iodine. The term "alkyl" refers to a hydrocarbon chain that may be a straight chain or branched chain, containing the indicated number of carbon atoms. For example, $C_1$-$C_{10}$ indicates that the group may have from 1 to 10 (inclusive) carbon atoms in it. In the absence of any numerical designation, "alkyl" is a chain (straight or branched) having 1 to 20 (inclusive) carbon atoms in it. The term "alkylene" refers to a divalent alkyl (i.e., —R—).

The term "alkenyl" refers to a hydrocarbon chain that may be a straight chain or branched chain having one or more carbon-carbon double bonds in either Z or E geometric configurations. The alkenyl moiety contains the indicated number of carbon atoms. For example, $C_2$-$C_{10}$ indicates that the group may have from 2 to 10 (inclusive) carbon atoms in it. The term "lower alkenyl" refers to a $C_2$-$C_8$ alkenyl chain. In the absence of any numerical designation, "alkenyl" is a chain (straight or branched) having 2 to 20 (inclusive) carbon atoms in it.

The term "alkynyl" refers to a hydrocarbon chain that may be a straight chain or branched chain having one or more carbon-carbon triple bonds. The alkynyl moiety contains the indicated number of carbon atoms. For example, $C_2$-$C_{10}$ indicates that the group may have from 2 to 10 (inclusive) carbon atoms in it. The term "lower alkynyl" refers to a $C_2$-$C_8$ alkynyl chain. In the absence of any numerical designation, "alkynyl" is a chain (straight or branched) having 2 to 20 (inclusive) carbon atoms in it.

The term "aryl" refers to a 6-carbon monocyclic or 10-carbon bicyclic aromatic ring system wherein 0, 1, 2, 3, 4, or 5 atoms of each ring may be substituted by a substituent. Examples of aryl groups include phenyl, naphthyl and the like. The term "arylalkyl" or the term "aralkyl" refers to alkyl substituted with an aryl. The term "arylalkoxy" refers to an alkoxy substituted with aryl.

The term "cycloalkyl" as employed herein includes saturated and partially unsaturated cyclic hydrocarbon groups having 3 to 12 carbons, preferably 3 to 8 carbons, and more preferably 3 to 6 carbons, wherein the cycloalkyl group additionally may be optionally substituted. Preferred cycloalkyl groups include, without limitation, cyclopropyl, cyclobutyl, cyclopentyl, cyclopentenyl, cyclohexyl, cyclohexenyl, cyclohexadienyl, cycloheptyl, cycloheptadienyl, cycloheptatrienyl, cyclooctyl, cyclooctenyl, cyclooctadienyl, cyclooctatrienyl, and cyclooctynyl.

The term "heteroaryl" refers to an aromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein 0, 1, 2, 3, or 4 atoms of each ring may be substituted by a substituent. Examples of heteroaryl groups include pyrrolyl, pyridyl, furyl or furanyl, imidazolyl, 1,2,3-triazolyl, 1,2,4-triazolyl, benzimidazolyl, pyridazyl, pyrimidyl, thiophenyl, quinolinyl, indolyl, thiazolyl, oxazolyl, isoxazolyl and the like. The term "heteroarylalkyl" or the term "heteroaralkyl" refers to an alkyl substituted with a heteroaryl. The term "heteroarylalkoxy" refers to an alkoxy substituted with heteroaryl.

The term "heterocyclyl" refers to a nonaromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein 0, 1, 2 or 3 atoms of each ring may be substituted by a substituent. Examples of heterocyclyl groups include piperazinyl, pyrrolidinyl, dioxanyl, aziridinyl, oxiryl, thiiryl, morpholinyl, tetrahydrofuranyl, and the like.

The term "substituents" refers to a group "substituted" on an alkyl, cycloalkyl, aryl, heterocyclyl, or heteroaryl group at any atom of that group. Suitable substituents include, without limitation, halo, hydroxy, mercapto, oxo, nitro, haloalkyl, alkyl, alkaryl, aryl, aralkyl, alkoxy, thioalkoxy, aryloxy, amino, alkoxycarbonyl, amido, carboxy, alkanesulfonyl, alkylcarbonyl, azido, and cyano groups.

While hydrocarbon tethers have been described, other tethers are also envisioned. For example, the tether can include one or more of an ether, thioether, ester, amine, or amide moiety. In some cases, a naturally occurring amino acid side chain can be incorporated into the tether. For example, a tether can be coupled with a functional group such as the hydroxyl in serine, the thiol in cysteine, the primary amine in lysine, the acid in aspartate or glutamate, or the amide in asparagine or glutamine. Accordingly, it is possible to create a tether using naturally occurring amino acids rather than using a tether that is made by coupling two non-naturally occurring amino acids. It is also possible to use a single non-naturally occurring amino acid together with a naturally occurring amino acid.

It is further envisioned that the length of the tether can be varied. For instance, a shorter length of tether can be used where it is desirable to provide a relatively high degree of constraint on the secondary alpha-helical structure, whereas, in some instances, it is desirable to provide less constraint on the secondary alpha-helical structure, and thus a longer tether may be desired.

Additionally, while examples of tethers spanning from amino acids i to i+3, i to i+4, and i to i+7 have been described in order to provide a tether that is primarily on a single face of the alpha helix, the tethers can be synthesized to span any combinations of numbers of amino acids.

In some instances, alpha disubstituted amino acids are used in the polypeptide to improve the stability of the alpha helical secondary structure. However, alpha disubstituted amino acids are not required, and instances using mono-alpha substituents (e.g., in the tethered amino acids) are also envisioned.

The stapled polypeptides can include a drug (e.g., an antibiotic; see below), a toxin, a derivative of polyethylene glycol; a second polypeptide; a carbohydrate, etc. Where a polymer or other agent is linked to the stapled polypeptide is can be desirable for the composition to be substantially homogeneous.

The addition of polyethelene glycol (PEG) moieties can improve the pharmacokinetic and pharmacodynamic properties of the polypeptide. For example, PEGylation can reduce renal clearance and can result in a more stable plasma concentration. PEG is a water soluble polymer and can be represented as linked to the polypeptide as formula:

$XO-(CH_2CH_2O)_n-CH_2CH_2-Y$ where n is 2 to 10,000 and X is H or a terminal modification, e.g., a $C_{1-4}$ alkyl; and Y is an amide, carbamate or urea linkage to an amine group (including but not limited to, the epsilon amine of lysine or the N-terminus) of the polypeptide. Y may also be a maleimide linkage to a thiol group (including but not limited to, the thiol group of cysteine). Other methods for linking PEG to a polypeptide, directly or indirectly, are known to those of ordinary skill in the art. The PEG can be linear or branched. Various forms of PEG including various functionalized derivatives are commercially available.

PEG having degradable linkages in the backbone can be used. For example, PEG can be prepared with ester linkages that are subject to hydrolysis. Conjugates having degradable PEG linkages are described, e.g., in WO 99/34833; WO 99/14259, and U.S. Pat. No. 6,348,558.

In certain embodiments, macromolecular polymer (e.g., PEG) is attached to an agent described herein through an intermediate linker. In certain embodiments, the linker is made up of from 1 to 20 amino acids linked by peptide bonds, wherein the amino acids are selected from the 20 naturally occurring amino acids. Some of these amino acids may be glycosylated, as is well understood by those in the art. In other embodiments, the 1 to 20 amino acids are selected from glycine, alanine, proline, asparagine, glutamine, and lysine. In other embodiments, a linker is made up of a majority of amino acids that are sterically unhindered, such as glycine and alanine. Non-peptide linkers are also possible. For example, alkyl linkers such as $-NH(CH_2)_nC(O)-$, wherein n=2-20 can be used. These alkyl linkers may further be substituted by any non-sterically hindering group such as lower alkyl (e.g., $C_1-C_6$) lower acyl, halogen (e.g., Cl, Br), CN, $NH_2$, phenyl, etc. U.S. Pat. No. 5,446,090 describes a bifunctional PEG linker and its use in forming conjugates having a peptide at each of the PEG linker termini.

Methods of synthesizing the compounds of the described herein are known in the art. Nevertheless, the following exemplary method may be used. It will be appreciated that the various steps may be performed in an alternate sequence or order to give the desired compounds. Synthetic chemistry transformations and protecting group methodologies (protection and deprotection) useful in synthesizing the compounds described herein are known in the art and include, e.g., those such as described in R. Larock, Comprehensive Organic Transformations, VCH Publishers (1989); T.W. Greene and P.G.M. Wuts, Protective Groups in Organic Synthesis, 3d. Ed., John Wiley and Sons (1999); L. Fieser and M. Fieser, Fieser and Fieser's Reagents for Organic Synthesis, John Wiley and Sons (1994); and L. Paquette, ed., Encyclopedia of Reagents for Organic Synthesis, John Wiley and Sons (1995), and subsequent editions thereof.

The peptides of this invention can be made by chemical synthesis methods, which are well known to the ordinarily skilled artisan. See, e.g., Fields et al., Chapter 3 in Synthetic Peptides: A User's Guide, ed. Grant, W. H. Freeman & Co., New York, N.Y., 1992, p. 77. Hence, peptides can be synthesized using the automated Merrifield techniques of solid phase synthesis with the $\alpha$-$NH_2$ protected by either t-Boc or Fmoc chemistry using side chain protected amino acids on, e.g., an Applied Biosystems Peptide Synthesizer™ Model 430A or 431.

One manner of making of the peptides described herein is using solid phase peptide synthesis (SPPS). The C-terminal amino acid is attached to a cross-linked polystyrene resin via an acid labile bond with a linker molecule. This resin is insoluble in the solvents used for synthesis, making it relatively simple and fast to wash away excess reagents and by-products. The N-terminus is protected with the Fmoc group, which is stable in acid, but removable by base. Any side chain functional groups are protected with base stable, acid labile groups.

Longer peptides could be made by conjoining individual synthetic peptides using native chemical ligation. Alternatively, the longer synthetic peptides can be synthesized by well-known recombinant DNA techniques. Such techniques are provided in well-known standard manuals with detailed protocols. To construct a gene encoding a peptide of this invention, the amino acid sequence is reverse translated to obtain a nucleic acid sequence encoding the amino acid sequence, preferably with codons that are optimum for the organism in which the gene is to be expressed. Next, a synthetic gene is made, typically by synthesizing oligonucleotides which encode the peptide and any regulatory elements, if necessary. The synthetic gene is inserted in a suitable cloning vector and transfected into a host cell. The peptide is then expressed under suitable conditions appropriate for the selected expression system and host. The peptide is purified and characterized by standard methods.

The peptides can be made in a high-throughput, combinatorial fashion, e.g., using a high-throughput multiple channel combinatorial synthesizer available from Advanced Chemtech.

Peptide bonds can be replaced, e.g., to increase physiological stability of the peptide, by: a retro-inverso bonds (C(O)—NH); a reduced amide bond (NH—$CH_2$); a thiomethylene bond (S—$CH_2$ or $CH_2$—S); an oxomethylene bond (O—$CH_2$ or $CH_2$—O); an ethylene bond ($CH_2$—$CH_2$); a thioamide bond (C(S)—NH); a trans-olefin bond (CH=CH); a fluoro substituted trans-olefin bond (CF=CH); a ketomethylene bond (C(O)—CHR) or CHR—C(O) wherein R is H or $CH_3$; and a fluoro-ketomethylene bond (C(O)—CFR or CFR—C(O) wherein R is H or F or $CH_3$.

The polypeptides can be further modified by: acetylation, amidation, biotinylation, cinnamoylation, farnesylation, fluoresceination, formylation, myristoylation, palmitoylation, phosphorylation (Ser, Tyr or Thr), stearoylation, succinylation and sulfurylation. As indicated above, peptides can be conjugated to, e.g., polyethylene glycol (PEG); alkyl groups (e.g., $C_1$-$C_{20}$ straight or branched alkyl groups); fatty acid radicals; and combinations thereof.

$\alpha,\alpha$-Disubstituted non-natural amino acids containing olefinic side chains of varying length can be synthesized by known methods (Williams et al. J. Am. Chem. Soc., 113: 9276, 1991; Schafmeister et al., J. Am. Chem Soc., 122: 5891, 2000; and Bird et al., Methods Enzymol., 446:369, 2008; Bird et al, Current Protocols in Chemical Biology, 2011). For peptides where an i linked to i+7 staple is used (two turns of the helix stabilized), either: a) one $S_5$ amino acid and one $R_8$ is used or b) one $S_8$ amino acid and one $R_5$ amino acid is used. $R_8$ is synthesized using the same route, except that the starting chiral auxiliary confers the R-alkyl-stereoisomer. Also, 8-iodooctene is used in place of 5-iodopentene. Inhibitors are synthesized on a solid support using solid-phase peptide synthesis (SPPS) on MBHA resin (see, e.g., WO 2010/148335).

Fmoc-protected α-amino acids (other than the olefinic amino acids Fmoc-$S_5$—OH, Fmoc-$R_8$—OH, Fmoc-$R_8$—OH, Fmoc-$S_5$—OH and Fmoc-$R_8$—OH), 2-(6-chloro-1-H-benzotriazole-1-yl)-1,1,3,3-tetramethylaminium hexafluorophosphate (HCTU), and Rink Amide MBHA are commercially available from, e.g., Novabiochem (San Diego, CA). Dimethylformamide (DMF), N-methyl-2-pyrrolidinone (NMP), N,N-diisopropylethylamine (DIEA), trifluoroacetic acid (TFA), 1,2-dichloroethane (DCE), fluorescein isothiocyanate (FITC), and piperidine are commercially available from, e.g., Sigma-Aldrich. Olefinic amino acid synthesis is reported in the art (see, e.g., Williams et al., Org. Synth., 80:31, 2003).

The compounds of this invention may be modified by appending appropriate functionalities to enhance selective biological properties (including, e.g., hydrophobicity and/or the position/occurrence of hydrophobic patches). Such modifications are known in the art and include those which increase biological penetration into a given biological compartment (e.g., blood, lymphatic system, central nervous system), increase oral availability, increase solubility to allow administration by injection, alter metabolism and alter rate of excretion.

An antimicrobial peptide selective for microbial versus mammalian membranes (i.e., a peptide able to kill or inhibit the growth of a microbe while also having a relatively low ability to lyse or inhibit the growth of a mammalian cell) may, e.g., possess a MIC for one or more microbes more than about 1.5-fold lower, more than about 2-fold lower, more than about 2.5-fold lower, more than about 3-fold lower, more than about 4-fold lower, more than about 5-fold lower, more than about 6-fold lower, more than about 7-fold lower, more than about 8-fold lower, more than about 9-fold lower, more than about 10-fold lower, more than about 15-fold lower, or more than about 20-fold lower than the MIC of the corresponding parent (i.e., unmodified) non-internally cross-linked peptide for the same one or more microbes. An antimicrobial peptide selective for microbial versus mammalian membranes can have a MIC of, for example, about 1 µg/ml, about 2 µg/ml, about 3 µg/ml, about 4 µg/ml, about 5 µg/ml, about 6 µg/ml, about 7 µg/ml, about 8 µg/ml, about 9 µg/ml, about 10 µg/ml, about 12 µg/ml, about 14 µg/ml, about 16 µg/ml, about 18 µg/ml, about 20 µg/ml, about 22 µg/ml, about 24 µg/ml, about 26 µg/ml, about 28 µg/ml, or about 30 µg/ml.

In addition, an antimicrobial peptide selective for microbial versus mammalian membranes may lyse, e.g., less than about 50%, less than about 40%, less than about 30%, less than about 25%, less than about 20%, less than about 15%, less than about 10%, less than about 5%, less than about 2.5%, less than about 2%, or less than about 1% of red blood cells (RBCs) in a RBC hemolytic activity assay when administered at its MIC for one or more microbes. An antimicrobial peptide selective for microbial versus mammalian membranes may lyse, e.g., less than about 50%, less than about 40%, less than about 30%, less than about 25%, less than about 20%, less than about 15%, less than about 10%, less than about 5%, less than about 2.5%, less than about 2%, or less than about 1% of red blood cells (RBCs) in a RBC hemolytic activity assay when administered at a concentration, e.g., greater than or approximately equal to 1.5-fold, 2-fold, 2.5-fold, 3-fold, 4-fold, 5-fold, 6-fold, 7-fold, 8-fold, 9-fold, or 10-fold its MIC for one or more microbes. The RBC hemolytic activity of an antimicrobial peptide selective for microbial versus mammalian membranes may be less than, approximately equal to, less than 1.5-fold greater, less than 2-fold greater, less than 2.5-fold greater, less than 3-fold greater, less than 4-fold greater, less than 5-fold greater, less than 6-fold greater, less than 7-fold greater, less than 8-fold greater, less than 9-fold greater, or less than 10-fold greater than the RBC hemolytic activity of the corresponding parent (i.e., unmodified) non-internally cross-linked peptide.

Hydrophobic patches within a peptide or protein may be identified using techniques generally known in the art, including, e.g., computational prediction/simulation (e.g., using ExPASy ProtScale, Scooby-domain prediction, PSIPRED, hydrophobic cluster analysis, Kyte Doolittle plotting, and/or SPLIT) and/or experimental determination (e.g., using techniques involving NMR spectroscopy, electron microscopy, homology modeling, small-angle X-ray and/or neutron scattering (SAXS/SANS), and/or X-ray crystallography) of the structure of the peptide or protein.

Pharmaceutically acceptable salts of the compounds of this invention include those derived from pharmaceutically acceptable inorganic and organic acids and bases. Examples of suitable acid salts include acetate, adipate, benzoate, benzenesulfonate, butyrate, citrate, digluconate, dodecylsulfate, formate, fumarate, glycolate, hemisulfate, heptanoate, hexanoate, hydrochloride, hydrobromide, hydroiodide, lactate, maleate, malonate, methanesulfonate, 2-naphthalenesulfonate, nicotinate, nitrate, palmoate, phosphate, picrate, pivalate, propionate, salicylate, succinate, sulfate, tartrate, tosylate, trifluoromethylsulfonate, and undecanoate. Salts derived from appropriate bases include alkali metal (e.g., sodium), alkaline earth metal (e.g., magnesium), ammonium and N-(alkyl)4+ salts. This invention also envisions the quaternization of any basic nitrogen-containing groups of the compounds disclosed herein. Water or oil-soluble or dispersible products may be obtained by such quaternization.

Methods suitable for obtaining (e.g., synthesizing), stapling, and purifying the peptides disclosed herein are also known in the art (see, e.g., Bird et. al., Methods in Enzymol., 446:369-386 (2008); Bird et al, Current Protocols in Chemical Biology, 2011; Walensky et al., Science, 305:1466-1470 (2004); Schafmeister et al., J. Am. Chem. Soc., 122:5891-5892 (2000); U.S. patent application Ser. No. 12/525,123, filed Mar. 18, 2010; and U.S. Pat. No. 7,723,468, issued May 25, 2010, each of which are hereby incorporated by reference in their entirety) and are described herein.

In some embodiments, the peptides are substantially free of non-stapled peptide contaminants or are isolated. Methods for purifying peptides include, for example, synthesizing the peptide on a solid-phase support. Following cyclization, the solid-phase support may be isolated and suspended in a solution of a solvent such as DMSO, DMSO/dichloromethane mixture, or DMSO/NMP mixture. The DMSO/dichloromethane or DMSO/NMP mixture may comprise about 30%, 40%, 50%, or 60% DMSO. In a specific embodiment, a 50%/50% DMSO/NMP solution is used. The solution may be incubated for a period of 1, 6, 12 or 24 hours, following which the resin may be washed, for example with dichloromethane or NMP. In one embodiment, the resin is washed with NMP. Shaking and bubbling an inert gas into the solution may be performed.

Properties of the cross-linked polypeptides of the invention can be assayed, for example, using the methods described below.

Assays to Determine α-Helicity:

Compounds are dissolved in an aqueous solution (e.g. 5 mM potassium phosphate solution at pH 7, or distilled $H_2O$, to concentrations of 25-50 µM). Circular dichroism (CD) spectra are obtained on a spectropolarimeter (e.g., Jasco J-710, Aviv) using standard measurement parameters (e.g. temperature, 20° C.; wavelength, 190-260 nm; step resolution, 0.5 nm; speed, 20 nm/sec; accumulations, 10; response, 1 sec; bandwidth, 1 nm; path length, 0.1 cm). The α-helical content of each peptide is calculated by dividing the mean residue ellipticity by the reported value for a model helical decapeptide (Yang et al., Methods Enzymol. 130:208 (1986)).

Assays to Determine Melting Temperature (Tm):

Cross-linked or the unmodified template peptides are dissolved in distilled $H_2O$ or other buffer or solvent (e.g. at a final concentration of 50 µM) and Tm is determined by measuring the change in ellipticity over a temperature range (e.g. 4 to 95° C.) on a spectropolarimeter (e.g., Jasco J-710, Aviv) using standard parameters (e.g. wavelength 222 nm; step resolution, 0.5 nm; speed, 20 nm/sec; accumulations, 10; response, 1 sec; bandwidth, 1 nm; temperature increase rate: 1° C./min; path length, 0.1 cm).

In Vitro Protease Resistance Assays:

The amide bond of the peptide backbone is susceptible to hydrolysis by proteases, thereby rendering peptidic compounds vulnerable to rapid degradation in vivo. Peptide helix formation, however, typically buries and/or twists and/or shields the amide backbone and therefore may prevent or substantially retard proteolytic cleavage. The peptidomimetic macrocycles of the present invention may be subjected to in vitro enzymatic proteolysis (e.g. trypsin, chymotrypsin, pepsin) to assess for any change in degradation rate compared to a corresponding uncrosslinked or alternatively stapled polypeptide. For example, the peptidomimetic macrocycle and a corresponding uncrosslinked polypeptide are incubated with trypsin agarose and the reactions quenched at various time points by centrifugation and subsequent HPLC injection to quantitate the residual substrate by ultraviolet absorption at 280 nm. Briefly, the peptidomimetic macrocycle and peptidomimetic precursor (5 mcg) are incubated with trypsin agarose (Pierce) (S/E~125) for 0, 10, 20, 90, and 180 minutes. Reactions are quenched by tabletop centrifugation at high speed; remaining substrate in the isolated supernatant is quantified by HPLC-based peak detection at 280 nm. The proteolytic reaction displays first order kinetics and the rate constant, k, is determined from a plot of ln[S] versus time.

Peptidomimetic macrocycles and/or a corresponding uncrosslinked polypeptide can be each incubated with fresh mouse, rat and/or human serum (e.g. 1-2 mL) at 37° C. for, e.g., 0, 1, 2, 4, 8, and 24 hours. Samples of differing macrocycle concentration may be prepared by serial dilution with serum. To determine the level of intact compound, the following procedure may be used: The samples are extracted, for example, by transferring 100 µL of sera to 2 ml centrifuge tubes followed by the addition of 10 µL of 50% formic acid and 500 µL acetonitrile and centrifugation at 14,000 RPM for 10 min at 4+/−2° C. The supernatants are then transferred to fresh 2 ml tubes and evaporated on Turbovap under $N_2$<10 psi, 37° C. The samples are reconstituted in 100 µL of 50:50 acetonitrile:water and submitted to LC-MS/MS analysis. Equivalent or similar procedures for testing ex vivo stability are known and may be used to determine stability of macrocycles in serum.

In Vivo Protease Resistance Assays: A key benefit of peptide stapling is the translation of in vitro protease resistance into markedly improved pharmacokinetics in vivo. Structurally-stabilized I-TAMPs with potent and selective antimicrobial activity are screened for protease stability in vivo, e.g., using previously published methods (see, e.g., Bird et al, PNAS, 2010).

Pharmaceutical Compositions

One or more of the stabilized peptides disclosed herein (e.g., those derived from I-TAMPs having one or more of SEQ ID NOs: 1-13, including SEQ ID NOs: 14-36) can be formulated for use as or in pharmaceutical compositions. Such compositions can be formulated or adapted for administration to a subject via any route, e.g., any route approved by the Food and Drug Administration (FDA). Exemplary methods are described in the FDA Data Standards Manual (DSM).

The pharmaceutical compositions of this invention may be administered, e.g., orally, parenterally, by inhalation spray or nebulizer, topically, rectally, nasally, buccally, vaginally, via an implanted reservoir, by injection (e.g., intravenously, intra-arterially, subdermally, intraperitoneally, intramuscularly, and/or subcutaneously), in an ophthalmic preparation, or via transmucosal administration. Suitable dosages may range from about 0.001 to about 100 mg/kg of body weight, or according to the requirements of the particular drug. The pharmaceutical compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intraarticular, intra-arterial, intrasynovial, intrasternal, intrathecal, intralesional and intracranial injection or infusion techniques. Alternatively or in addition, the present invention may be administered according to any of the methods as described in the FDA DSM.

As used herein, the compounds of this invention, including the compounds of formulae described herein, are defined to include pharmaceutically acceptable derivatives or prodrugs thereof. A "pharmaceutically acceptable derivative or prodrug" means any pharmaceutically acceptable salt, ester, salt of an ester, or other derivative of a compound or agent disclosed herein which, upon administration to a recipient, is capable of providing (directly or indirectly) a compound of this invention. Particularly favored derivatives and prodrugs are those that increase the bioavailability of the compounds of this invention when such compounds are administered to a mammal (e.g., by allowing an orally administered compound to be more readily absorbed into the blood) or which enhance delivery of the parent compound to a biological compartment (e.g., the brain or lymphatic system) relative to the parent species. Preferred prodrugs include derivatives where a group which enhances aqueous solubility or active transport through the gut membrane is appended to the structure of formulae described herein.

In some instances, pharmaceutical compositions can include an effective amount of one or more stabilized peptides. The terms "effective amount" and "effective to treat," as used herein, refer to an amount or a concentration of one or more compounds or a pharmaceutical composition described herein utilized for a period of time (including acute or chronic administration and periodic or continuous administration) that is effective within the context of its administration for causing an intended effect or physiological outcome (e.g., treatment of infection).

The methods herein contemplate administration of an effective amount of compound or compound composition to achieve the desired or stated effect. Typically, the pharmaceutical compositions of this invention will be administered from about 1 to about 6 times per day or alternatively, as a continuous infusion. Such administration can be used as a chronic or acute therapy. The amount of active ingredient that may be combined with the carrier materials to produce a single dosage form will vary depending upon the host treated and the particular mode of administration. A typical preparation will contain from about 5% to about 95% active compound (w/w). Alternatively, such preparations contain from about 20% to about 80% active compound.

Dosing can be determined using various techniques. The selected dosage level can depend upon a variety of factors including the activity of the particular compound employed, the route of administration, the time of administration, the rate of excretion or metabolism of the particular compound being employed, the duration of the treatment, other drugs, compounds and/or materials used in combination with the particular compound employed, the age, sex, weight, condition, general health and prior medical history of the patient being treated, and like factors well known in the medical arts. The dosage values can also vary with the severity of the condition to be alleviated. For any particular subject, specific dosage regimens can be adjusted over time according to the individual need and the professional judgment of the person administering or supervising the administration of the compositions.

In some embodiments, a suitable daily dose of a compound of the disclosure can be that amount of the compound which is the lowest dose effective to produce a therapeutic effect. Such an effective dose will generally depend upon the factors described above. The precise time of administration and amount of any particular compound that will yield the most effective treatment in a given patient will depend upon the activity, pharmacokinetics, and bioavailability of a particular compound, physiological condition of the patient (including age, sex, disease type and stage, general physical condition, responsiveness to a given dosage and type of medication), route of administration, and the like.

A physician or veterinarian can prescribe the effective amount of the pharmaceutical composition required. For example, the physician or veterinarian could start doses of the compounds of the disclosure employed in the pharmaceutical composition at levels lower than that required in order to achieve the desired therapeutic effect and gradually increase the dosage until the desired effect is achieved.

Pharmaceutical compositions described herein can be in unit dosage forms suitable for single administration of precise dosages. In unit dosage form, the formulation is divided into unit doses containing appropriate quantities of one or more compounds. The unit dosage can be in the form of a package containing discrete quantities of the formulation. Non-limiting examples are liquids in vials or ampoules. Aqueous suspension compositions can be packaged in single-dose non-reclosable containers. Multiple-dose reclosable containers can be used, for example, in combination with a preservative. Formulations for parenteral injection can be presented in unit dosage form, for example, in ampoules, or in multi dose containers with a preservative.

A compound described herein can be present in a composition in a range of from about 1 mg to about 2000 mg; from about 100 mg to about 2000 mg; from about 10 mg to about 2000 mg; from about 5 mg to about 1000 mg, from about 10 mg to about 500 mg, from about 50 mg to about 250 mg, from about 100 mg to about 200 mg, from about 1 mg to about 50 mg, from about 50 mg to about 100 mg, from about 100 mg to about 150 mg, from about 150 mg to about 200 mg, from about 200 mg to about 250 mg, from about 250 mg to about 300 mg, from about 300 mg to about 350 mg, from about 350 mg to about 400 mg, from about 400 mg to about 450 mg, from about 450 mg to about 500 mg, from about 500 mg to about 550 mg, from about 550 mg to about 600 mg, from about 600 mg to about 650 mg, from about 650 mg to about 700 mg, from about 700 mg to about 750 mg, from about 750 mg to about 800 mg, from about 800 mg to about 850 mg, from about 850 mg to about 900 mg, from about 900 mg to about 950 mg, or from about 950 mg to about 1000 mg.

A compound described herein can be present in a composition in an amount of about 1 mg, about 2 mg, about 3 mg, about 4 mg, about 5 mg, about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 125 mg, about 150 mg, about 175 mg, about 200 mg, about 250 mg, about 300 mg, about 350 mg, about 400 mg, about 450 mg, about 500 mg, about 550 mg, about 600 mg, about 650 mg, about 700 mg, about 750 mg, about 800 mg, about 850 mg, about 900 mg, about 950 mg, about 1000 mg, about 1050 mg, about 1100 mg, about 1150 mg, about 1200 mg, about 1250 mg, about 1300 mg, about 1350 mg, about 1400 mg, about 1450 mg, about 1500 mg, about 1550 mg, about 1600 mg, about 1650 mg, about 1700 mg, about 1750 mg, about 1800 mg, about 1850 mg, about 1900 mg, about 1950 mg, or about 2000 mg.

In some embodiments, a dose can be expressed in terms of an amount of the drug divided by the mass of the subject, for example, milligrams of drug per kilograms of subject body mass. In some embodiments, a compound is administered in an amount ranging from about 5 mg/kg to about 50 mg/kg, 250 mg/kg to about 2000 mg/kg, about 10 mg/kg to about 800 mg/kg, about 50 mg/kg to about 400 mg/kg, about 100 mg/kg to about 300 mg/kg, or about 150 mg/kg to about 200 mg/kg.

Dosage can be based on the amount of the compound per kg body weight of the patient. Alternatively, the dosage of the subject disclosure can be determined by reference to the plasma concentrations of the compound. For example, the maximum plasma concentration (Cmax) and the area under the plasma concentration-time curve from time 0 to infinity (AUC) can be used.

In some embodiments, the subject is a human subject and the amount of the compound administered is 0.01-100 mg per kilogram body weight of the human subject. For example, in various examples, the amount of the compound administered is about 0.01-50 mg/kg, about 0.01-20 mg/kg, about 0.01-10 mg/kg, about 0.1-100 mg/kg, about 0.1-50 mg/kg, about 0.1-20 mg/kg, about 0.1-10 mg/kg, about 0.5-100 mg/kg, about 0.5-50 mg/kg, about 0.5-20 mg/kg, about 0.5-10 mg/kg, about 1-100 mg/kg, about 1-50 mg/kg, about 1-20 mg/kg, about 1-10 mg/kg body weight of the human subject. In one embodiment, about 0.5 mg-10 mg of the compound per kilogram body weight of the human subject is administered. In some examples the amount of the compound administered is about 0.16 mg, about 0.32 mg, about 0.64 mg, about 1.28 mg, about 3.56 mg, about 7.12 mg, about 14.24 mg, or about 20 mg per kilogram body weight of the human subject. In some examples the amount of the compound administered is about 0.16 mg, about 0.32 mg, about 0.64 mg, about 1.28 mg, about 3.56 mg, about 7.12 mg, or about 14.24 mg per kilogram body weight of the human subject. In some examples the amount of the compound administered is about 0.16 mg per kilogram body weight of the human subject. In some examples the amount of the compound administered is about 0.32 mg per kilogram body weight of the human subject. In some examples the amount of the compound administered is about 0.64 mg per kilogram body weight of the human subject. In some examples the amount of the compound administered is about 1.28 mg per kilogram body weight of the human subject. In some examples the amount of the compound administered is about 3.56 mg per kilogram body weight of the human subject. In some examples the amount of the compound administered is about 7.12 mg per kilogram body weight of the human subject. In some examples the amount of the compound administered is about 14.24 mg per kilogram body weight of the human subject.

In some embodiments about 0.5-about 20 mg or about 0.5-about 10 mg of the compound per kilogram body weight of the human subject is administered two times a week. For example about 0.5-about 1 mg, about 0.5-about 5 mg, about 0.5-about 10 mg, about 0.5-about 15 mg, about 1-about 5 mg, about 1-about 10 mg, about 1-about 15 mg, about 1-about 20 mg, about 5-about 10 mg, about 1-about 15 mg, about 5-about 20 mg, about 10-about 15 mg, about 10-about 20 mg, or about 15-about 20 mg of the compound per kilogram body weight of the human subject is administered about twice a week. In some examples, about 1 mg, about 1.5 mg, about 2 mg, about 2.5 mg, about 3 mg, about 3.5 mg, about 4 mg, about 4.5 mg, about 5 mg, about 5.5 mg, about 6 mg, about 6.5 mg, about 7 mg, about 7.5 mg, about 8 mg, about 8.5 mg, about 9 mg, about 9.5 mg, about 10 mg, about 10.5 mg, about 11 mg, about 11.5 mg, about 12 mg, about 12.5 mg, about 13 mg, about 13.5 mg, about 14 mg, about 14.5 mg, about 15 mg, about 15.5 mg, about 16 mg, about 16.5 mg, about 17 mg, about 17.5 mg, about 18 mg, about 18.5 mg, about 19 mg, about 19.5 mg, or about 20 mg of the compound per kilogram body weight of the human subject is administered two times a week. In some examples, the amount of the compound administered is about 1.25 mg, about 2.5 mg, about 5 mg, about 10 mg, or about 20 mg per kilogram body weight of the human subject and the compound is administered two times a week. In some examples, the amount of the compound administered is about 1.25 mg, about 2.5 mg, about 5 mg or about 10 mg per kilogram body weight of the human subject. The compound can be administered once a week, two times a week, three, four, five, six, or seven times a week. The compound can be administered once every 3 weeks.

In some embodiments, the compound is administered gradually over a period of time. A desired amount of compound can, for example can be administered gradually over a period of from about 0.1 h-24 h. In some cases, a desired amount of compound is administered gradually over a period of 0.1 h, 0.5 h, 1 h, 1.5 h, 2 h, 2.5 h, 3 h, 3.5 h, 4 h, 4.5 h, 5 h, 6 h, 7 h, 8 h, 9 h, 10 h, 11 h, 12 h, 13 h, 14 h, 15 h, 16 h, 17 h, 18 h, 19 h, 20 h, 21 h, 22 h, 23 h, or 24 h. In some examples, a desired amount of compound is administered gradually over a period of 0.25-12 h, for example over a period of 0.25-1 h, 0.25-2 h, 0.25-3 h, 0.25-4 h, 0.25-6 h, 0.25-8 h, or 0.25-10 h. In some examples, a desired amount of compound is administered gradually over a period of 0.25-2 h. In some examples, a desired amount of compound is administered gradually over a period of 0.25-1 h. In some examples, a desired amount of compound is administered gradually over a period of 0.25 h, 0.3 h, 0.4 h, 0.5 h, 0.6 h, 0.7 h, 0.8 h, 0.9 h, 1.0 h, 1.1 h, 1.2 h, 1.3 h, 1.4 h, 1.5 h, 1.6 h, 1.7 h, 1.8 h, 1.9 h, or 2.0 h. In some examples, a desired amount of compound is administered gradually over a period of 1 h. In some examples, a desired amount of compound is administered gradually over a period of 2 h.

Administration of the compounds can continue as long as necessary. In some embodiments, one or more compound of the disclosure is administered for more than 1 day, more than 1 week, more than 1 month, more than 2 months, more than 3 months, more than 4 months, more than 5 months, more than 6 months, more than 7 months, more than 8 months, more than 9 months, more than 10 months, more than 11 months, more than 12 months, more than 13 months, more than 14 months, more than 15 months, more than 16 months, more than 17 months, more than 18 months, more than 19 months, more than 20 months, more than 21 months, more than 22 months, more than 23 months, or more than 24 months. In some embodiments, one or more compound of the disclosure is administered for less than 1 week, less than 1 month, less than 2 months, less than 3 months, less than 4 months, less than 5 months, less than 6 months, less than 7 months, less than 8 months, less than 9 months, less than 10 months, less than 11 months, less than 12 months, less than 13 months, less than 14 months, less than 15 months, less than 16 months, less than 17 months, less than 18 months, less than 19 months, less than 20 months, less than 21 months, less than 22 months, less than 23 months, or less than 24 months.

In some embodiments, the compound is administered on day 1, 8, 15, and 28 of a 28 day cycle. In some embodiments, the compound is administered on day 1, 8, 15, and 28 of a 28 day cycle and administration is continued for two cycles. In some embodiments, the compound is administered on day 1, 8, 15, and 28 of a 28 day cycle and administration is continued for three cycles. In some embodiments, the compound is administered on day 1, 8, 15, and 28 of a 28 day cycle and administration is continued for 4, 5, 6, 7, 8, 9, 10, or more cycles.

In some embodiments, the compound is administered on day 1, 8, 11, and 21 of a 21-day cycle. In some embodiments, the compound is administered on day 1, 8, 11, and 21 of a 21-day cycle and administration is continued for two cycles. In some embodiments, the compound is administered on day 1, 8, 11, and 21 of a 21-day cycle and administration is continued for three cycles. In some embodiments, the compound is administered on day 1, 8, 11, and 21 of a 21-day cycle and administration is continued for 4, 5, 6, 7, 8, 9, 10, or more cycles.

In some embodiments, one or more compound of the disclosure is administered chronically on an ongoing basis. In some embodiments administration of one or more compound of the disclosure is continued until documentation of disease progression, unacceptable toxicity, or patient or physician decision to discontinue administration. In some embodiments, an effective dose of a stapled AMP can include, but is not limited to, e.g., about, 0.00001, 0.0001, 0.001, 0.01, 0.1, 1 or 10-10000; 0.00001, 0.0001, 0.001, 0.01, 0.1, 1 or 10-5000; 0.00001, 0.0001, 0.001, 0.01, 0.1, 1 or 10-2500; 0.00001, 0.0001, 0.001, 0.01, 0.1, 1 or 10-1000; 0.00001, 0.0001, 0.001, 0.01, 0.1, 1 or 10-900; 0.00001, 0.0001, 0.001, 0.01, 0.1, 1 or 10-800; 0.00001, 0.0001, 0.001, 0.01, 0.1, 1 or 10-700; 0.00001, 0.0001, 0.001, 0.01, 0.1, 1 or 10-600; 0.00001, 0.0001, 0.001, 0.01, 0.1, 1 or 10-500; 0.00001, 0.0001, 0.001, 0.01, 0.1, 1 or 10-400; 0.00001, 0.0001, 0.001, 0.01, 0.1, 1 or 10-300; 0.00001, 0.0001, 0.001, 0.01, 0.1, 1 or 10-200; 0.00001, 0.0001, 0.001, 0.01, 0.1, 1 or 10-100; 0.00001, 0.0001, 0.001, 0.01, 0.1, 1 or 10-90; 0.00001, 0.0001, 0.001, 0.01, 0.1, 1 or 10-80; 0.00001, 0.0001, 0.001, 0.01, 0.1, 1 or 10-70;

0.00001, 0.0001, 0.001, 0.01, 0.1, 1 or 10-60; 0.00001, 0.0001, 0.001, 0.01, 0.1, 1 or 10-50; 0.00001, 0.0001, 0.001, 0.01, 0.1, 1 or 10-40; 0.00001, 0.0001, 0.001, 0.01, 0.1, 1 or 10-30; 0.00001, 0.0001, 0.001, 0.01, 0.1, 1 or 10-20; 0.00001, 0.0001, 0.001, 0.01, 0.1, 1 or 10-30; 0.00001, 0.0001, 0.001, 0.01, 0.1, 1-15, 0.00001, 0.0001, 0.001, 0.01, 0.1, 1 or 10-30; 0.00001, 0.0001, 0.001, 0.01, 0.1, 1-10, 0.00001, 0.0001, 0.001, 0.01, 0.1, 1 or 10-30; or 0.00001, 0.0001, 0.001, 0.01, 0.1, 1-5 mg/kg/day.

Pharmaceutical compositions of this invention can include one or more peptides and any pharmaceutically acceptable carrier and/or vehicle. In some instances, pharmaceuticals can further include one or more additional therapeutic agents in amounts effective for achieving a modulation of disease or disease symptoms. Appropriate therapeutic agents can also be administered chemically (covalently or non-covalently) bound to the stabilized I-TAMPs of this document Such additional therapeutic agents may include antimicrobial agents (e.g., antibiotics) known in the art. When co-administered, stapled AMPs of the invention operate in conjunction with antimicrobial agents to produce mechanistically additive or synergistic antimicrobial effects.

Examples of antibiotics suitable for co-administration with (as separate entities or chemically bound (covalently or non-covalently) to) the stapled peptides disclosed herein (as separate agents or chemically bound to the stapled peptides) include, but are not limited to, quinolones (e.g., levofloxacin, norfloxacin, ofloxacin, ciprofloxacin, perfloxacin, lomefloxacin, fleroxacin, sparfloxacin, grepafloxacin, trovafloxacin, clinafloxacin, gemifloxacin, enoxacin, sitafloxacin, nadifloxacin, tosulfloxacin, cinnoxacin, rosoxacin, miloxacin, moxifloxacin, gatifloxacin, cinnoxacin, enoxacin, fleroxacin, lomafloxacin, lomefloxacin, miloxacin, nalidixic acid, nadifloxacin, oxolinic acid, pefloxacin, pirimidic acid, pipemidic acid, rosoxacin, rufloxacin, temafloxacin, tosufloxacin, trovafloxacin, besifloxacin); β-lactams including cephalosporins (e.g., cefacetrile, cefixime, cefadroxil, cefaloglycin, cefalonium, cefaloridine, cefalotin, cefapirin, cefcapene, cefdaloxime, cefdinir, cefditoren, cefatrizine, cefetamet, cefazaflur, cefazedone, cefazolin, cefaradine, cefroxadine, ceftezole, cefteram, ceftibuten, ceftiofur, ceftiolene, ceftizoxime, cefaclor, cefprozil, cefuroxime, cefuzonam, cefmenoxime, cefodizime, cefotaxime, cefovecin, cefpimizole, cefpirome, cefquinome, ceftobiprole, cefpodoxime, ceftazidime, ceftaroline, cefclidine, cefepime, cefluprenam, cefoselis, cefozopran, cephalexin, cephaloridine, cefamandole, cefsulodin, cefonicid, cefoperazine, cefoperazone, cefprozil, ceftriaxone), penicillins and penicillin derivatives (e.g., penicillin G, penicillin V, procaine penicillin, benzathine penicillin, benzathine benzylpenicillin, ampicillin, epicillin, amoxicillin, benzylpenicillin, clometocillin, phenoxymethylpenicillin, oxacillin, methicillin, dicloxacillin, flucloxacillin, temocillin, azlocillin, carbenicillin, ricarcillin, mezlocillin, piperacillin, apalcillin, hetacillin, bacampicillin, sulbenicillin, mecicilam, pevmecillinam, ciclacillin, talapicillin, aspoxicillin, azidocillin, cloxacillin, nafcillin, pivampicillin, penamecillin, mecillinam, propicillin, pheneticillin, ticarcillin temocillin), carbapenems (e.g., thienamycin, tomopenem, lenapenem, tebipenem, razupenem, imipenem, meropenem, ertapenem, doripenem, panipenem (betamipron), biapenem), carbacephems (e.g., loracarbef), penems (e.g., faropenem), cephamycins (e.g., cefbuperazone, cefmetazole, cefminox, cefotetan, cefoxitin), monobactams (e.g., aztreonam, nocardicin A, tabtoxin, tigemonam), and oxacephems (e.g., flomoxef, latamoxef); lipopeptide antibiotics (e.g., amphomycin, aspartocin, brevistin, cerexin A, cerexin B, glumamycin, laspartomycin, tsushimycin, zaomycin, daptomycin); polymyxin antibiotics (e.g., polymyxin B, colistin (polymyxin E), polymyxin M); aminoglycosides (e.g., gentamicin, amikacin, tobramycin, debekacin, kanamycin, neomycin, netilmicin, paromomycin, sisomycin, spectinomycin, streptomycin); glycopeptides (e.g., vancomycin, teicoplanin, telavancin, ramoplanin, daptomycin, decaplanin, bleomycin); macrolides (e.g., azithromycin, clarithromycin, erythromycin, fidaxomicin, telithromycin, carbomycin A, josamycin, kitasamycin, midecamycin/midecamycinacetate, oleandomycin, solithromycin, spiramycin, troleandomycin, tylosin/tylocine, roxithromycin, dirithromycin, troleandomycin, spectinomycin, methymycin, neomethymycin, erythronolid, megalomycin, picromycin, narbomycin, oleandomycin, triacetyl-oleandomycin, laukamycin, kujimycin A, albocyclin, cineromycin B); ansamycins (e.g., streptovaricin, geldanamycin, herbimycin, rifamycin, rifampin, rifabutin, rifapentine, rifamixin); linezolid; pristinamycin; and sulfonamides (e.g., sulfanilamide, sulfacetarnide, sulfapyridine, sulfathiazole, sulfadiazine, sulfamerazine, sulfadimidine, sulfasomidine, sulfasalazine, mafenide, sulfamethoxazole, sulfamethoxypyridazine, sulfadimethoxine, sulfasymazine, sulfadoxine, sulfametopyrazine, sulfaguanidine, succinylsulfathiazole, phthalylsulfathiazole).

When the compositions of this invention comprise a combination of a compound of the formulae described herein and one or more additional therapeutic or prophylactic agents, both the compound and the additional agent should be present at dosage levels of between about 1% to about 100%, or between about 5% to about 95% of the dosage normally administered in a monotherapy regimen. The additional agents may be administered separately, as part of a multiple dose regimen, from the compounds of this invention. Alternatively, those agents may be part of a single dosage form, mixed together with the compounds of this invention in a single composition.

The term "pharmaceutically acceptable carrier or adjuvant" refers to a carrier or adjuvant that may be administered to a patient, together with a compound of this invention, and which does not destroy the pharmacological activity thereof and is nontoxic when administered in doses sufficient to deliver a therapeutic amount of the compound.

Pharmaceutically acceptable carriers, adjuvants and vehicles that may be used in the pharmaceutical compositions of this invention include, but are not limited to, ion exchangers, alumina, aluminum stearate, lecithin, self-emulsifying drug delivery systems (SEDDS) such as d-α-tocopherol polyethyleneglycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as α-, β-, and γ-cyclodextrin, may also be advantageously used to enhance delivery of compounds of the formulae described herein.

The pharmaceutical compositions of this invention may contain any conventional non-toxic pharmaceutically-ac ceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes parenteral, epidural, subcutaneous, intra-cutaneous, intra-venous, intra-muscular, intra-articular, intra-arterial, intra-synovial, intra-sternal, intra-thecal, intra-lesional and intra-cranial injection or infusion techniques.

An effective amount of a compound of the disclosure can be administered in either single or multiple doses by any of the accepted modes of administration. Regardless of the route of administration selected, the compounds of the present disclosure, and/or the pharmaceutical compositions of the present disclosure, are formulated into pharmaceutically-acceptable dosage forms. The compounds according to the disclosure can be formulated for administration in any convenient way for use in human or veterinary medicine, by analogy with other pharmaceuticals.

In one aspect, the disclosure provides pharmaceutical formulation comprising a therapeutically-effective amount of one or more of the compounds described above, formulated together with one or more pharmaceutically acceptable carriers (additives) and/or diluents. In one embodiment, one or more of the compounds described herein are formulated for parenteral administration for parenteral administration, one or more compounds disclosed herein can be formulated as aqueous or nonaqueous solutions, dispersions, suspensions or emulsions or sterile powders which can be reconstituted into sterile injectable solutions or dispersions just prior to use. Such formulations can comprise sugars, alcohols, antioxidants, buffers, bacteriostats, solutes which render the formulation isotonic with the blood of the intended recipient or suspending or thickening agents. These compositions can also contain adjuvants such as preservatives, wetting agents, emulsifying agents and dispersing agents. Prevention of the action of microorganisms upon the subject compounds can be ensured by the inclusion of various antibacterial and antifungal agents, for example, paraben, chlorobutanol, phenol sorbic acid, and the like. It can also be desirable to include isotonic agents, such as sugars, sodium chloride, and the like into the compositions. In addition, prolonged absorption of the injectable pharmaceutical form can be brought about by the inclusion of agents which delay absorption such as aluminum monostearate and gelatin. If desired the formulation can be diluted prior to use with, for example, an isotonic saline solution or a dextrose solution. In some examples, the compound is formulated as an aqueous solution and is administered intravenously.

Pharmaceutical compositions can be in the form of a solution or powder for injection. Such compositions may be formulated according to techniques known in the art using suitable dispersing or wetting agents (such as, for example, Tween 80) and suspending agents. The sterile injectable preparation may also be a sterile injectable solution or suspension in a non-toxic parenterally acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, or carboxymethyl cellulose or similar dispersing agents which are commonly used in the formulation of pharmaceutically acceptable dosage forms such as emulsions and or suspensions. Other commonly used surfactants such as Tweens, Spans, and/or other similar emulsifying agents or bioavailability enhancers which are commonly used in the manufacture of pharmaceutically acceptable solid, liquid, or other dosage forms may also be used for the purposes of formulation.

Pharmaceutical compositions can be orally administered in any orally acceptable dosage form including, but not limited to, capsules, tablets, emulsions and aqueous suspensions, dispersions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions and/or emulsions are administered orally, the active ingredient may be suspended or dissolved in an oily phase is combined with emulsifying and/or suspending agents. If desired, certain sweetening and/or flavoring and/or coloring agents may be added.

The pharmaceutical compositions of this invention may also be administered in the form of suppositories for rectal administration. These compositions can be prepared by mixing a compound of this invention with a suitable non-irritating excipient which is solid at room temperature but liquid at the rectal temperature and therefore will melt in the rectum to release the active components. Such materials include, but are not limited to, cocoa butter, beeswax and polyethylene glycols.

Alternatively or in addition, pharmaceutical compositions can be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

In some instances, one or more peptides disclosed herein can be conjugated, for example, to a carrier protein. Such conjugated compositions can be monovalent or multivalent. For example, conjugated compositions can include one peptide disclosed herein conjugated to a carrier protein. Alternatively, conjugated compositions can include two or more peptides disclosed herein conjugated to a carrier.

As used herein, when two entities are "conjugated" to one another they are linked by a direct or indirect covalent or non-covalent interaction. In certain embodiments, the association is covalent. In other embodiments, the association is non-covalent. Non-covalent interactions include hydrogen bonding, van der Waals interactions, hydrophobic interactions, magnetic interactions, electrostatic interactions, etc. An indirect covalent interaction is when two entities are covalently connected, optionally through a linker group.

Carrier proteins can include any protein that increases or enhances immunogenicity in a subject. Exemplary carrier proteins are described in the art (see, e.g., Fattom et al., Infect. Immun., 58:2309-2312, 1990; Devi et al., Proc. Natl. Acad. Sci. USA 88:7175-7179, 1991; $L_1$ et al., Infect. Immun. 57:3823-3827, 1989; Szu et al., Infect. Immun. 59:4555-4561, 1991; Szu et al., J. Exp. Med. 166:1510-1524, 1987; and Szu et al., Infect. Immun. 62:4440-4444, 1994). Polymeric carriers can be a natural or a synthetic material containing one or more primary and/or secondary amino groups, azido groups, or carboxyl groups. Carriers can be water soluble.

Methods of Treatment

The disclosure includes methods of using the peptides herein for the prophylaxis and/or treatment of infection. The terms "treat", "treating" or "treatment" as used herein, refers to partially or completely alleviating, inhibiting, ameliorating, and/or relieving the disease or condition from which the subject is suffering. This means any manner in which one or more of the symptoms of a disease or disorder (e.g., cancer) are ameliorated or otherwise beneficially altered. As used herein, amelioration of the symptoms of a particular disorder (e.g., infection) refers to any lessening, whether permanent or temporary, lasting or transient that can be attributed to or associated with treatment by the compositions and methods of the present invention. In some embodiments, treatment can promote or result in, for example, a decrease in the number of microbial cells or organisms (e.g., in a subject) relative to the number of microbial cells or organisms prior to treatment; a decrease in the viability (e.g., the average/mean viability) of microbial cells or organisms (e.g., in a subject) relative to the viability (e.g., the average/mean viability) of microbial cells or organisms (e.g., in the subject) prior to treatment; and/or reductions in one or more symptoms associated with one or more infections in a subject relative to the subject's symptoms prior to treatment.

Examples of bacteria internally cross-linked AMPs are active against include, without limitation, *Staphylococci* (e.g., *S. aureus, S. intermedius, S. epidermidis*, and other coagulase negative *Staphylococci*), *Neisseriae* (e.g., *N. gonorrheae* and *N. meningitidis*), *Streptococci* (e.g., Group A *Streptococcus* (e.g., *S. pyogenes*), Group B *Streptococcus* (e.g., *S. agalactiae*), Group C *Streptococcus*, Group G *Streptococcus, S. pneumoniae*, and *viridans Streptococci*), *Chlamydia trachomatis, Treponemae* (e.g., *T. pallidum, T. pertenue*, and *T. cerateum*), *Haemophilus* bacteria (e.g., *H. ducreyi, H. influenzae*, and *H. aegyptius*), *Bordetellae* (e.g., *B. pertussis, B. parapertussis*, and *B. bronchiseptica*), *Gardnerella vaginalis, Bacillus* (e.g., *B. anthracis* and *B. cereus*), *Mycobacteria* (e.g., *M. tuberculosis* and *M. leprae*), *Listeria monocytogenes, Borrelia burgdorferi, Actinobacillus pleuropneumoniae, Helicobacter pylori, Clostridium* (e.g. *C. perfringens, C. septicum, C. novyi*, and *C. tetani*), *Escherichia coli, Porphyromonas gingivalis, Vibrio cholerae, Salmonella* bacteria (e.g., *S. enteriditis, S. typhimurium*, and *S. typhi*), *Shigella* bacteria, *Francisella* bacteria, *Yersinia* bacteria (e.g. *Y. pestis* and *Y. enterocolitica*), *Burkholderia* bacteria, *Pseudomonas* bacteria, and *Brucella* bacteria. Mycoplasmal organisms AMPs are active against include, e.g., *M. pneumoniae, M. fermentans, M. hominis*, and *M. penetrans*.

Examples of fungal (including yeast) organisms internally cross-linked AMPs are active against include, but are not limited to, *Candida albicans*, other *Candida* species, *Cryptococcus neoformans, Histoplasma capsulatum*, and *Pneumocystis carinii*.

Examples of protozoan parasites internally cross-linked AMPs are active against include, without limitation, *Trichomonas vaginalis, Plasmodium falciparum, P. vivax, P. ovale, P. malariae, Entamoeba histolytica, Toxoplasma brucei, Toxoplasma gondii*, and *Leishmania major*.

Examples of viruses internally cross-linked AMPs may be employed against include, but are not limited to cells infected with, human immunodeficiency virus (HIV) 1 and 2, human lymphotropic virus (HTLV), measles virus, rabies virus, hepatitis virus A, B, and C, rotaviruses, rhinoviruses, influenza virus, parainfluenza virus, respiratory syncytial virus, adenoviruses, parvoviruses (e.g., parvovirus B 19), roseola virus, enteroviruses, papilloma viruses, retroviruses, herpesviruses (e.g., herpes simplex virus, varicella zoster virus, Epstein Barr virus (EBV), human cytomegalovirus (CMV), human herpesvirus 6, 7 and 8), poxviruses (e.g., variola major and variola minor, vaccinia, and monkeypox virus), feline leukemia virus, feline immunodeficiency virus, and simian immunodeficiency virus. While the structurally stabilized I-TAMPs translocate into microbial cell and exert their biological activities within the microbial cells, it is envisioned that structurally stabilized AMPs having appropriate intra-mammalian cell activities (e.g., anti-intracellular virus or other intra-mammalian cell anti-microbial activity) with the ability to translocate into relevant mammalian cells, without causing significant lysis of the mammalian cells, can be developed.

Disorders that can be treated by the compositions, formulations, and/or methods described herein include, but are not limited to, infectious diseases. Infectious diseases can be caused by pathogens, such as bacteria, viruses, fungi or parasites. In some embodiments, an infectious disease can be passed from person to person. In some embodiments, an infectious disease can be transmitted by bites from insects or animals. In some embodiments, an infectious disease can be acquired by ingesting contaminated food or water or being exposed to organisms in the environment. Some infectious diseases can be prevented by vaccines.

In specific embodiments, infectious diseases that can be treated by the compositions, formulations, and/or methods described herein include, but are not limited to, *Acinetobacter* infections, Actinomycosis, African sleeping sickness (African trypanosomiasis), AIDS (Acquired immunodeficiency syndrome), Amebiasis, Anaplasmosis, Angiostrongyliasis, Anisakiasis, Anthrax, *Arcanobacterium haemolyticum* infection, Argentine hemorrhagic fever, Ascariasis, Aspergillosis, Astrovirus infection, Babesiosis, *Bacillus cereus* infection, Bacterial pneumonia, Bacterial vaginosis, *Bacteroides* infection, Balantidiasis, Bartonellosis, *Baylisascaris* infection, BK virus infection, Black piedra, Blastocystosis, Blastomycosis, Bolivian hemorrhagic fever, Botulism (and Infant botulism), Brazilian hemorrhagic fever, Brucellosis, Bubonic plague, *Burkholderia* infection, Buruli ulcer, Calicivirus infection (Norovirus and Sapovirus), Campylobacteriosis, Candidiasis (Moniliasis; Thrush), Capillariasis, Carrion's disease, Cat-scratch disease, Cellulitis, Chagas Disease (American trypanosomiasis), Chancroid, Chickenpox, Chikungunya, *Chlamydia, Chlamydophila pneumoniae* infection (Taiwan acute respiratory agent or TWAR), Cholera, Chromoblastomycosis, Chytridiomycosis, Clonorchiasis, *Clostridium difficile* colitis, Coccidioidomycosis, Colorado tick fever (CTF), Common cold (Acute viral rhinopharyngitis; Acute coryza), Creutzfeldt-Jakob disease (CJD), Crimean-Congo hemorrhagic fever (CCHF), Cryptococcosis, Cryptosporidiosis, Cutaneous larva migrans (CLM), Cyclosporiasis, Cysticercosis, Cytomegalovirus infection, Dengue fever, Desmodesmus infection, Dientamoebiasis, Diphtheria, Diphyllobothriasis, Dracunculiasis, Ebola hemorrhagic fever, Echinococcosis, Ehrlichiosis, Enterobiasis (Pinworm infection), *Enterococcus* infection, Enterovirus infection, Epidemic typhus, Erythema infectiosum (Fifth disease), *Exanthem subitum* (Sixth disease), Fasciolasis, Fasciolopsiasis, Fatal familial insomnia (FFI), Filariasis, Food poisoning by *Clostridium perfringens*, Free-living amebic infection, *Fusobacterium* infection, Gas gangrene (Clostridial myonecrosis), Geotrichosis, Gerstmann-Straussler-Scheinker syndrome (GSS), Giardiasis, Glanders, Gnathostomiasis, Gonorrhea, Granuloma inguinale (Donovanosis), Group A streptococcal infection, Group B streptococcal infection, *Haemophilus influenzae* infection, Hand, foot and mouth disease (HFMD), Hantavirus Pulmonary Syndrome (HPS), Heartland virus disease, *Helicobacter pylori* infection, Hemolytic-uremic syndrome (HUS), Hemorrhagic fever with renal syndrome (HFRS), Hepatitis A, Hepatitis B, Hepatitis C, Hepatitis D, Hepatitis E, Herpes simplex, Histoplasmosis, Hookworm infection, Human bocavirus infection, Human ewingii ehrlichiosis, Human granulocytic anaplasmosis (HGA), Human metapneumovirus infection, Human monocytic ehrlichiosis, Human papillomavirus (HPV) infection, Human parainfluenza virus infection, Hymenolepiasis, Epstein-Barr Virus Infectious Mononucleosis (Mono), Influenza (flu), Isosporiasis, Kawasaki disease, Keratitis, Kingella kingae infection, Kuru, Lassa fever, Legionellosis (Legionnaires' disease), Legionellosis (Pontiac fever), Leishmaniasis, Leprosy, Leptospirosis, Listeriosis, Lyme disease (Lyme borreliosis), Lymphatic filariasis (Elephantiasis), Lymphocytic choriomeningitis, Malaria, Marburg hemorrhagic fever (MHF), Measles, Middle East respiratory syndrome (MERS), Melioidosis (Whitmore's disease), Meningitis, Meningococcal disease, Metagonimiasis, Microsporidiosis, Molluscum contagiosum (MC), Monkeypox, Mumps, Murine typhus (Endemic typhus), *Mycoplasma* pneumonia, Mycetoma (disambiguation), Myiasis, Neonatal conjunctivitis (Ophthalmia neonatorum), Variant Creutzfeldt-Jakob disease (vCJD, nvCJD), Nocardiosis, Onchocerciasis (River blindness), Opisthorchiasis, Paracoccidioidomycosis (South American blastomycosis), Paragonimiasis, Pasteurellosis, Pediculosis capitis (Head lice), Pediculosis corporis (Body lice), Pediculosis pubis (Pubic lice, Crab lice), Pelvic inflammatory disease (PID), Pertussis (Whooping cough), Plague, Pneumococcal infection, *Pneumocystis* pneumonia (PCP), Pneumonia, Poliomyelitis, *Prevotella* infection, Primary amoebic meningoencephalitis (PAM), Progressive multifocal leukoencephalopathy, Psittacosis, Q fever, Rabies, Relapsing fever, Respiratory syncytial virus infection, Rhinosporidiosis, Rhinovirus infection, Rickettsial infection, Rickettsialpox, Rift Valley fever (RVF), Rocky Mountain spotted fever (RMSF), Rotavirus infection, Rubella, *Salmonellosis*, SARS (Severe Acute Respiratory Syndrome), Scabies, Schistosomiasis, Sepsis, Shigellosis (Bacillary dysentery), Shingles (Herpes zoster), Smallpox (Variola), Sporotrichosis, Staphylococcal food poisoning, Staphylococcal infection, Strongyloidiasis, Subacute sclerosing panencephalitis, Syphilis, Taeniasis, Tetanus (Lockjaw), Tinea barbae (Barber's itch), Tinea capitis (Ringworm of the Scalp), Tinea corporis (Ringworm of the Body), Tinea cruris (Jock itch), Tinea manum (Ringworm of the Hand), Tinea nigra, Tinea pedis (Athlete's foot), Tinea unguium (Onychomycosis), Tinea versicolor (*Pityriasis versicolor*), Toxocariasis (Ocular Larva Migrans (OLM)), Toxocariasis (Visceral Larva Migrans (VLM)), Trachoma, Toxoplasmosis, Trichinosis, Trichomoniasis, Trichuriasis (Whipworm infection), Tuberculosis, Tularemia, Typhoid fever, Typhus fever, *Ureaplasma urealyticum* infection, Valley fever, Venezuelan equine encephalitis, Venezuelan hemorrhagic fever, *Vibrio vulnificus* infection, *Vibrio parahaemolyticus* enteritis, Viral pneumonia, West Nile Fever, White piedra (Tinea blanca), *Yersinia pseudotuberculosis* infection, Yersiniosis, Yellow fever, and Zygomycosis.

The compositions, formulations, and/or methods described herein can be used to treat a pathogen. In some embodiments, the pathogen can be a virus, bacterium, prion, a fungus, or a parasite. In specific embodiments, the pathogen described herein include, but are not limited to, *Acinetobacter baumannii*, *Actinomyces israelii*, *Actinomyces gerencseriae* and *Propionibacterium* propionicus, *Trypanosoma brucei*, HIV (Human immunodeficiency virus), *Entamoeba histolytica*, *Anaplasma* species, *Angiostrongylus*, *Anisakis*, *Bacillus anthracis*, *Arcanobacterium haemolyticum*, *Junin virus*, *Ascaris lumbricoides*, *Aspergillus* species, Astroviridae family, *Babesia* species, *Bacillus cereus*, bacterial vaginosis microbiota, *Bacteroides* species, *Balantidium coli*, *Bartonella*, *Baylisascaris* species, BK virus, Piedraia hortae, *Blastocystis* species, *Blastomyces dermatitidis*, *Machupo virus*, *Clostridium botulinum*, Sabia, *Brucella* species, Enterobacteriaceae, *Burkholderia cepacia* and other *Burkholderia* species, *Mycobacterium ulcerans*, *Caliciviridae* family, *Campylobacter* species, *Candida albicans* and other *Candida* species, *Capillaria philippinensis*, *Capillaria* hepatica, *Capillaria aerophila*, *Bartonella bacilliformis*, *Bartonella henselae*, Group A *Streptococcus* and *Staphylococcus*, *Trypanosoma cruzi*, *Haemophilus ducreyi*, Varicella zoster virus (VZV), Alphavirus, *Chlamydia trachomatis*, *Chlamydophila pneumoniae*, *Vibrio cholera*, *Fonsecaea pedrosoi*, *Batrachochytrium dendrabatidis*, *Clonorchis sinensis*, *Clostridium difficile*, *Coccidioides immitis* and *Coccidioides posadasii*, Colorado tick fever virus (CTFV), rhinoviruses and coronaviruses, PRNP, Crimean-Congo hemorrhagic fever virus, *Cryptococcus neoformans*, *Cryptosporidium species*, *Ancylostoma braziliense*; multiple other parasites, *Cyclospora cayetanensis*, *Taenia solium*, Cytomegalovirus, Dengue viruses (DEN-1, DEN-2, DEN-3 and DEN-4)—Flaviviruses, Green algae Desmodesmus armatus, *Dientamoeba fragilis*, *Corynebacterium diphtheria*, *Diphyllobothrium*, *Dracunculus medinensis*, Ebolavirus (EBOV), *Echinococcus* species, *Ehrlichia* species, *Enterobius vermicularis*, *Enterococcus* species, *Enterovirus* species, *Rickettsia prowazekii*, Parvovirus B 19, Human herpesvirus 6 (HHV-6) and Human herpesvirus 7 (HHV-7), *Fasciola hepatica* and *Fasciola gigantica*, *Fasciolopsis buski*, PRNP, Filarioidea superfamily, *Clostridium perfringens*, *Fusobacterium species*, *Clostridium perfringens*, other *Clostridium* species, *Geotrichum candidum*, *Giardia lamblia*, *Burkholderia mallei*, *Gnathostoma spinigerum* and *Gnathostoma hispidum*, *Neisseria gonorrhoeae*, *Klebsiella granulomatis*, *Streptococcus pyogenes*, *Streptococcus agalactiae*, *Haemophilus* influenza, Enteroviruses, mainly Coxsackie A virus and *Enterovirus* 71 (EV71), Sin Nombre virus, Heartland virus, *Helicobacter pylori*, *Escherichia coli* O157:H7, O111 and O104:H4, Bunyaviridae family, Hepatitis A virus, Hepatitis B virus, Hepatitis C virus, Hepatitis D Virus, Hepatitis E virus, Herpes simplex virus 1 and 2 (HSV-1 and HSV-2), *Histoplasma capsulatum*, *Ancylostoma duodenale* and *Necator americanus*, Human bocavirus (HBoV), *Ehrlichia ewingii*, *Anaplasma phagocytophilum*, Human metapneumovirus (hMPV), *Ehrlichia chaffeensis*, Human papillomavirus (HPV), Human parainfluenza viruses (HPIV), *Hymenolepis nana* and *Hymenolepis diminuta*, Epstein-Barr Virus (EBV), Orthomyxoviridae family, *Isospora belli*, Kingella kingae, Lassa virus, *Legionella pneumophila*, *Leishmania* species, *Mycobacterium leprae*, *Mycobacterium lepromatosis*, *Leptospira* species, *Listeria monocytogenes*, *Borrelia burgdorferi*, *Borrelia garinii*, *Borrelia afzelii*, *Wuchereria bancrofti*, *Brugia malayi*, Lymphocytic choriomeningitis virus (LCMV), *Plasmodium* species, Marburg virus, Measles virus, Middle East respiratory syndrome coronavirus, *Burkholderia pseudomallei*, *Neisseria meningitides*, *Metagonimus* yokagawai, Microsporidia phylum, Molluscum contagiosum virus (MCV), Monkeypox virus, Mumps virus, *Rickettsia typhi*, *Mycoplasma pneumoniae*, Actinomycetoma, Eumycetoma, parasitic dipterous fly larvae, *Chlamydia trachomatis*, *Neisseria gonorrhoeae*, *Nocardia asteroids*, *Nocardia species*, *Onchocerca volvulus*, *Opisthorchis viverrini* and *Opisthorchis felineus*, *Paracoccidioides brasiliensis*, *Pediculus humanus* capitis, *Phthirus pubis*, *Bordetella pertussis*, *Yersinia pestis*, *Streptococcus pneumoniae*, *Pneumocystis jirovecii*, Poliovirus, *Prevotella* species, *Naegleria fowleri*, JC virus, *Chlamydophila psittaci*, *Coxiella burnetii*, Rabies virus, *Borrelia hermsii*, *Borrelia recurrentis*, *Borrelia* species, Respiratory syncytial virus (RSV), *Rhinosporidium seeberi*, Rhinovirus, *Rickettsia* species, *Rickettsia akari*, Rift Valley fever virus, *Rickettsia rickettsia*, Rotavirus, Rubella virus, *Salmonella* species, SARS coronavirus, *Sarcoptes scabiei*, *Schistosoma* species, *Shigella* species, Varicella zoster virus (VZV), Variola major, Variola minor, *Sporothrix schenckii*, *Staphylococcus* species, *Strongyloides stercoralis*, *Measles* virus, *Treponema pallidum*, *Taenia* species, *Clostridium tetani*, *Trichophyton* species, *Trichophyton tonsurans*, *Epidermophyton floccosum*, *Trichophyton rubrum*, *Trichophyton mentagrophytes*, *Trichophyton rubrum*, *Hortaea werneckii*, *Trichophyton* species, *Trichophyton* species, *Malassezia* species, *Toxocara canis*, *Toxocara cati*, *Chlamydia trachomatis*, *Toxoplasma gondii*, *Trichinella spiralis*, *Trichomonas vaginalis*, *Trichuris trichiura*, *Mycobacterium tuberculosis*, *Francisella tularensis*, *Salmonella enterica* subsp. *enterica*, serovar typhi, *Rickettsia*, *Ureaplasma urealyticum*, *Coccidioides immitis*, *Coccidioides posadasii*, Venezuelan equine encephalitis virus, Guanarito virus, *Vibrio vulnificus*, *Vibrio parahaemolyticus*, multiple viruses, West Nile virus, *Trichosporon beigelii*, *Yersinia pseudotuberculosis, Yersinia enterocolitica*, Yellow fever virus, Mucorales order (Mucormycosis), and Entomophthorales order (Entomophthoramycosis).

All the methods of treatment and prophylaxis described herein may be applied to at least any or all the above-listed microbial organisms.

In some embodiments, the compounds of the invention can be toxic to one microbe. In some embodiments, the compounds of the invention can be toxic to two microbes. In some embodiments, the compounds of the invention can be toxic to three microbes. In some embodiments, the compounds of the invention can be toxic to four microbes. In some embodiments, the compounds of the invention can be toxic to five microbes.

In some embodiments, the compounds of the invention can be used to treat a microbe without damaging the host subject. In some embodiments, the compounds of the invention can be used to treat two microbes without damaging the host subject. In some embodiments, the compounds of the invention can be used to treat three microbes without damaging the host subject. In some embodiments, the compounds of the invention can be used to treat four microbes without damaging the host subject. In some embodiments, the compounds of the invention can be used to treat five microbes without damaging the host subject.

In general, methods include selecting a subject and administering to the subject an effective amount of one or more of the peptides herein, e.g., in or as a pharmaceutical composition, and optionally repeating administration as required for the prophylaxis or treatment of a microbial infection and can be administered, e.g., orally, intravenously or topically.

Specific dosage and treatment regimens for any particular patient will depend upon a variety of factors, including the activity of the specific compound employed, the age, body weight, general health status, sex, diet, time of administration, rate of excretion, drug combination, the severity and course of the disease, condition or symptoms, the patient's disposition to the disease, condition or symptoms, and the judgment of the treating physician.

An effective amount can be administered in one or more administrations, applications or dosages. A therapeutically effective amount of a therapeutic compound (i.e., an effective dosage) depends on the therapeutic compounds selected. The compositions can be administered one from one or more times per day to one or more times per week; including once every other day. The skilled artisan will appreciate that certain factors may influence the dosage and timing required to effectively treat a subject, including but not limited to the severity of the disease or disorder, previous treatments, the general health and/or age of the subject, and other diseases present.

Moreover, treatment of a subject with a therapeutically effective amount of the therapeutic compounds described herein can include a single treatment or a series of treatments. For example, effective amounts can be administered at least once. Upon improvement of a patient's condition, a maintenance dose of a compound, composition or combination of this invention may be administered, if necessary. Subsequently, the dosage or frequency of administration, or both, may be reduced, as a function of the symptoms, to a level at which the improved condition is retained. Patients may, however, require intermittent treatment on a long-term basis upon any recurrence of disease symptoms.

In some instances, the peptides herein can further be co-administered with one or more additional therapeutic agents in amounts effective for achieving a modulation of disease or disease symptoms. Such additional therapeutic agents may include conventional antimicrobial agents (e.g., antibiotics) known in the art. When co-administered, stapled AMPs of the invention operate in conjunction with conventional antimicrobial agents to produce mechanistically additive or synergistic antimicrobial effects. Without being limited by any particular mechanism of action, certain internally cross-linked (e.g., stapled) AMPs having the ability to produce "pores" in the membranes of certain microbial organisms (including, e.g., Gram-negative bacteria) can act to facilitate and/or enhance the passage of appropriate conventional antimicrobial agents to the interiors of relevant microbial cells. For the same purpose, the internally cross-linked AMPs can be conjugated (covalently or non-covalently) to appropriate antimicrobial agents, the resulting conjugates being administered to appropriate subjects.

The ability of select internally cross-linked and intracellular targeting AMPs to also produce transient "pores" in the membranes of microbial organisms provides the basis for another utility for them. Thus, e.g., relevant microbial organisms (e.g., any of those disclosed herein) can be contacted either in a subject or in vitro to an internally cross-linked AMP with the ability to produce "pores" or even lysis of the microbial organism. As result of this activity, nucleic acids (e.g., DNA and/or RNA) are released from microbial organisms into their surroundings. This phenomenon can be used as a basis for accurate, rapid, and inexpensive identification of the microbial organism. Where the contacting occurs in a subject, any of a variety of bodily fluids (e.g., blood, lymph, urine, feces, mucus, or tears) or body lavages can be tested. Where the contacting occurs in vitro, culture medium can be tested.

Application to Medical or Hygienic Devices

The antimicrobial peptides of the invention can be applied to, or incorporated into, various medical and/or hygienic devices (e.g., as a coating, or impregnated within a biodegradable device for exposure or release as the device degrades or dissolves after the device is inserted into a bodily canal of a vertebrate subject, inserted into a bodily cavity of a vertebrate subject, or applied to a tissue or organ of a vertebrate animal) to prevent or inhibit microbial (e.g., bacterial or biofilm) growth. Medical or hygienic devices suitable for use with the stapled peptides disclosed herein include, but are not limited to, devices that are inserted into a bodily canal of a vertebrate subject, inserted into a bodily cavity of a vertebrate subject, or applied to a tissue or organ of a vertebrate animal for the purpose of: (a) wound protection; (b) preventing or reducing unwanted, or overcoming restricted, release from the body of the vertebrate subject of a bodily fluid, bodily secretion, or excreta (e.g., blood, menses, urine, lymphatic fluid, cerebrospinal fluid, semen, saliva, vaginal secretions, mucus, or feces); (c) delivering a drug or some other therapeutic or prophylactic agent to a subject; (d) replacing absent or supplementing defective organ functions; or (e) maintaining the patency of a bodily canal (e.g., a blood vessel). Specific examples of medical or hygienic devices include, without limitation: rectal devices such as suppositories, enemas, and catheters; nasal, tracheal, or esophageal delivery devices; vaginal devices such as vaginal tampons and contraceptive devices (e.g., diaphragms or intrauterine devices (IUDs)); venous, arterial, intracranial and other needles, catheters and stents; renal dialysis accesses; surgical bandages, sutures, or dressings; ostomy devices; natural and synthetic implantable tissue matrices (see, for example, U.S. Pat. No. 5,885,829, incorporated herein by reference in its entirety); pace makers and pace maker wires and leads; synthetic and natural prostheses such as hip and knee prostheses and heart valves; osmotic pumps (e.g., mini osmotic pumps) that are implanted in body cavity (e.g., the peritoneal cavity) and provide slow delivery of a drug or some other therapeutic or prophylactic agent.

Further Applications

Examples of suitable animals for treatment are generally known in the art and include (but are not limited to), e.g., poultry and other birds (including chickens, turkeys, ducks, ostrich, emu, quail), ruminants (including goats, sheep, and cattle), fish, pigs, rabbits, mice, rats, horses, donkeys, monkeys, apes, felines (including cats), hamsters, ferrets, guinea pigs, and canines (including dogs). Examples of suitable plants for treatment are generally known in the art and include (but are not limited to), e.g., almond, apple, amaranth, artichoke, asparagus, avocado, banana and plantain, barley, beet, berries (including blueberry, blackberry, strawberry, and raspberry), breadfruit and jackfruit, brussels sprout, cabbage, carrot, cassava, cauliflower and broccoli, celery, chayote, cherry, coconut, collard and kale, corn (maize), cucumber and zucchini, dandelion, eggplant, endive and chicory, garlic, kohlrabi, grape, legume, lettuce, melons (including honeydew, cantaloupe, and watermelon), mustard, oat, oca, olive, okra, onion, orange and grapefruit, oyster plant, pear, peach, pemmican, pepper, potato and other tubers, *quinoa*, radish, rice, rhubarb, rye, sago, sorghum, soybean, spinach, pumpkin and other squashes, sunchoke, taro, teff, tomato, turnip, ulluco, vanilla, watercress, wheat, yam, and yautia. Examples of suitable foods for treatment are generally known in the art and include (but are not limited to), e.g., algae, mushrooms, and products derived from animals (e.g., beef, butter, eggs, (ice) cream, gravy, milk, pork, veal, yogurt) and/or plants (e.g., beer, bread, cereal, chocolate, coffee, ketchup, mustard sauce, oatmeal, juice, monosodium glutamate, salad, soda, soft drinks, soymilk, soy sauce, tea, tofu, fries, vinegar, wine) as described above.

The peptides herein can also be applied in the personal care and/or consumer products context (e.g., to health or beauty products in sterilization processes) to reduce or eliminate the risk of microbial (e.g., bacterial) contamination. Examples of suitable products for treatment are generally known in the art and include (but are not limited to), e.g., brushes, conditioners, clips, clippers, curling irons, shampoos, soaps, lotions, topical acne ointments, oils, colorants, dyes, perfumes, pins, fragrances, razors, shaving devices, deodorants, cosmetics, kitchen and/or dining devices (e.g., cutting boards, racks, containers, pots, pans, utensils), and cleaning products (e.g., brooms, mops, dustpans, sweepers) and cleaning solutions.

EXAMPLES

Example 1: Synthesis of Stapled I-TAMP Analogues

We synthesized a complete i, i+4, and i, i+7 staple scanning panel of stapled buforin II peptides to identify which staple insertion position(s) yield I-TAMP analogues with optimal biological and pharmacologic properties (FIG. 1). In some compositions, replacement of the central proline residue was avoided given the potential role of prolines as breakpoints in secondary structure. Also, in some panels, the phenylalanine adjacent to the proline was replaced with tryptophan for facile determination of peptide concentration by UV spectroscopy. The production of these exemplary panels allowed us to interrogate the effects of structural stabilization of various segments of the parent I-TAMP on its antimicrobial and hemolytic activity.

Example 2: Alpha-Helical Characterization of Stapled I-TAMP Analogues

To determine the α-helical content for each peptide within our panel of stapled I-TAMP analogues, we studied the peptides dissolved in 10 mM phosphate buffer (pH 7.4) using CD spectroscopy in the presence and absence of trifluoroethanol (TFE; 50% v/v), an α-helix promoting solvent. In the absence of TFE, the i, i+4 stapled analogues displayed modestly improved α-helical structure compared to the unstapled parent I-TAMP, buforin II (F10W), which was otherwise completely disordered (FIG. 2 Panel A). Upon the addition of TFE, the α-helical content increased for some of the stapled analogues and the parent I-TAMP (F10W), but not as dramatically as we previously observed for α-helical AMPs (FIG. 2 Panel B), consistent with the incorporation of a helix-breaking proline within the buforin II sequence. The i, i+7 stapled analogues displayed higher levels of α-helicity when compared to their i, i+4 counterparts, both in the presence and absence of TFE (FIG. 3).

Example 3: Hemolytic Activity of Stapled I-TAMP Peptides

One of the key obstacles that have long impeded the use of AMPs in systemic infections such as sepsis is their tendency to lyse human cells, such as red blood cells (RBCs). Thus, it is critical to minimize hemolytic activity as much as possible to achieve a therapeutic window. When we tested stapled analogues of the I-TAMP buforin II in a 1% RBC suspension in phosphate buffer, most i, i+4 analogues displayed low hemolytic activity, although in some cases there was a 5-fold increase in hemolysis (TABLE 1). Generally, the i, i+7 analogues had higher hemolytic activity, likely due to the greater hydrophobicity of the longer hydrocarbon staple (Table 1). Of note, in those circumstances where hydrocarbon staples increase hemolytic activity due to increasing hydrophobicity, the alkene moiety can be modified, e.g., by dihydroxylation, to install hydrophilic residues and potentially mitigate hemolysis.

Balancing antimicrobial potency and suppression of hemolytic activity, we identified BFStap(i+4)7 and BFStap (i+4)11 as specific exemplary candidates for further development, as they displayed the greatest increase in antimicrobial activity while maintaining low hemolytic activity.

Figure 8:
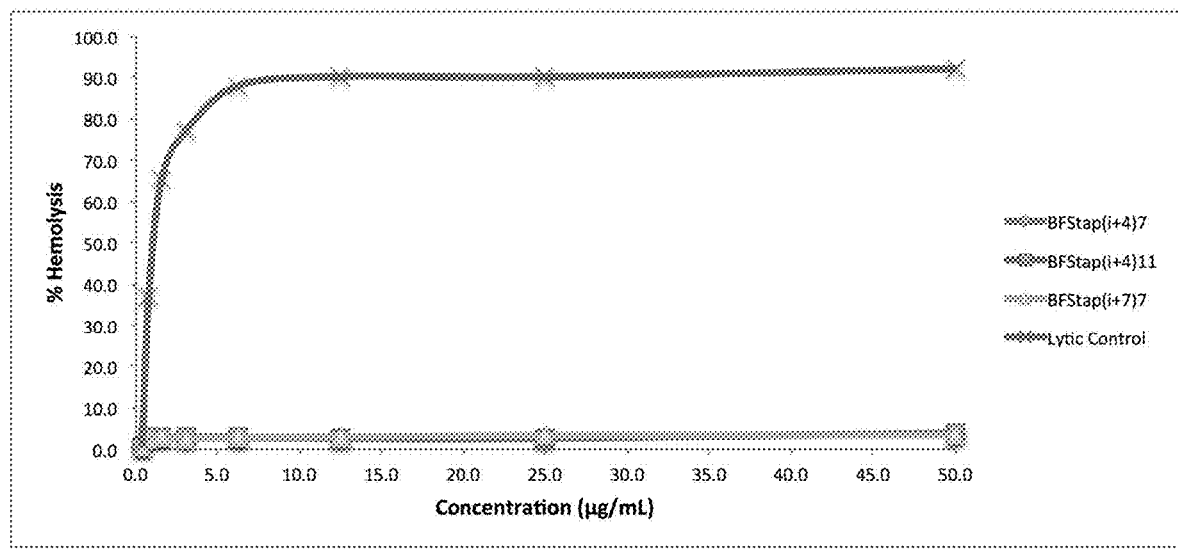
FIG. 8 is a graph showing the hemolysis of stapled buforin II analogues. Stapled buforin II analogs were incubated with 1% v/v human red blood cells (RBCs) in phosphate buffer for 1 hour at 37° C. and then the supernatant was collected and hemoglobin release was measured using UV absorbance at 570 nm. As opposed to a stapled lytic control peptide, the buforin II analogs displayed hemolysis levels below 5% at all the concentrations tested up to 50 µg/mL.

FIG. 8 is a graph showing the hemolysis of stapled buforin II analogues. Stapled buforin II analogs were incubated with 1% v/v human red blood cells (RBCs) in phosphate buffer for 1 hour at 37° C. and then the supernatant was collected and hemoglobin release was measured using UV absorbance at 570 nm. As opposed to a stapled lytic control peptide, the buforin II analogs displayed hemolysis levels below 5% at all the concentrations tested up to 50 g/mL.

TABLE 1

Minimum inhibitory concentrations (MICs) of buforin II and stapled derivatives against *E. coli*, and the hemolytic activity of said peptides at 50 µg/ml.

| Peptide | Antimicrobial Activity NIC (µg/ml) *E. coli* | % Hemolysis at 50 µg/ml |
|---|---|---|
| Buforin II | >800 | 2.1 |
| Buforin II(F10W) | >800 | 2.7 |
| BFStap(i + 4)1 | 50.0 | 2.2 |
| BFStap(i + 4)2 | 5.2 | 12.6 |
| BFStap(i + 4)3 | 25.0 | 2.9 |
| BFStap(i + 4)4 | 29.2 | 2.9 |
| BFStap(i + 4)5 | 66.7 | 3.0 |
| BFStap(i + 4)6 | 8.3 | 10.0 |
| BFStap(i + 4)7 | 6.3 | 3.4 |
| BFStap(i + 4)8 | 29.2 | 2.8 |
| BFStap(i + 4)9 | 50.0 | 2.5 |
| BFStap(i + 4)10 | 100 | 2.4 |
| BFStap(i + 4)11 | 6.3 | 3.1 |
| BFStap(i + 4)12 | >100 | 2.4 |
| BFStap(i + 4)13 | >100 | 2.4 |
| BFStap(i + 7)1 | 10.4 | 16.6 |
| BFStap(i + 7)2 | 33.3 | 3.1 |
| BFStap(i + 7)3 | 29.2 | 6.1 |
| BFStap(i + 7)4 | 3.1 | 57.0 |
| BFStap(i + 7)5 | 52.1 | 6.8 |
| BFStap(i + 7)6 | 6.3 | 9.5 |
| BFStap(i + 7)7 | 22.9 | 3.0 |
| BFStap(i + 7)8 | 12.5 | 3.9 |
| BFStap(i + 7)9 | 41.7 | 4.3 |
| BFStap(i + 7)10 | >100 | 2.3 |

Example 4: Antimicrobial Activity of Stapled I-TAMP Peptides

To determine the antimicrobial activity of the stapled buforin II analogues compared to the unstapled sequence, we determined the MIC against a common Gram-negative pathogen, *Escherichia coli* (*E. coli*). Most studies utilize radial diffusion assays (RDAs) to study buforin II activity, but since the microbroth dilution assay is the standard technique used in the antibiotic field, we adopted the more broadly applied technique. Compared to the activity of the unstapled buforin II (F10W) and buforin II, all stapled analogues displayed higher levels of activity, even beyond what would have been anticipated due to modest structural stabilization (TABLES 1 AND 2). Strikingly, in certain cases, such as for BFStap(i+4)7 and BFStap(i+7)4, the observed increase in activity compared to unmodified buforin II was over 200-fold. Of note, it was especially unexpected that stapling the N-terminal region yielded superior compounds than installing staples in the C-terminal region, which was the previously C-terminal alpha-helical region of buforin II. These results reaffirm the importance of comprehensive staple scanning to discover optimal constructs, as the staple insertion sites were not apparent or obvious based on previous structural and biological data.

TABLE 2

Minimum inhibitory concentrations (MICs) of buforin II and stapled derivatives against Gram-positive and Gram-negative bacterial pathogens.

| Peptide | Antimicrobial Activity MIC (µg/ml) | | | | |
|---|---|---|---|---|---|
| | *E. coli* | *B. cereus* | *P. aeruginosa* | *S. Aureus* | MRSA |
| Buforin II | >800 | >800 | >800 | >800 | >800 |
| BFStap(i + 4)7 | 6.25 | 12.5 | 12.5 | 12.5 | 25 |
| BFStap(i + 4)11 | 6.25 | 25 | 12.5 | 50 | >50 |
| BFStap(i + 7)6 | 6.25 | 12.5 | 12.5 | 25 | >50 |

Methods Used in Examples

Solid Phase Peptide Synthesis

Fmoc-based solid-phase peptide synthesis was used to synthesize the antimicrobial peptides and their stapled derivatives. To achieve the various staple lengths, α-methyl, α-alkenyl amino acids were used flanking two, three or six residues. As examples, an $R_5$ or $R_3$ residue can be incorporated at position i and $S_5$ at position i+3, while two $S_5$ residues can be used at the i and i+4 locations, and an $R_8$ at position i and $S_5$ at i+7 (or $S_5$ at position i and $R_5$ at i+7) [20]. For the stapling reaction, Grubbs $1^{st}$ generation ruthenium catalyst dissolved in dichloroethane was added to the peptides on resin. To ensure maximal conversion, three to five rounds of stapling were performed. Once stapled, the peptides were cleaved off the resin using trifluoroacetic acid, then precipitated using a hexane:ether (1:1) mixture, and then air dried and purified using LC-MS. We used UV spectroscopy to measure the amount of peptide purified based on the tryptophan extinction coefficient ε=5690 $M^{-1}$ $cm^{-1}$ at 280 nm. Amino acid analysis was also used.

Circular Dichroism Spectroscopy

For characterization of helical structure, the mean molar ellipticities of each peptide was determined using circular dichroism (CD) spectroscopy on an Aviv Biomedical spectrometer. Peptide stock solutions (100 µM) in 10 mM phosphate buffer (pH 7.4) and in a mixture of buffer:2,2,2-trifluoroethanol (1:1 v/v) were loaded into 1-mm fused silica cells and their ellipticity scanned from 195 to 260 nm.

Antimicrobial Activity Assay

The following microbroth dilution protocol was adapted to determine the MIC of each peptide. First, Mueller-Hinton broth (MHB) was passed through an anion exchange column to remove polyanionic species and generate refined MHB. This refined broth was then used in the standard microbroth dilution protocol devised by Hancock et al. for 96 well plates [21]. Note that no BSA was used in the adapted protocol described herein, since initial studies revealed that it could interfere with peptide activity. Briefly, bacterial cells were grown overnight in refined MHB at 37° C. and then diluted and allowed to grow again for several hours. Serial dilutions of peptide stocks in water (10 µl) were prepared using clear round-bottom polypropylene 96-well plates. Then 90 µl of bacteria in refined MHB was added to give a final inoculum of $5\times10^5$ CFU/ml. The plates were then covered with porous tape to reduce evaporation, and incubated for 20-24 hours at 37° C. The MIC was determined by assessing the minimum peptide concentration at which no visible growth was observed.

Hemolytic Activity Assay

For the determination of hemolytic activity, the following protocol was applied: human blood samples were centrifuged to isolate red blood cells (RBCs), which were then washed and suspended in phosphate-buffered saline to yield a 1% (v/v) suspension. This suspension was then added to serial dilutions of peptide stocks in water in clear round-bottom polypropylene 96-well plates and the plates incubated for 1 hour at 37° C. After incubation, the plates were centrifuged and the supernatant isolated to determine the amount of hemoglobin released using a spectrophotometer (570 nm). The minimum hemolytic concentration (MHC) was determined by assessing the peptide concentration at which there was less than 1% hemoglobin release.

REFERENCES

[1] J. R. E. C. L. R. T. C. H. R. P. G. D. A. P. D. M. C. R Monina Klevens, Estimating Health Care-Associated Infections and Deaths in U.S. Hospitals, 2002, Public Health Reports. 122 (2007) 160.

[2] M. Zasloff, Antimicrobial peptides of multicellular organisms, Nature. 415 (2002) 389-395. doi:10.1038/415389a.

[3] K. A. Brogden, Antimicrobial peptides: pore formers or metabolic inhibitors in bacteria?Nat. Rev. Microbiol. 3 (2005) 238-250. doi:10.1038/nrmicro1098.

[4] C. D. Fjell, J. A. Hiss, R. E. W. Hancock, G. Schneider, Designing antimicrobial peptides: form follows function, Nat Rev Drug Discov. 11 (2011) 37-51. doi:10.1038/nrd3591.

[5] Y. J. Gordon, E. G. Romanowski, A. M. McDermott, A Review of Antimicrobial Peptides and Their Therapeutic Potential as Anti-Infective Drugs, Curr Eye Res. 30 (2005) 505-515. doi:10.1080/02713680590968637.

[6] S. C. Mansour, O. M. Pena, R. E. W. Hancock, Host defense peptides: front-line immunomodulators, Trends Immunol. 35 (2014) 443-450. doi:10.1016/j.it.2014.07.004.

[7] H. D. Thaker, A. Som, F. Ayaz, D. Lui, W. Pan, R. W. Scott, et al., Synthetic Mimics of Antimicrobial Peptides with Immunomodulatory Responses, J. Am. Chem. Soc. 134 (2012) 11088-11091. doi:10.1021/ja303304j.

[8] P. Shah, F. S. H. Hsiao, Y. H. Ho, C. S. Chen, The proteome targets of intracellular targeting antimicrobial peptides, Proteomics. (2015). doi:10.1002/pmic.201500380.

[9] P. Nicolas, Multifunctional host defense peptides: intracellular-targeting antimicrobial peptides, FEBS Journal. 276 (2009) 6483-6496. doi:10.1111/j.1742-4658.2009.07359.x.

[10] G. S. Yi, C. B. Park, S. C. Kim, C. Cheong, Solution structure of an antimicrobial peptide buforin II, FEBS Letters. 398 (1996) 87-90.

[11] F. R. A. J. Rose, K. Bailey, J. W. Keyte, W. C. Chan, D. Greenwood, Y. R. Mahida, Potential Role of Epithelial Cell-Derived Histone H1 Proteins in Innate Antimicrobial Defense in the Human Gastrointestinal Tract, Iai.Asm.org. (n.d.).

[12] M. E. Bustillo, A. L. Fischer, M. A. LaBouyer, J. A. Klaips, A. C. Webb, D. E. Elmore, Modular analysis of hipposin, a histone-derived antimicrobial peptide consisting of membrane translocating and membrane permeabilizing fragments, Biochimica Et Biophysica Acta (BBA)—Biomembranes. 1838 (2014) 2228-2233. doi:10.1016/j.bbamem.2014.04.010.

[13] C. B. Park, K. S. Yi, K. Matsuzaki, M. S. Kim, S. C. Kim, Structure-activity analysis of buforin II, a histone $H_2A$-derived antimicrobial peptide: The proline hinge is responsible for the cell-penetrating ability of buforin II, Proceedings of the National Academy of Sciences. 97 (2000) 8245-8250. doi:10.1073/pnas. 150518097.

[14] L. D. Walensky, A. L. Kung, I. Escher, T. J. Malia, S. Barbuto, R. D. Wright, et al., Activation of apoptosis in vivo by a hydrocarbon-stapled BH3 helix, Science. 305 (2004) 1466-1470. doi:10.1126/science.1099191.

[15] L. D. Walensky, G. H. Bird, Hydrocarbon-Stapled Peptides: Principles, Practice, and Progress, J. Med. Chem. (2014) 140306151941006. doi:10.1021/jm4011675.

[16] G. H. Bird, S. Boyapalle, T. Wong, K. Opoku-Nsiah, R. Bedi, W. C. Crannell, et al., Mucosal delivery of a double-stapled RSV peptide prevents nasopulmonary infection, J Clin Invest. 124 (n.d.) 2113-2124. doi:10.1172/JCI71856.

[17] F. Bernal, M. Wade, M. Godes, T. N. Davis, D. G. Whitehead, A. L. Kung, et al., A Stapled p53 Helix Overcomes HDMX-Mediated Suppression of p53, Cancer Cell. 18 (2010) 411-422. doi:10.1016/j.ccr.2010.10.024.

[18] Y. S. Chang, B. Graves, V. Guerlavais, C. Tovar, K. Packman, K.-H. To, et al., Stapled α-helical peptide drug development: A potent dual inhibitor of MDM2 and MDMX for p53-dependent cancer therapy, Pnas.org. (n.d.).

[19] M. P. Pereira, S. O. Kelley, Maximizing the Therapeutic Window of an Antimicrobial Drug by Imparting Mitochondrial Sequestration in Human Cells, J. Am. Chem. Soc. 133 (2011) 3260-3263. doi:10.1021/ja110246u.

[20] A. Patgiri, M. Z. Menzenski, A. B. Mahon, P. S. Arora, Solid-phase synthesis of short α-helices stabilized by the hydrogen bond surrogate approach, Nat Protoc. 5 (2010) 1857-1865. doi:10.1038/nprot.2010.146.

[21] I. Wiegand, K. Hilpert, R. E. W. Hancock, Agar and broth dilution methods to determine the minimal inhibitory concentration (MIC) of antimicrobial substances, Nat Protoc. 3 (2008) 163-175. doi:10.1038/nprot.2007.521.

What is claimed is:

1. A stapled peptide or a pharmaceutically acceptable salt thereof comprising the amino acid sequence TRSSRAGLQWPVGRVX$_1$RLLX$_2$K (SEQ ID NO:38), TRSSRAGLQWPX$_1$GRVX$_2$RLLRK (SEQ ID NO:42), TRSSRAGLX$_1$WPVX$_2$RVHRLLRK (SEQ ID NO:43), TRX$_1$SRAX$_2$LQWPVGRVHRLLRK (SEQ ID NO:47), TRSSRAX$_3$LQWPVGX$_4$VHRLLRK (SEQ ID NO:55), or TRSSX$_3$AGLQWPX$_4$GRVHRLLRK (SEQ ID NO:57), wherein each of X$_1$, X$_2$, X$_3$, and X$_4$ is a non-natural amino acid, wherein X$_1$ and X$_2$ are cross-linked to each other where present, and wherein X$_3$ and X$_4$ are cross-linked to each other where present.

2. The stapled peptide or pharmaceutically acceptable salt thereof of claim 1, wherein each of X$_1$, X$_2$, X$_3$, and X$_4$ is independently an α, α-disubstituted non-natural amino acid comprising an olefinic side chain.

3. The stapled peptide or pharmaceutically acceptable salt thereof of claim 1, wherein each of X$_1$ and X$_2$, and X$_4$ is (S)-2-(4'-pentenyl)alanine, and wherein X$_3$ is (R)-2-(7'-octenyl)alanine.

4. The stapled peptide or pharmaceutically acceptable salt thereof of claim 1, comprising the amino acid sequence TRSSRAGLX$_1$WPVX$_2$RVHRLLRK (SEQ ID NO:43), TRX$_1$SRAX$_2$LQWPVGRVHRLLRK (SEQ ID NO:47), or TRSSRAX$_3$LQWPVGX$_4$VHRLLRK (SEQ ID NO:55), wherein each of X$_1$ and X$_2$, and X$_4$ is (S)-2-(4'-pentenyl)alanine, and wherein X$_3$ is (R)-2-(7'-octenyl)alanine.

5. The stapled peptide or pharmaceutically acceptable salt thereof of claim 1, which is 21 to 30 amino acids in length.

6. The stapled peptide or pharmaceutically acceptable salt thereof of claim 1, wherein the pharmaceutically acceptable salt is an acetate, a citrate, a fumarate, a maleate, a succinate, a sulfate, or a malonate.

7. The stapled peptide or pharmaceutically acceptable salt thereof of claim 1, consisting of the amino acid sequence
TRSSRAGLQWPVGRVX$_1$RLLX$_2$K (SEQ ID NO:38), TRSSRAGLQWPX$_1$GRVX$_2$RLLRK (SEQ ID NO:42), TRSSRAGLX$_1$WPVX$_2$RVHRLLRK (SEQ ID NO:43), TRX$_1$SRAX$_2$LQWPVGRVHRLLRK (SEQ ID NO:47), TRSSRAX$_3$LQWPVGX$_4$VHRLLRK (SEQ ID NO:55), or TRSSX$_3$AGLQWPX$_4$GRVHRLLRK (SEQ ID NO:57).

8. The stapled peptide or pharmaceutically acceptable salt thereof of claim 7, wherein each of X$_1$, X$_2$, X$_3$, and X$_4$ is independently an α, α-disubstituted non-natural amino acid comprising an olefinic side chain.

9. The stapled peptide or pharmaceutically acceptable salt thereof of claim 7, wherein each of X$_1$ and X$_2$, and X$_4$ is (S)-2-(4'-pentenyl)alanine, and wherein X$_3$ is (R)-2-(7'-octenyl)alanine.

10. The stapled peptide or pharmaceutically acceptable salt thereof of claim 1, consisting of the amino acid sequence TRSSRAGLX$_1$WPVX$_2$RVHRLLRK (SEQ ID NO:43), TRX$_1$SRAX$_2$LQWPVGRVHRLLRK (SEQ ID NO:47), or TRSSRAX$_3$LQWPVGX$_4$VHRLLRK (SEQ ID NO:55), wherein each of X$_1$ and X$_2$, and X$_4$ is (S)-2-(4'-pentenyl) alanine, and wherein X$_3$ is (R)-2-(7'-octenyl)alanine.

11. The stapled peptide or pharmaceutically acceptable salt thereof of claim 1, wherein the stapled peptide or pharmaceutically acceptable salt thereof is dihydroxylated.

12. The stapled peptide or pharmaceutically acceptable salt thereof of claim 1, which is linked to an antibiotic or methotrexate.

13. The stapled peptide or pharmaceutically acceptable salt thereof of claim 12, wherein the antibiotic is a Gram-positive antimicrobial.

14. The stapled peptide or pharmaceutically acceptable salt thereof of claim 13, wherein the Gram-positive antimicrobial is a beta-lactam drug.

15. A pharmaceutical composition comprising the stapled peptide or pharmaceutically acceptable salt thereof of claim 1, and a pharmaceutically acceptable carrier.

16. A pharmaceutical composition comprising the stapled peptide or pharmaceutically acceptable salt thereof of claim 3, and a pharmaceutically acceptable carrier.

17. A pharmaceutical composition comprising the stapled peptide or pharmaceutically acceptable salt thereof of claim 4, and a pharmaceutically acceptable carrier.

18. A pharmaceutical composition comprising the stapled peptide or pharmaceutically acceptable salt thereof of claim 7, and a pharmaceutically acceptable carrier.

19. A pharmaceutical composition comprising the stapled peptide or pharmaceutically acceptable salt thereof of claim 10, and a pharmaceutically acceptable carrier.

20. A method of treating a bacterial infection in a human subject in need thereof, the method comprising administering a therapeutically-effective amount of the stapled peptide or pharmaceutically acceptable salt thereof of claim 1 to the human subject.

21. The method of claim 20, wherein the bacterial infection is caused by a Gram-positive bacterium.

22. The method of claim 20, wherein the bacterial infection is caused by a Gram-negative bacterium.

23. The method of claim 20, wherein the bacterial infection is caused by *E. coli, B. cereus, P aeruginosa, S. aureus*, or methicillin-resistant *S. aureus*.

24. The method of claim 20, wherein the stapled peptide or pharmaceutically acceptable salt thereof comprises the amino acid sequence TRSSRAGLX$_1$WPVX$_2$RVHRLLRK (SEQ ID NO:43), TRX$_1$SRAX$_2$LQWPVGRVHRLLRK (SEQ ID NO:47), or TRSSRAX$_3$LQWPVGX$_4$VHRLLRK (SEQ ID NO:55), wherein each of X$_1$ and X$_2$, and X$_4$ is (S)-2-(4'-pentenyl)alanine, and wherein X$_3$ is (R)-2-(7'-octenyl)alanine.

25. The method of claim 20, further comprising administering to the subject a therapeutically-effective amount of an antibiotic.

26. A method of making a stapled peptide or pharmaceutically acceptable salt thereof, the method comprising:
(a) providing a peptide comprising the amino acid sequence:
TRSSRAGLQWPVGRVX$_1$RLLX$_2$K (SEQ ID NO:38), TRSSRAGLQWPX$_1$GRVX$_2$RLLRK (SEQ ID NO:42), TRSSRAGLX$_1$WPVX$_2$RVHRLLRK (SEQ ID NO:43), TRX$_1$SRAX$_2$LQWPVGRVHRLLRK (SEQ ID NO:47), TRSSRAX$_3$LQWPVGX$_4$VHRLLRK (SEQ ID NO:55), or TRSSX$_3$AGLQWPX$_4$GRVHRLLRK (SEQ ID NO:57), wherein each of X$_1$, X$_2$, X$_3$, and X$_4$ is an α, α-disubstituted non-natural amino acid comprising an olefinic side chain; and
(b) performing a ring-closing metathesis reaction on the peptide, thereby making the stapled peptide.

27. The method of claim 26, further comprising formulating the stapled peptide as a sterile pharmaceutical composition.

* * * * *

SEQUENCE LISTING

<160> NUMBER OF SEQ ID NOS: 64

<210> SEQ ID NO 1
<211> LENGTH: 25
<212> TYPE: PRT
<213> ORGANISM: Pseudopleuronectes americanus
<220> FEATURE:
<221> NAME/KEY: MISC_FEATURE
<223> OTHER INFORMATION: C-term NH2

<400> SEQUENCE: 1

Gly Trp Gly Ser Phe Phe Lys Lys Ala Ala His Val Gly Lys His Val
1               5                   10                  15

Gly Lys Ala Ala Leu Thr His Tyr Leu
            20                  25

<210> SEQ ID NO 2
<211> LENGTH: 51
<212> TYPE: PRT
<213> ORGANISM: Hippoglossus hippoglossus

<400> SEQUENCE: 2

Ser Gly Arg Gly Lys Thr Gly Gly Lys Ala Arg Ala Lys Ala Lys Thr
1               5                   10                  15

Arg Ser Ser Arg Ala Gly Leu Gln Phe Pro Val Gly Arg Val His Arg
            20                  25                  30

Leu Leu Arg Lys Gly Asn Tyr Ala His Arg Val Gly Ala Gly Ala Pro
        35                  40                  45

Val Tyr Leu
    50

<210> SEQ ID NO 3
<211> LENGTH: 39
<212> TYPE: PRT
<213> ORGANISM: Himantura pastinacoides

<400> SEQUENCE: 3

Lys Ala Lys Ser Arg Ser Ser Arg Ala Gly Leu Gln Phe Pro Val Gly
1               5                   10                  15

Arg Val His Arg Leu Leu Arg Lys Gly Asn Tyr Ala Glu Arg Val Gly
            20                  25                  30

Ala Gly Ala Pro Val Tyr Leu
        35

<210> SEQ ID NO 4
<211> LENGTH: 51
<212> TYPE: PRT
<213> ORGANISM: Oncorhynchus mykiss

<400> SEQUENCE: 4

Ser Gly Arg Gly Lys Thr Gly Gly Lys Ala Arg Ala Lys Ala Lys Thr
1               5                   10                  15

Arg Ser Ser Arg Ala Gly Leu Gln Phe Pro Val Gly Arg Val His Arg
            20                  25                  30

Leu Leu Arg Lys Gly Asn Tyr Ala Glu Arg Val Gly Ala Gly Ala Pro
        35                  40                  45

Val Tyr Leu
    50

<210> SEQ ID NO 5
<211> LENGTH: 40

```
<212> TYPE: PRT
<213> ORGANISM: Haliotis discus

<400> SEQUENCE: 5

Met Ser Gly Arg Gly Lys Gly Gly Lys Thr Lys Ala Lys Ala Lys Ser
 1               5                  10                  15

Arg Ser Ser Arg Ala Gly Leu Gln Phe Pro Val Gly Arg Ile His Arg
            20                  25                  30

Leu Leu Arg Lys Gly Asn Tyr Ala
        35                  40

<210> SEQ ID NO 6
<211> LENGTH: 40
<212> TYPE: PRT
<213> ORGANISM: Chlamys farreri

<400> SEQUENCE: 6

Met Ser Gly Arg Gly Lys Gly Gly Lys Val Lys Gly Lys Ala Lys Ser
 1               5                  10                  15

Arg Ser Ser Arg Ala Gly Leu Gln Phe Pro Val Gly Arg Ile His Arg
            20                  25                  30

Leu Leu Arg Lys Gly Asn Tyr Ala
        35                  40

<210> SEQ ID NO 7
<211> LENGTH: 21
<212> TYPE: PRT
<213> ORGANISM: Bufo garagrizans

<400> SEQUENCE: 7

Thr Arg Ser Ser Arg Ala Gly Leu Gln Phe Pro Val Gly Arg Val His
 1               5                  10                  15

Arg Leu Leu Arg Lys
            20

<210> SEQ ID NO 8
<211> LENGTH: 10
<212> TYPE: PRT
<213> ORGANISM: Homo sapiens

<400> SEQUENCE: 8

Lys Leu Asn Lys Lys Ala Ala Ser Gly Glu
 1               5                  10

<210> SEQ ID NO 9
<211> LENGTH: 15
<212> TYPE: PRT
<213> ORGANISM: Homo sapiens

<400> SEQUENCE: 9

Lys Leu Asn Lys Lys Ala Ala Ser Gly Glu Ala Lys Pro Lys Ala
 1               5                  10                  15

<210> SEQ ID NO 10
<211> LENGTH: 10
<212> TYPE: PRT
<213> ORGANISM: Homo sapiens

<400> SEQUENCE: 10

Lys Ala Lys Ser Pro Lys Lys Ala Lys Ala
 1               5                  10
```

```
<210> SEQ ID NO 11
<211> LENGTH: 24
<212> TYPE: PRT
<213> ORGANISM: Homo sapiens

<400> SEQUENCE: 11

Asp Ser His Ala Lys Arg Lys Lys Gly Tyr Lys Arg Lys Phe His Glu
1               5                   10                  15

Lys His His Ser His Arg Gly Tyr
            20

<210> SEQ ID NO 12
<211> LENGTH: 19
<212> TYPE: PRT
<213> ORGANISM: Drosophila sp.
<220> FEATURE:
<221> NAME/KEY: MOD_RES
<222> LOCATION: (11)..(11)
<223> OTHER INFORMATION: Glycosylated

<400> SEQUENCE: 12

Gly Lys Pro Arg Pro Tyr Ser Pro Arg Pro Thr Ser His Pro Arg Pro
1               5                   10                  15

Ile Arg Val

<210> SEQ ID NO 13
<211> LENGTH: 18
<212> TYPE: PRT
<213> ORGANISM: Apis mellifera

<400> SEQUENCE: 13

Gly Asn Asn Arg Pro Val Tyr Ile Pro Gln Pro Arg Pro Pro His Pro
1               5                   10                  15

Arg Leu

<210> SEQ ID NO 14
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<223> OTHER INFORMATION: C-term NH2
<220> FEATURE:
<221> NAME/KEY: MOD_RES
<222> LOCATION: (3)..(3)
<223> OTHER INFORMATION: Any amino acid whose side chain has been
      replaced by an internal staple
<220> FEATURE:
<221> NAME/KEY: MOD_RES
<222> LOCATION: (7)..(7)
<223> OTHER INFORMATION: Any amino acid whose side chain has been
      replaced by an internal staple
<220> FEATURE:
<221> NAME/KEY: MOD_RES
<222> LOCATION: (12)..(12)
<223> OTHER INFORMATION: Any amino acid whose side chain has been
      replaced by an internal staple
<220> FEATURE:
<221> NAME/KEY: MOD_RES
<222> LOCATION: (16)..(16)
<223> OTHER INFORMATION: Any amino acid whose side chain has been
      replaced by an internal staple

<400> SEQUENCE: 14

Gly Trp Xaa Ser Phe Phe Xaa Lys Ala Ala His Xaa Gly Lys His Xaa
1               5                   10                  15
```

Gly Lys Ala Ala Leu Thr His Tyr Leu
            20                  25

<210> SEQ ID NO 15
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<223> OTHER INFORMATION: C-term NH2
<220> FEATURE:
<221> NAME/KEY: MOD_RES
<222> LOCATION: (9)..(9)
<223> OTHER INFORMATION: Any amino acid whose side chain has been
      replaced by an internal staple
<220> FEATURE:
<221> NAME/KEY: MOD_RES
<222> LOCATION: (13)..(13)
<223> OTHER INFORMATION: Any amino acid whose side chain has been
      replaced by an internal staple
<220> FEATURE:
<221> NAME/KEY: MOD_RES
<222> LOCATION: (19)..(19)
<223> OTHER INFORMATION: Any amino acid whose side chain has been
      replaced by an internal staple
<220> FEATURE:
<221> NAME/KEY: MOD_RES
<222> LOCATION: (23)..(23)
<223> OTHER INFORMATION: Any amino acid whose side chain has been
      replaced by an internal staple

<400> SEQUENCE: 15

Gly Trp Gly Ser Phe Phe Lys Lys Xaa Ala His Val Xaa Lys His Val
1               5                   10                  15

Gly Lys Xaa Ala Leu Thr Xaa Tyr Leu
            20                  25

<210> SEQ ID NO 16
<211> LENGTH: 51
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (4)..(4)
<223> OTHER INFORMATION: Any amino acid whose side chain has been
      replaced by an internal staple
<220> FEATURE:
<221> NAME/KEY: MOD_RES
<222> LOCATION: (11)..(11)
<223> OTHER INFORMATION: Any amino acid whose side chain has been
      replaced by an internal staple

<400> SEQUENCE: 16

Ser Gly Arg Xaa Lys Thr Gly Gly Lys Ala Xaa Ala Lys Ala Lys Thr
1               5                   10                  15

Arg Ser Ser Arg Ala Gly Leu Gln Phe Pro Val Gly Arg Val His Arg
            20                  25                  30

Leu Leu Arg Lys Gly Asn Tyr Ala His Arg Val Gly Ala Gly Ala Pro
        35                  40                  45

Val Tyr Leu
    50

<210> SEQ ID NO 17

```
<211> LENGTH: 51
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (10)..(10)
<223> OTHER INFORMATION: Any amino acid whose side chain has been
      replaced by an internal staple
<220> FEATURE:
<221> NAME/KEY: MOD_RES
<222> LOCATION: (14)..(14)
<223> OTHER INFORMATION: Any amino acid whose side chain has been
      replaced by an internal staple
<220> FEATURE:
<221> NAME/KEY: MOD_RES
<222> LOCATION: (27)..(27)
<223> OTHER INFORMATION: Any amino acid whose side chain has been
      replaced by an internal staple
<220> FEATURE:
<221> NAME/KEY: MOD_RES
<222> LOCATION: (31)..(31)
<223> OTHER INFORMATION: Any amino acid whose side chain has been
      replaced by an internal staple

<400> SEQUENCE: 17

Ser Gly Arg Gly Lys Thr Gly Gly Lys Xaa Arg Ala Lys Xaa Lys Thr
1               5                   10                  15

Arg Ser Ser Arg Ala Gly Leu Gln Phe Pro Xaa Gly Arg Val Xaa Arg
            20                  25                  30

Leu Leu Arg Lys Gly Asn Tyr Ala His Arg Val Gly Ala Gly Ala Pro
        35                  40                  45

Val Tyr Leu
    50

<210> SEQ ID NO 18
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (6)..(6)
<223> OTHER INFORMATION: Any amino acid whose side chain has been
      replaced by an internal staple
<220> FEATURE:
<221> NAME/KEY: MOD_RES
<222> LOCATION: (10)..(10)
<223> OTHER INFORMATION: Any amino acid whose side chain has been
      replaced by an internal staple
<220> FEATURE:
<221> NAME/KEY: MOD_RES
<222> LOCATION: (29)..(29)
<223> OTHER INFORMATION: Any amino acid whose side chain has been
      replaced by an internal staple
<220> FEATURE:
<221> NAME/KEY: MOD_RES
<222> LOCATION: (36)..(36)
<223> OTHER INFORMATION: Any amino acid whose side chain has been
      replaced by an internal staple

<400> SEQUENCE: 18

Lys Ala Lys Ser Arg Xaa Ser Arg Ala Xaa Leu Gln Phe Pro Val Gly
1               5                   10                  15

Arg Val His Arg Leu Leu Arg Lys Gly Asn Tyr Ala Xaa Arg Val Gly
            20                  25                  30

Ala Gly Ala Xaa Val Tyr Leu
```

<210> SEQ ID NO 19
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (12)..(12)
<223> OTHER INFORMATION: Any amino acid whose side chain has been
      replaced by an internal staple
<220> FEATURE:
<221> NAME/KEY: MOD_RES
<222> LOCATION: (16)..(16)
<223> OTHER INFORMATION: Any amino acid whose side chain has been
      replaced by an internal staple
<220> FEATURE:
<221> NAME/KEY: MOD_RES
<222> LOCATION: (28)..(28)
<223> OTHER INFORMATION: Any amino acid whose side chain has been
      replaced by an internal staple
<220> FEATURE:
<221> NAME/KEY: MOD_RES
<222> LOCATION: (35)..(35)
<223> OTHER INFORMATION: Any amino acid whose side chain has been
      replaced by an internal staple

<400> SEQUENCE: 19

Lys Ala Lys Ser Arg Ser Ser Arg Ala Gly Leu Xaa Phe Pro Val Xaa
1               5                   10                  15

Arg Val His Arg Leu Leu Arg Lys Gly Asn Tyr Xaa Glu Arg Val Gly
            20                  25                  30

Ala Gly Xaa Pro Val Tyr Leu
        35

<210> SEQ ID NO 20
<211> LENGTH: 51
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (20)..(20)
<223> OTHER INFORMATION: Any amino acid whose side chain has been
      replaced by an internal staple
<220> FEATURE:
<221> NAME/KEY: MOD_RES
<222> LOCATION: (27)..(27)
<223> OTHER INFORMATION: Any amino acid whose side chain has been
      replaced by an internal staple
<220> FEATURE:
<221> NAME/KEY: MOD_RES
<222> LOCATION: (36)..(36)
<223> OTHER INFORMATION: Any amino acid whose side chain has been
      replaced by an internal staple
<220> FEATURE:
<221> NAME/KEY: MOD_RES
<222> LOCATION: (43)..(43)
<223> OTHER INFORMATION: Any amino acid whose side chain has been
      replaced by an internal staple

<400> SEQUENCE: 20

Ser Gly Arg Gly Lys Thr Gly Gly Lys Ala Arg Ala Lys Ala Lys Thr
1               5                   10                  15

Arg Ser Ser Xaa Ala Gly Leu Gln Phe Pro Xaa Gly Arg Val His Arg
            20                  25                  30

-continued

Leu Leu Arg Xaa Gly Asn Tyr Ala Glu Arg Xaa Gly Ala Gly Ala Pro
         35                  40                  45

Val Tyr Leu
    50

<210> SEQ ID NO 21
<211> LENGTH: 51
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (10)..(10)
<223> OTHER INFORMATION: Any amino acid whose side chain has been
      replaced by an internal staple
<220> FEATURE:
<221> NAME/KEY: MOD_RES
<222> LOCATION: (17)..(17)
<223> OTHER INFORMATION: Any amino acid whose side chain has been
      replaced by an internal staple
<220> FEATURE:
<221> NAME/KEY: MOD_RES
<222> LOCATION: (34)..(34)
<223> OTHER INFORMATION: Any amino acid whose side chain has been
      replaced by an internal staple
<220> FEATURE:
<221> NAME/KEY: MOD_RES
<222> LOCATION: (41)..(41)
<223> OTHER INFORMATION: Any amino acid whose side chain has been
      replaced by an internal staple

<400> SEQUENCE: 21

Ser Gly Arg Gly Lys Thr Gly Gly Lys Xaa Arg Ala Lys Ala Lys Thr
1               5                   10                  15

Xaa Ser Ser Arg Ala Gly Leu Gln Phe Pro Val Gly Arg Val His Arg
            20                  25                  30

Leu Xaa Arg Lys Gly Asn Tyr Ala Xaa Arg Val Gly Ala Gly Ala Pro
         35                  40                  45

Val Tyr Leu
    50

<210> SEQ ID NO 22
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (8)..(8)
<223> OTHER INFORMATION: Any amino acid whose side chain has been
      replaced by an internal staple
<220> FEATURE:
<221> NAME/KEY: MOD_RES
<222> LOCATION: (15)..(15)
<223> OTHER INFORMATION: Any amino acid whose side chain has been
      replaced by an internal staple

<400> SEQUENCE: 22

Met Ser Gly Arg Gly Lys Gly Xaa Lys Thr Lys Ala Lys Ala Xaa Ser
1               5                   10                  15

Arg Ser Ser Arg Ala Gly Leu Gln Phe Pro Val Gly Arg Ile His Arg
            20                  25                  30

Leu Leu Arg Lys Gly Asn Tyr Ala
         35                  40

<210> SEQ ID NO 23
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (27)..(27)
<223> OTHER INFORMATION: Any amino acid whose side chain has been
      replaced by an internal staple
<220> FEATURE:
<221> NAME/KEY: MOD_RES
<222> LOCATION: (34)..(34)
<223> OTHER INFORMATION: Any amino acid whose side chain has been
      replaced by an internal staple

<400> SEQUENCE: 23

Met Ser Gly Arg Gly Lys Gly Lys Thr Lys Ala Lys Ala Lys Ser
1               5                   10                  15

Arg Ser Ser Arg Ala Gly Leu Gln Phe Pro Xaa Gly Arg Ile His Arg
            20                  25                  30

Leu Xaa Arg Lys Gly Asn Tyr Ala
        35                  40

<210> SEQ ID NO 24
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Any amino acid whose side chain has been
      replaced by an internal staple
<220> FEATURE:
<221> NAME/KEY: MOD_RES
<222> LOCATION: (8)..(8)
<223> OTHER INFORMATION: Any amino acid whose side chain has been
      replaced by an internal staple

<400> SEQUENCE: 24

Xaa Ser Gly Arg Gly Lys Gly Xaa Lys Val Lys Gly Lys Ala Lys Ser
1               5                   10                  15

Arg Ser Ser Arg Ala Gly Leu Gln Phe Pro Val Gly Arg Ile His Arg
            20                  25                  30

Leu Leu Arg Lys Gly Asn Tyr Ala
        35                  40

<210> SEQ ID NO 25
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (14)..(14)
<223> OTHER INFORMATION: Any amino acid whose side chain has been
      replaced by an internal staple
<220> FEATURE:
<221> NAME/KEY: MOD_RES
<222> LOCATION: (21)..(21)
<223> OTHER INFORMATION: Any amino acid whose side chain has been
      replaced by an internal staple

```
<400> SEQUENCE: 25

Met Ser Gly Arg Gly Lys Gly Gly Lys Val Lys Gly Lys Xaa Lys Ser
1               5                   10                  15

Arg Ser Ser Arg Xaa Gly Leu Gln Phe Pro Val Gly Arg Ile His Arg
            20                  25                  30

Leu Leu Arg Lys Gly Asn Tyr Ala
        35                  40

<210> SEQ ID NO 26
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)..(12)
<223> OTHER INFORMATION: Any amino acid whose side chain has been
      replaced by an internal staple
<220> FEATURE:
<221> NAME/KEY: MOD_RES
<222> LOCATION: (15)..(15)
<223> OTHER INFORMATION: Any amino acid whose side chain has been
      replaced by an internal staple

<400> SEQUENCE: 26

Thr Arg Ser Ser Arg Ala Gly Leu Gln Phe Pro Xaa Gly Arg Xaa His
1               5                   10                  15

Arg Leu Leu Arg Lys
            20

<210> SEQ ID NO 27
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (15)..(15)
<223> OTHER INFORMATION: Any amino acid whose side chain has been
      replaced by an internal staple
<220> FEATURE:
<221> NAME/KEY: MOD_RES
<222> LOCATION: (19)..(19)
<223> OTHER INFORMATION: Any amino acid whose side chain has been
      replaced by an internal staple

<400> SEQUENCE: 27

Thr Arg Ser Ser Arg Ala Gly Leu Gln Phe Pro Val Gly Arg Xaa His
1               5                   10                  15

Arg Leu Xaa Arg Lys
            20

<210> SEQ ID NO 28
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)..(12)
<223> OTHER INFORMATION: Any amino acid whose side chain has been
      replaced by an internal staple
<220> FEATURE:
```

```
<221> NAME/KEY: MOD_RES
<222> LOCATION: (19)..(19)
<223> OTHER INFORMATION: Any amino acid whose side chain has been
      replaced by an internal staple

<400> SEQUENCE: 28

Thr Arg Ser Ser Arg Ala Gly Leu Gln Phe Pro Xaa Gly Arg Val His
1               5                   10                  15

Arg Leu Xaa Arg Lys
            20

<210> SEQ ID NO 29
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Any amino acid whose side chain has been
      replaced by an internal staple
<220> FEATURE:
<221> NAME/KEY: MOD_RES
<222> LOCATION: (6)..(6)
<223> OTHER INFORMATION: Any amino acid whose side chain has been
      replaced by an internal staple

<400> SEQUENCE: 29

Lys Xaa Asn Lys Lys Xaa Ala Ser Gly Glu Ala Lys Pro Lys Ala
1               5                   10                  15

<210> SEQ ID NO 30
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Any amino acid whose side chain has been
      replaced by an internal staple
<220> FEATURE:
<221> NAME/KEY: MOD_RES
<222> LOCATION: (10)..(10)
<223> OTHER INFORMATION: Any amino acid whose side chain has been
      replaced by an internal staple

<400> SEQUENCE: 30

Lys Ala Xaa Ser Pro Lys Lys Ala Lys Xaa
1               5                   10

<210> SEQ ID NO 31
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Any amino acid whose side chain has been
      replaced by an internal staple
<220> FEATURE:
<221> NAME/KEY: MOD_RES
<222> LOCATION: (13)..(13)
<223> OTHER INFORMATION: Any amino acid whose side chain has been
      replaced by an internal staple
```

```
<400> SEQUENCE: 31

Asp Ser His Ala Xaa Arg Lys Lys Gly Tyr Lys Arg Xaa Phe His Glu
1               5                   10                  15

Lys His His Ser His Arg Gly Tyr
            20

<210> SEQ ID NO 32
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Any amino acid whose side chain has been
      replaced by an internal staple
<220> FEATURE:
<221> NAME/KEY: MOD_RES
<222> LOCATION: (7)..(7)
<223> OTHER INFORMATION: Any amino acid whose side chain has been
      replaced by an internal staple
<220> FEATURE:
<221> NAME/KEY: MOD_RES
<222> LOCATION: (14)..(14)
<223> OTHER INFORMATION: Any amino acid whose side chain has been
      replaced by an internal staple
<220> FEATURE:
<221> NAME/KEY: MOD_RES
<222> LOCATION: (21)..(21)
<223> OTHER INFORMATION: Any amino acid whose side chain has been
      replaced by an internal staple

<400> SEQUENCE: 32

Asp Ser Xaa Ala Lys Arg Xaa Lys Gly Tyr Lys Arg Lys Xaa His Glu
1               5                   10                  15

Lys His His Ser Xaa Arg Gly Tyr
            20

<210> SEQ ID NO 33
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid whose side chain has been
      replaced by an internal staple
<220> FEATURE:
<221> NAME/KEY: MOD_RES
<222> LOCATION: (8)..(8)
<223> OTHER INFORMATION: Any amino acid whose side chain has been
      replaced by an internal staple
<220> FEATURE:
<221> NAME/KEY: MOD_RES
<222> LOCATION: (11)..(11)
<223> OTHER INFORMATION: Glycosylated

<400> SEQUENCE: 33

Xaa Lys Pro Arg Pro Tyr Ser Xaa Arg Pro Thr Ser His Pro Arg Pro
1               5                   10                  15

Ile Arg Val

<210> SEQ ID NO 34
<211> LENGTH: 19
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Any amino acid whose side chain has been
      replaced by an internal staple
<220> FEATURE:
<221> NAME/KEY: MOD_RES
<222> LOCATION: (11)..(11)
<223> OTHER INFORMATION: Glycosylated
<220> FEATURE:
<221> NAME/KEY: MOD_RES
<222> LOCATION: (14)..(14)
<223> OTHER INFORMATION: Any amino acid whose side chain has been
      replaced by an internal staple

<400> SEQUENCE: 34

Gly Lys Pro Arg Pro Tyr Xaa Pro Arg Pro Thr Ser His Xaa Arg Pro
1               5                   10                  15

Ile Arg Val

<210> SEQ ID NO 35
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Any amino acid whose side chain has been
      replaced by an internal staple
<220> FEATURE:
<221> NAME/KEY: MOD_RES
<222> LOCATION: (13)..(13)
<223> OTHER INFORMATION: Any amino acid whose side chain has been
      replaced by an internal staple

<400> SEQUENCE: 35

Gly Asn Asn Arg Pro Xaa Tyr Ile Pro Gln Pro Arg Xaa Pro His Pro
1               5                   10                  15

Arg Leu

<210> SEQ ID NO 36
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Any amino acid whose side chain has been
      replaced by an internal staple
<220> FEATURE:
<221> NAME/KEY: MOD_RES
<222> LOCATION: (8)..(8)
<223> OTHER INFORMATION: Any amino acid whose side chain has been
      replaced by an internal staple
<220> FEATURE:
<221> NAME/KEY: MOD_RES
<222> LOCATION: (15)..(15)
<223> OTHER INFORMATION: Any amino acid whose side chain has been
      replaced by an internal staple
<220> FEATURE:
<221> NAME/KEY: MOD_RES
<222> LOCATION: (18)..(18)
```

<223> OTHER INFORMATION: Any amino acid whose side chain has been
       replaced by an internal staple

<400> SEQUENCE: 36

Gly Asn Asn Xaa Pro Val Tyr Xaa Pro Gln Pro Arg Pro Pro Xaa Pro
1               5                   10                  15

Arg Xaa

<210> SEQ ID NO 37
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (17)..(17)
<223> OTHER INFORMATION: (S)-2-(4'-pentenyl)alanine
<220> FEATURE:
<221> NAME/KEY: MOD_RES
<222> LOCATION: (21)..(21)
<223> OTHER INFORMATION: (S)-2-(4'-pentenyl)alanine

<400> SEQUENCE: 37

Thr Arg Ser Ser Arg Ala Gly Leu Gln Trp Pro Val Gly Arg Val His
1               5                   10                  15

Ala Leu Leu Arg Ala
            20

<210> SEQ ID NO 38
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (16)..(16)
<223> OTHER INFORMATION: (S)-2-(4'-pentenyl)alanine
<220> FEATURE:
<221> NAME/KEY: MOD_RES
<222> LOCATION: (20)..(20)
<223> OTHER INFORMATION: (S)-2-(4'-pentenyl)alanine

<400> SEQUENCE: 38

Thr Arg Ser Ser Arg Ala Gly Leu Gln Trp Pro Val Gly Arg Val Ala
1               5                   10                  15

Arg Leu Leu Ala Lys
            20

<210> SEQ ID NO 39
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (15)..(15)
<223> OTHER INFORMATION: (S)-2-(4'-pentenyl)alanine
<220> FEATURE:
<221> NAME/KEY: MOD_RES
<222> LOCATION: (19)..(19)
<223> OTHER INFORMATION: (S)-2-(4'-pentenyl)alanine

<400> SEQUENCE: 39

Thr Arg Ser Ser Arg Ala Gly Leu Gln Trp Pro Val Gly Arg Ala His
1               5                   10                  15

Arg Leu Ala Arg Lys
            20

<210> SEQ ID NO 40
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (14)..(14)
<223> OTHER INFORMATION: (S)-2-(4'-pentenyl)alanine
<220> FEATURE:
<221> NAME/KEY: MOD_RES
<222> LOCATION: (18)..(18)
<223> OTHER INFORMATION: (S)-2-(4'-pentenyl)alanine

<400> SEQUENCE: 40

Thr Arg Ser Ser Arg Ala Gly Leu Gln Trp Pro Val Gly Ala Val His
1               5                   10                  15

Arg Ala Leu Arg Lys
            20

<210> SEQ ID NO 41
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)..(13)
<223> OTHER INFORMATION: (S)-2-(4'-pentenyl)alanine
<220> FEATURE:
<221> NAME/KEY: MOD_RES
<222> LOCATION: (17)..(17)
<223> OTHER INFORMATION: (S)-2-(4'-pentenyl)alanine

<400> SEQUENCE: 41

Thr Arg Ser Ser Arg Ala Gly Leu Gln Trp Pro Val Ala Arg Val His
1               5                   10                  15

Ala Leu Leu Arg Lys
            20

<210> SEQ ID NO 42
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)..(12)
<223> OTHER INFORMATION: (S)-2-(4'-pentenyl)alanine
<220> FEATURE:
<221> NAME/KEY: MOD_RES
<222> LOCATION: (16)..(16)
<223> OTHER INFORMATION: (S)-2-(4'-pentenyl)alanine

<400> SEQUENCE: 42

Thr Arg Ser Ser Arg Ala Gly Leu Gln Trp Pro Ala Gly Arg Val Ala
1               5                   10                  15

Arg Leu Leu Arg Lys

```
<210> SEQ ID NO 43
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: (S)-2-(4'-pentenyl)alanine
<220> FEATURE:
<221> NAME/KEY: MOD_RES
<222> LOCATION: (13)..(13)
<223> OTHER INFORMATION: (S)-2-(4'-pentenyl)alanine

<400> SEQUENCE: 43

Thr Arg Ser Ser Arg Ala Gly Leu Ala Trp Pro Val Ala Arg Val His
1               5                   10                  15

Arg Leu Leu Arg Lys
            20

<210> SEQ ID NO 44
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: (S)-2-(4'-pentenyl)alanine
<220> FEATURE:
<221> NAME/KEY: MOD_RES
<222> LOCATION: (12)..(12)
<223> OTHER INFORMATION: (S)-2-(4'-pentenyl)alanine

<400> SEQUENCE: 44

Thr Arg Ser Ser Arg Ala Gly Ala Gln Trp Pro Ala Gly Arg Val His
1               5                   10                  15

Arg Leu Leu Arg Lys
            20

<210> SEQ ID NO 45
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: (S)-2-(4'-pentenyl)alanine
<220> FEATURE:
<221> NAME/KEY: MOD_RES
<222> LOCATION: (9)..(9)
<223> OTHER INFORMATION: (S)-2-(4'-pentenyl)alanine

<400> SEQUENCE: 45

Thr Arg Ser Ser Ala Ala Gly Leu Ala Trp Pro Val Gly Arg Val His
1               5                   10                  15

Arg Leu Leu Arg Lys
            20

<210> SEQ ID NO 46
```

```
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: (S)-2-(4'-pentenyl)alanine
<220> FEATURE:
<221> NAME/KEY: MOD_RES
<222> LOCATION: (8)..(8)
<223> OTHER INFORMATION: (S)-2-(4'-pentenyl)alanine

<400> SEQUENCE: 46

Thr Arg Ser Ala Arg Ala Gly Ala Gln Trp Pro Val Gly Arg Val His
1               5                   10                  15

Arg Leu Leu Arg Lys
            20

<210> SEQ ID NO 47
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: (S)-2-(4'-pentenyl)alanine
<220> FEATURE:
<221> NAME/KEY: MOD_RES
<222> LOCATION: (7)..(7)
<223> OTHER INFORMATION: (S)-2-(4'-pentenyl)alanine

<400> SEQUENCE: 47

Thr Arg Ala Ser Arg Ala Ala Leu Gln Trp Pro Val Gly Arg Val His
1               5                   10                  15

Arg Leu Leu Arg Lys
            20

<210> SEQ ID NO 48
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: (S)-2-(4'-pentenyl)alanine
<220> FEATURE:
<221> NAME/KEY: MOD_RES
<222> LOCATION: (6)..(6)
<223> OTHER INFORMATION: (S)-2-(4'-pentenyl)alanine

<400> SEQUENCE: 48

Thr Ala Ser Ser Arg Ala Gly Leu Gln Trp Pro Val Gly Arg Val His
1               5                   10                  15

Arg Leu Leu Arg Lys
            20

<210> SEQ ID NO 49
<211> LENGTH: 21
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: (S)-2-(4'-pentenyl)alanine
<220> FEATURE:
<221> NAME/KEY: MOD_RES
<222> LOCATION: (5)..(5)
<223> OTHER INFORMATION: (S)-2-(4'-pentenyl)alanine

<400> SEQUENCE: 49

Ala Arg Ser Ser Ala Ala Gly Leu Gln Trp Pro Val Gly Arg Val His
1               5                   10                  15

Arg Leu Leu Arg Lys
            20

<210> SEQ ID NO 50
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (14)..(14)
<223> OTHER INFORMATION: (R)-2-(7'-octenyl)alanine
<220> FEATURE:
<221> NAME/KEY: MOD_RES
<222> LOCATION: (21)..(21)
<223> OTHER INFORMATION: (S)-2-(4'-pentenyl)alanine

<400> SEQUENCE: 50

Thr Arg Ser Ser Arg Ala Gly Leu Gln Trp Pro Val Gly Ala Val His
1               5                   10                  15

Arg Leu Leu Arg Ala
            20

<210> SEQ ID NO 51
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)..(13)
<223> OTHER INFORMATION: (R)-2-(7'-octenyl)alanine
<220> FEATURE:
<221> NAME/KEY: MOD_RES
<222> LOCATION: (20)..(20)
<223> OTHER INFORMATION: (S)-2-(4'-pentenyl)alanine

<400> SEQUENCE: 51

Thr Arg Ser Ser Arg Ala Gly Leu Gln Trp Pro Val Ala Arg Val His
1               5                   10                  15

Arg Leu Leu Ala Lys
            20

<210> SEQ ID NO 52
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
```

```
<222> LOCATION: (12)..(12)
<223> OTHER INFORMATION: (R)-2-(7'-octenyl)alanine
<220> FEATURE:
<221> NAME/KEY: MOD_RES
<222> LOCATION: (19)..(19)
<223> OTHER INFORMATION: (S)-2-(4'-pentenyl)alanine

<400> SEQUENCE: 52

Thr Arg Ser Ser Arg Ala Gly Leu Gln Trp Pro Ala Gly Arg Val His
1               5                   10                  15

Arg Leu Ala Arg Lys
            20

<210> SEQ ID NO 53
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: (R)-2-(7'-octenyl)alanine
<220> FEATURE:
<221> NAME/KEY: MOD_RES
<222> LOCATION: (16)..(16)
<223> OTHER INFORMATION: (S)-2-(4'-pentenyl)alanine

<400> SEQUENCE: 53

Thr Arg Ser Ser Arg Ala Gly Leu Ala Trp Pro Val Gly Arg Val Ala
1               5                   10                  15

Arg Leu Leu Arg Lys
            20

<210> SEQ ID NO 54
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: (R)-2-(7'-octenyl)alanine
<220> FEATURE:
<221> NAME/KEY: MOD_RES
<222> LOCATION: (15)..(15)
<223> OTHER INFORMATION: (S)-2-(4'-pentenyl)alanine

<400> SEQUENCE: 54

Thr Arg Ser Ser Arg Ala Gly Ala Gln Trp Pro Val Gly Arg Ala His
1               5                   10                  15

Arg Leu Leu Arg Lys
            20

<210> SEQ ID NO 55
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: (R)-2-(7'-octenyl)alanine
<220> FEATURE:
<221> NAME/KEY: MOD_RES
```

```
<222> LOCATION: (14)..(14)
<223> OTHER INFORMATION: (S)-2-(4'-pentenyl)alanine

<400> SEQUENCE: 55

Thr Arg Ser Ser Arg Ala Ala Leu Gln Trp Pro Val Gly Ala Val His
1               5                   10                  15

Arg Leu Leu Arg Lys
            20

<210> SEQ ID NO 56
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: (R)-2-(7'-octenyl)alanine
<220> FEATURE:
<221> NAME/KEY: MOD_RES
<222> LOCATION: (13)..(13)
<223> OTHER INFORMATION: (S)-2-(4'-pentenyl)alanine

<400> SEQUENCE: 56

Thr Arg Ser Ser Arg Ala Gly Leu Gln Trp Pro Val Ala Arg Val His
1               5                   10                  15

Arg Leu Leu Arg Lys
            20

<210> SEQ ID NO 57
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: (R)-2-(7'-octenyl)alanine
<220> FEATURE:
<221> NAME/KEY: MOD_RES
<222> LOCATION: (12)..(12)
<223> OTHER INFORMATION: (S)-2-(4'-pentenyl)alanine

<400> SEQUENCE: 57

Thr Arg Ser Ser Ala Ala Gly Leu Gln Trp Pro Ala Gly Arg Val His
1               5                   10                  15

Arg Leu Leu Arg Lys
            20

<210> SEQ ID NO 58
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: (R)-2-(7'-octenyl)alanine
<220> FEATURE:
<221> NAME/KEY: MOD_RES
<222> LOCATION: (9)..(9)
<223> OTHER INFORMATION: (S)-2-(4'-pentenyl)alanine

<400> SEQUENCE: 58
```

```
Thr Ala Ser Ser Arg Ala Gly Leu Ala Trp Pro Val Gly Arg Val His
1               5                   10                  15

Arg Leu Leu Arg Lys
            20

<210> SEQ ID NO 59
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: (R)-2-(7'-octenyl)alanine
<220> FEATURE:
<221> NAME/KEY: MOD_RES
<222> LOCATION: (8)..(8)
<223> OTHER INFORMATION: (S)-2-(4'-pentenyl)alanine

<400> SEQUENCE: 59

Ala Arg Ser Ser Arg Ala Gly Ala Gln Trp Pro Val Gly Arg Val His
1               5                   10                  15

Arg Leu Leu Arg Lys
            20

<210> SEQ ID NO 60
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Thr Arg Ser Ser Arg Ala Gly Leu Gln Trp Pro Val Gly Arg Val His
1               5                   10                  15

Arg Leu Leu Arg Lys
            20

<210> SEQ ID NO 61
<211> LENGTH: 6
<212> TYPE: PRT
<213> ORGANISM: Bufo gargarizans

<400> SEQUENCE: 61

Leu Gln Phe Pro Val Gly
1               5

<210> SEQ ID NO 62
<211> LENGTH: 6
<212> TYPE: PRT
<213> ORGANISM: Artificial Sequence
<220> FEATURE:
<223> OTHER INFORMATION: synthetic peptide

<400> SEQUENCE: 62

Leu Gln Trp Pro Val Gly
1               5

<210> SEQ ID NO 63
<211> LENGTH: 6
<212> TYPE: PRT
<213> ORGANISM: Bufo gargarizans
```

```
<400> SEQUENCE: 63

Ala Gly Leu Gln Phe Pro
1               5

<210> SEQ ID NO 64
<211> LENGTH: 6
<212> TYPE: PRT
<213> ORGANISM: Artificial Sequence
<220> FEATURE:
<223> OTHER INFORMATION: synthetic peptide

<400> SEQUENCE: 64

Ala Gly Leu Gln Trp Pro
1               5
```